US005744302A

United States Patent [19]
Sessler et al.

[11] Patent Number: 5,744,302
[45] Date of Patent: Apr. 28, 1998

[54] METHOD FOR SEPARATING MOLECULES

[75] Inventors: Jonathan L. Sessler; Brent L. Iverson; Vladimir Král; Kevin Shreder, all of Austin, Tex.; Hiroyuki Furuta, Oita, Japan; Richard E. Thomas, Port Smith, R.I.

[73] Assignee: Board of Regents, The University of Texas System, Austin, Tex.

[21] Appl. No.: 438,948

[22] Filed: May 11, 1995

Related U.S. Application Data

[60] Division of Ser. No. 424,288, Apr. 20, 1995, which is a continuation-in-part of Ser. No. 964,607, Oct. 21, 1992, Pat. No. 5,457,195.

[51] Int. Cl.$^6$ .............. C12Q 1/68; C12Q 1/70; C12P 19/34; C07H 21/04
[52] U.S. Cl. .............. 435/6; 435/5; 435/91.2; 435/91.1; 422/48; 540/472; 540/145; 536/24.3; 536/24.32; 536/24.33
[58] Field of Search ................... 435/6, 5, 91.1, 435/91.2; 422/48; 423/129; 540/472, 145; 536/24.3–24.33

[56] References Cited

U.S. PATENT DOCUMENTS

| | | | |
|---|---|---|---|
| 4,318,825 | 3/1982 | Frame | 252/428 |
| 4,602,987 | 7/1986 | Bonaventura et al. | 204/129 |
| 4,835,263 | 5/1989 | Nguyen et al. | 536/27 |
| 4,878,891 | 11/1989 | Judy et al. | 604/5 |
| 4,883,790 | 11/1989 | Levy et al. | |
| 4,915,683 | 4/1990 | Sieber | 604/4 |
| 4,935,498 | 6/1990 | Sessler et al. | 534/15 |
| 5,041,078 | 8/1991 | Matthews et al. | |
| 5,120,411 | 6/1992 | Sessler et al. | 204/157.15 |
| 5,141,911 | 8/1992 | Meunier et al. | 502/159 |
| 5,159,065 | 10/1992 | Sessler et al. | 534/15 |
| 5,162,509 | 11/1992 | Sessler et al. | 534/15 |
| 5,242,797 | 9/1993 | Hirschfeld | 435/6 |
| 5,252,720 | 10/1993 | Sessler et al. | 534/11 |
| 5,272,056 | 12/1993 | Burrows et al. | 435/6 |
| 5,302,714 | 4/1994 | Sessler et al. | 540/472 |
| 5,371,199 | 12/1994 | Therien et al. | 534/11 |
| 5,457,195 | 10/1995 | Sessler et al. | 540/472 |

FOREIGN PATENT DOCUMENTS

| | | |
|---|---|---|
| 0111418 | 6/1984 | European Pat. Off. |
| 0 196 515 | 3/1986 | European Pat. Off. |
| 0 233 701 | 1/1987 | European Pat. Off. |
| WO 90/10633 | 9/1990 | European Pat. Off. |
| WO 94/09003 | 4/1994 | WIPO |

OTHER PUBLICATIONS

Bauer et al., "Sapphyrins: Novel Aromatic Pentapyrrolic Macrocycles," *J Am Chem Soc*, 105:6429–6436 (1983).
Broadhurst and Grigg, "The Synthesis of 22 π-Electron Macrocycles. Sapphyrins and Related Compounds," *JCS Perkin*, 2111–2116 (1972).
Claude et al., "Binding of Nucleosides, Nucleotides, and Anionic Planar Substrates by Bis–Intercaland Receptor Molecules," *J Chem Soc, Chem Commun*, 17:1182–1185 (1991).
Cramer et al., "Synthesis and Structure of the Chloride and Nitrate Inclusion Complexes of [16–Pyrmidinium crown–4]," *J Am Chem Soc*, 113:7033–7034 (1991).
Cuellar and Marks, "Synthesis and Characterization of Metallo and Metal–Free Octaalkylphthalocyanines and Uranyl Decaalkylsuperphthalocyanines," *Inorg Chem*, 20:3766–3770 (1981).
Dietrich et al., "Proton Coupled Membrane Transport of Anions Mediated by Cryptate Carriers," *J Chem Soc Chem Comm*, 11:691–692 (1988).
Dixon et al., "Molecular Recognition: Bis–Acylguanidiniums Provide a Simple Family of Receptors for Phosphodiesters," *J Am Chem Soc*, 114:365–366 (1992).
Furuta et al., "Phosphate Anion Binding: Enhanced Transport of Nucleotide Monophosphates Using a Sapphyrin Carrier," *J Am Chem Soc*, 113:6677–6678 (1991).
Furuta et al., "Enhanced Transport of Nucleosides and Nucleoside Analogues with Complementary Base–Pairing Agents," *J Am Chem Soc*, 113:4706–4707 (1991).
Galan et al., "A Synthetic Receptor for Dinucleotides," *J Am Chem Soc*, 113:9424–9425 (1991).
Galan et al., "Selective Complexation of Adenosine Monophosphate Nucleotides by Rigid Bicyclic Guanidinium Abiotic Receptors," *Tetrahedron Letters*, 32(15):1827–1830 (1991).
Hosseini et al., "Multiple Molecular Recognition and Catalysis. A Multifunctional Anion Receptor Bearing an Anion Binding Site, an Intercalating Group, and a Catalytic Site for Nucleotide Binding and Hydrolysis," *J Am Chem Soc*, 112:3896–3904 (1990).

(List continued on next page.)

*Primary Examiner*—W. Gary Jones
*Assistant Examiner*—Dianne Rees
*Attorney, Agent, or Firm*—Jacqueline S. Larson

[57] ABSTRACT

The present invention provides various novel covalently modified sapphyrin derivatives and conjugates; polymers including sapphyrin or derivatives thereof; and chromatographic supports including sapphyrins and other expanded porphyrins and derivatives thereof. Disclosed are water soluble sapphyrins, including polyhydroxysapphyrins and sapphyrin-sugar derivatives; sapphyrin-metal chelating conjugates; sapphyrin nucleobase conjugates; oligosapphyrins and polysapphyrins, including sapphyrin dimers, trimers, oligomers and higher polymers; and polymer supported expanded porphyrin compositions, including advantageous rubyrin- and sapphyrin-based chromatography columns and electrophoretic supports. Sapphyrin oligomers and polymers and polymer supported expanded porphyrins, such as, e.g., glass and silica expanded porphyrin constructs, are disclosed which include both repeating units of sapphyrin derivatives alone and which include other units, for example, nucleobases, sapphyrin-nucleobase conjugates and long chain alkyl groups.

20 Claims, 29 Drawing Sheets

OTHER PUBLICATIONS

Hosseini et al., "Multiple Molecular Recognition and Catalysis. Nucleotide Binding and ATP Hydrolysis by a Receptor Molecule Bearing an Anion Binding Site, an Intercalator Group and a Catalytic Site," *J Chem Soc Chem Comm*, 9:596–598 (1988).

Kimura et al., "A Study of New Bis(macrocyclic polyamine) Ligands as Inorganic and Organic Anion Receptors," *J Org Chem*, 55(1):46–48 (1990).

Kral et al., "Synthetic Sapphyrin–Cytosine Conjugates: Carriers for Selective Nucleotide Transport at Neutral pH," *J Am Chem Soc*, 114:8704–8705 (1992).

Li and Diederich, "Carriers for Liquid Membrane Transport of Nucleotide 5'–Triphosphates," *J Org Chem*, 47:3449–3454 (1992).

Marks and Stojakowvic, "Large Metal Ion–Centered Template Reactions. Chemical and Spectral Studies of the 'Superphthalocyanine' Dioxocyclopentakis (1–iminoisoindolinato) uranium(VI) and Its Derivatives," *J Am Chem Soc*, 1695–1705 (1978).

Rexhausen and Gossauer, "The Synthesis of a New 22 π–Electron Macrocycle: Pentaphyrin," *Chem Soc Chem Comm*, 6:275 (1983).

Schmidtchen, "A Non–Macrocyclic Host for Binding Organic Phosphates in Protic Solvents," *Tetr Lett*, 30(34):4493–4496 (1989).

Seel and Vogtle, "Molecular Recognition and Transport of Nucleobases—Superiority of Macrobicyclid Host Molecules," *Angew Chem Int Ed Engl*, 30(4):442–444 (1991).

Sessler et al., "Anion Binding: A New Direction in Porphyrin–Related Research," *Pure & Appl Chem*, 65(3):393–398 (1993).

Sessler et al., "Cytosine Amine Derivatives," *J Org Chem*, 47:826–834 (1992).

Sessler et al., "In vitro photodynamic activity of diprotonated sapphyrin: a 22–π–electron pentapyrrolic prophyrin–like macrocycle," *Chem Abstr*, 112:348–349, 112:194584t (1990).

Sessler et al., "A water–stable gadolinium (III) complex derived from a new pentadentate expanded porphyrin ligand," *Chem Abstr*, 111:720, 111:125716e (1989).

Sessler et al., "Synthetic and Structural Studies of Sapphyrin, a 22–π–Electron Pentapyrrolic 'Expanded Porphyrin'," *J Am Chem Soc*, 112:2810–2813 (1990).

Sessler et al., "An 'Expanded Porphyrin': The Synthesis and Structure of a New Aromatic Pentadentate Ligand," *J Am Chem Soc*, 110:5586–5588 (1988).

Shionoya et al., "Diprotonated Sapphyrin: A Fluoride Selective Halide Anion Receptor," *J Am Chem Soc*, 114:5714–5722 (1992).

Tabushi et al., "Lipophilic Diammonium Cation Having a Rigid Structure Complementary to Pyrophosphate Dianions of Nucleotides. Selective Extraction and Transport of Nucleotides," *J Am Chem Soc*, 103:6152–6157 (1981).

Tohda et al., "Liquid Membrane Electrode for Guanosine Nucleotides Using a Cytosine–Pendant Triamine Host as the Sensory Element," *Analyt Chem*, 64(8):960–964 (1992).

International Search Report, mailed Feb. 3, 1994.

International Search Report, mailed Feb. 22, 1994.

Iverson et al., "Phosphate Recognition by Sapphyrin. A New Approach to DNA Binding," *J. Am. Chem. Soc.*, 115:11022–11023 (1993).

Sessler et al., "Phosphate Anion Chelation and Base–pairing. Design of Receptors and Carriers for Nucleotides and Nucleotide Analogs," *Supramolec. Chem.*, 1:209–220 (1993).

Sessler et al., "Expanded Porphyrins. Receptors for Cationic, Anionic, and Neutral Substrates," in *Transition Metals in Supramolecular Chemistry*, NATO ASI Series; Fabbrizzi, L. and Poggi, A., Eds., Kluwer, Dorderecht, Series C, 448:391–408 (1994).

Collman et al., "Synthesis of 'Face to Face' Porphyrin Dimers Linked by 5, 15–Substituents: Potential Binuclear Multielectron Redox Catalysts," *JACS*, 103:516–533 (1981).

Kambe and Yasuda, "The Potassium Flouride–Catalyzed Reaction. V. Aldol Condensation of Nitroalkanes and Aliphatic Aledhydes," *Bull. Chem. Soc. of Japan*, 41(6):1444–1446 (1968).

Tindall, "Esters of Nitroalcohols," *Industrial and Engineering Chemistry*, 33(1):65–66 (1941).

PCT Search Report for PCT/US90/01208, mailed Aug. 2, 1990, printed in USA.

International Search Report for International Application No. PCT/US90/07609, published in Europe.

Gossauer, "Syntheses of Some Unusual Polypyrrole Macrocyles," *Bull. Soc. Chem. Belg.*, 92(9):793–795 (1983).

Král et al., "A Covalently Linked Sapphyrin Dimer. A New Receptor for Dicarboxylate Anions," *J. Am. Chem. Soc.*, 117:2953–2954 (1995).

Kus et al., "First Representatives of Porphyrinylnucleosides," *Tetrahedron Letters*, 31:5133–5134 (1990).

Maiya et al., "In Vitro Photodynamic Activity of Diprotonated Sapphyrin: a 22–pi–electron Pentapyrrolic Porphyrin––like Macrocycle," *Chem. Absts.*, 112:348–349, Abstract #194584t (1990).

Sessler et al., "Synthesis and Crystal Structure of a Novel Tripyrrane–Containing Porphyrinogen–like Macrocycle," *J. Org. Chem.*, 52:4394–4397 (1987).

U.S. Application Serial No. 08/321,148 (Dkt. No. PHAY:033).

U.S. Application Serial No. 08/417,940 (Dkt. No. PHAY:036).

U.S. Application Serial No. 08/405,275 (Dkt. No. PHAY:043).

U.S. Application Serial No. 08/438,948 (Dkt. No. PHAY:050).

U.S. Application Serial No. 08/460,669 (Dkt. No. PHAY:052).

Wardle, "The surface of malignant and virus transformed cells," *Cell Surface Science in Medicine and Pathology*, Elsevier Science Publishing Co, Inc., New York, Ch. 19, pp. 552–561, 1985.

Verlhac & Gaudemer, "Water–soluble porphyrins and metalloporphyrins as photosensitizers in aerated aqueous solutions. I. Detection and determination of quantum yield of formation of singlet oxygen," *Nouveau Journal De Chimie*, 8:401–406, (1984).

Král & Sessler, "Molecular Recognition via Base–pairing and Phosphate Chelation. Ditopic and Tritopic Sapphyrin–based Receoptors for the Recognition and Transport of Nucleotide Monophosphates," *Tetrahedron*, 51(2):539–554, (1995).

Whitfield et al., "Differential reactivity of carbohydrate hytdroxyls in glycosylations. II. The likely role of intramolecular hydrogen bonding on glycosylation reactions. Galactosylation of nucleoside 5'–dydroxyls for the syntheses of novel potential anticancer agents," *Can. J. Chem.*, 72:2225–2238, (1994).

Schmidt, "Anomeric–oxygen activation for glycoside synthesis: the trichloroacetimidate method," *Advance in Carbohydrate Chemistry and Biochemistry*, 50:21–123, (1994).

STRUCTURES:

1. $R^4$ or $R^7$ = $CH_2CH_2CON(CH_2CH_2OH)_2$

2a. $R^4$ or $R^7$ = $CH_2CH_2CO_2H$     2b. $R^4$ or $R^7$ = $CH_2CH_2CO_2CH_3$

3. $R^4$ or $R^7$ = $CH_2CH_2CONH-C(CH_2OH)_3$

4. $R^4$ or $R^7$ = $CH_2CH_2CH_2O$ — [sugar]    R = Bz, Ac, H

4a. R = Ac   4b. R = Bz   4c. R = H

5. $R^4$ or $R^7$ = $CH_2CH_2CH_2OH$ $R^4$ or $R^7$ = $CH_2CH_2CONH$ — [sugar]    R = Ac, H 6a. R = Ac   6b. R = H STRUCTURES: 7a. $R^5$ = $CH_2CH_2CO_2H$
7b. $R^5$ = $CH_2CH_2CO_2CH_3$

STRUCTURE 8

STRUCTURE 9

STRUCTURE 10

STRUCTURE 11 R = Bz

STRUCTURE 12

STRUCTURE 13 R = Bz
STRUCTURE 14 R = H

STRUCTURE 15

STRUCTURE 16

STRUCTURE 17 R = Bz
STRUCTURE 18 R = H

STRUCTURE 19

STRUCTURE 20

STRUCTURE IV

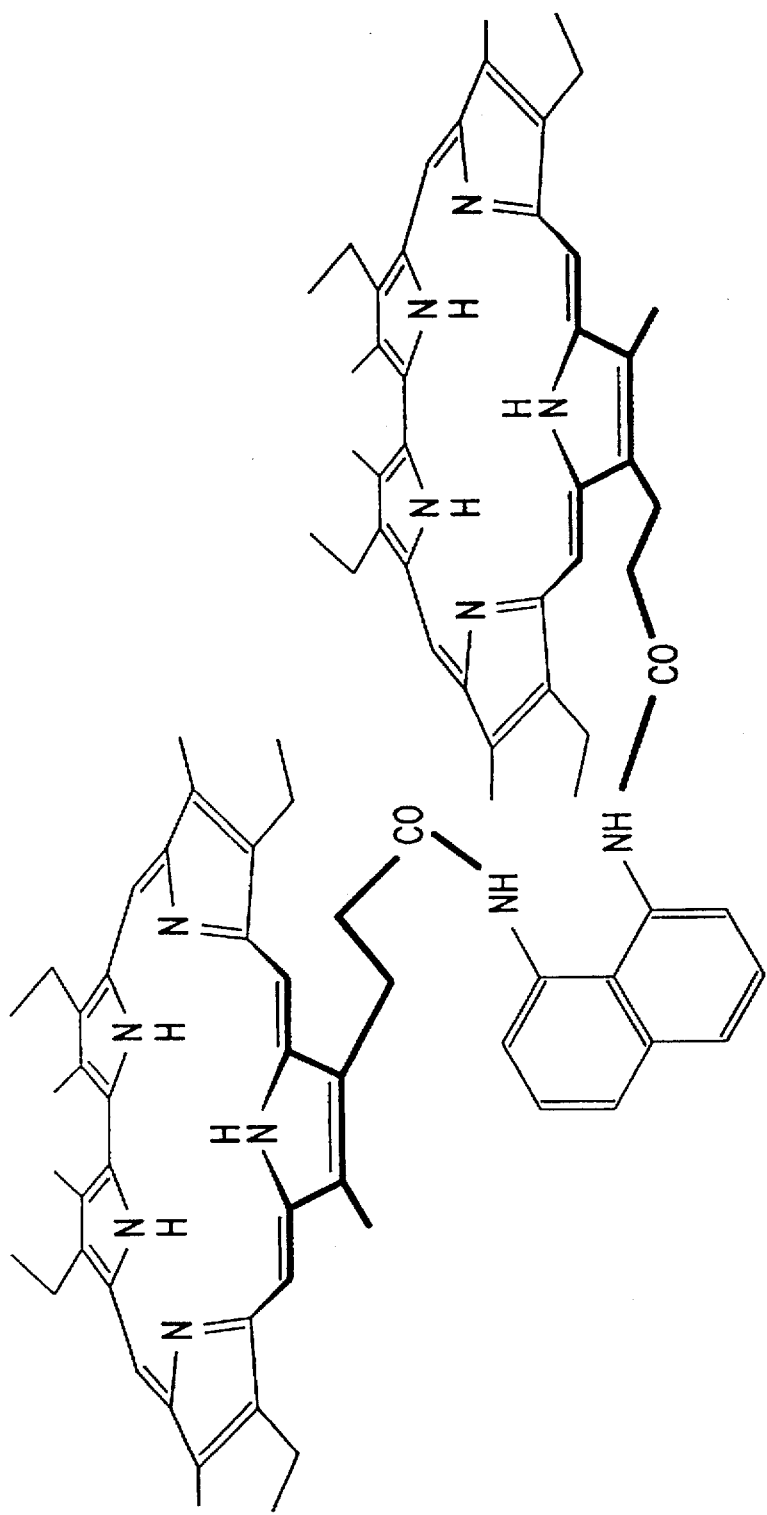
STRUCTURE 21 FIG.5B-1

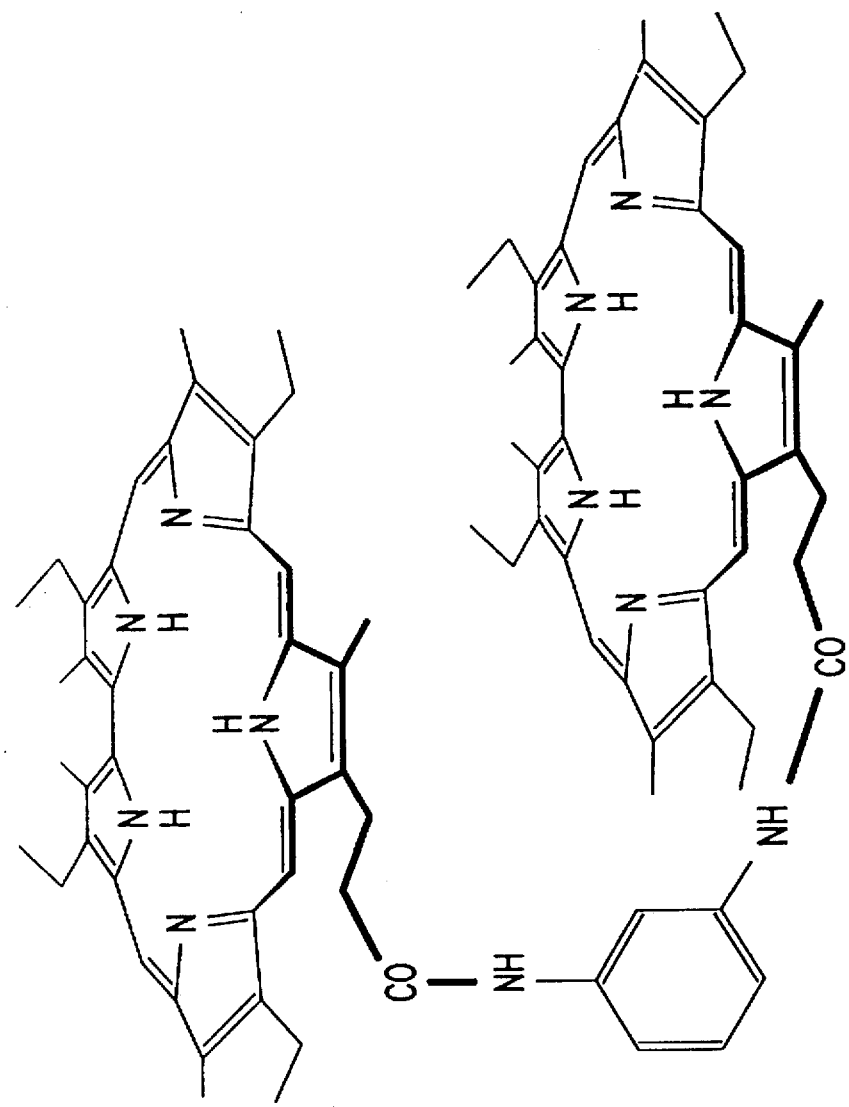
FIG.5B-2 STRUCTURE 22

STRUCTURE 23

STRUCTURE 24

STRUCTURE V

STRUCTURE 25

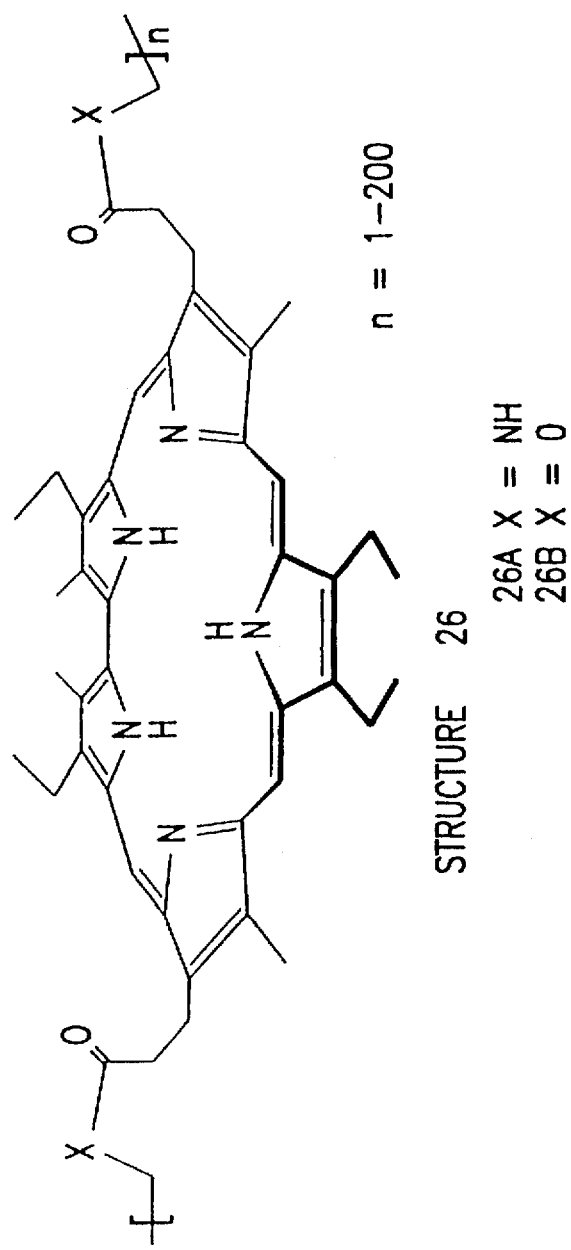

GENERAL STRUCTURE VII

STRUCTURE 31

STRUCTURE 32

STRUCTURE 33

STRUCTURE 34

STRUCTURE 39

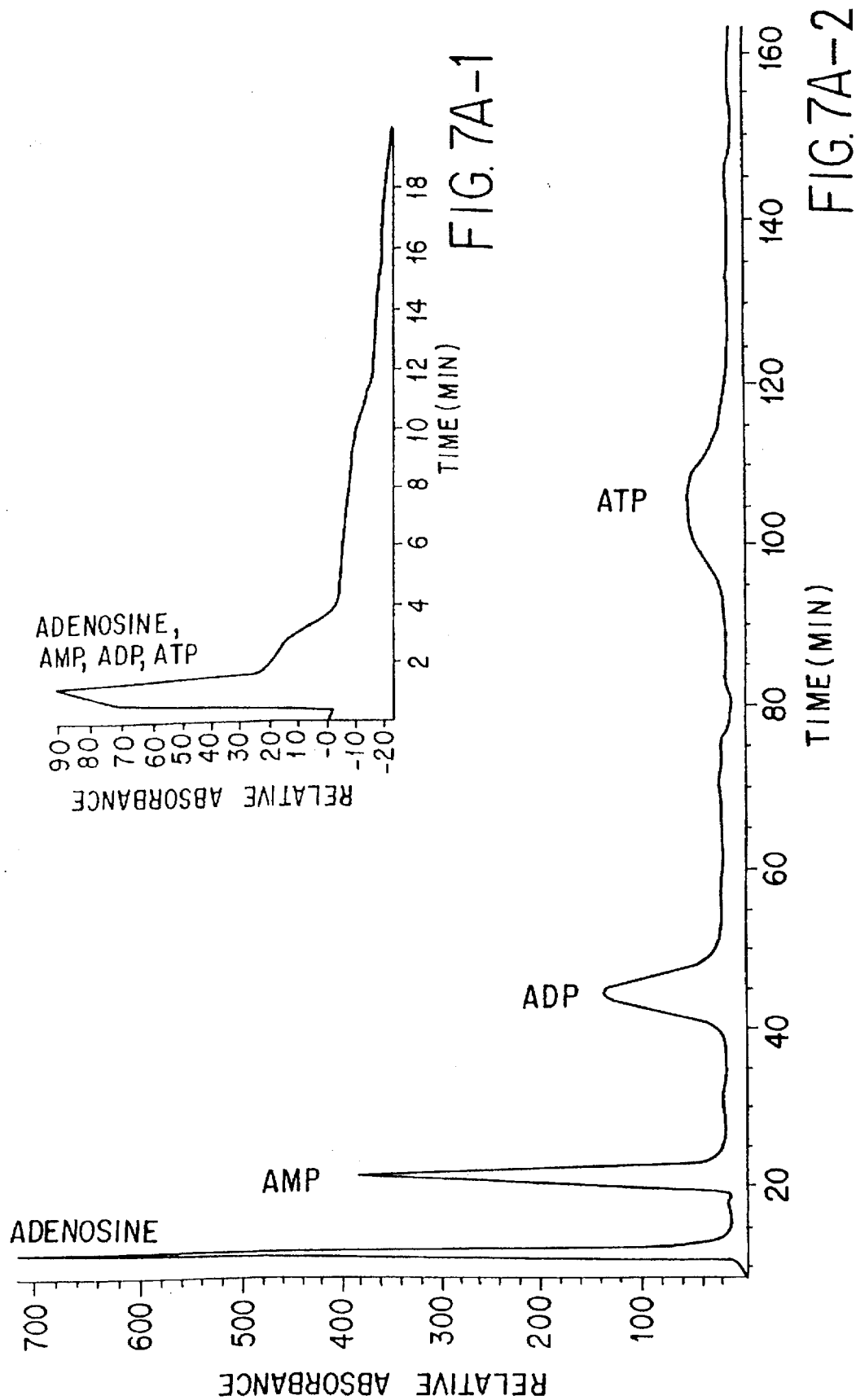

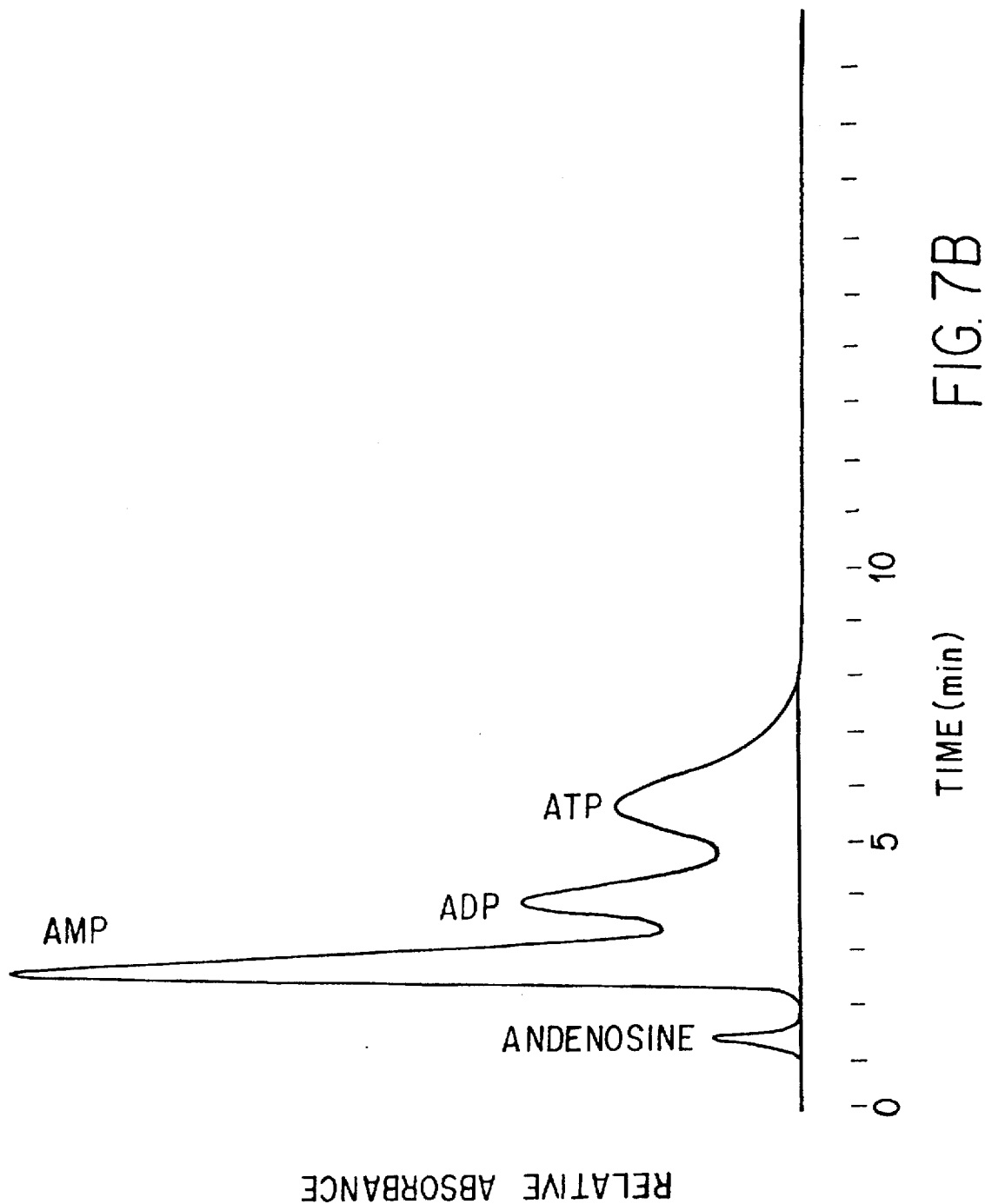

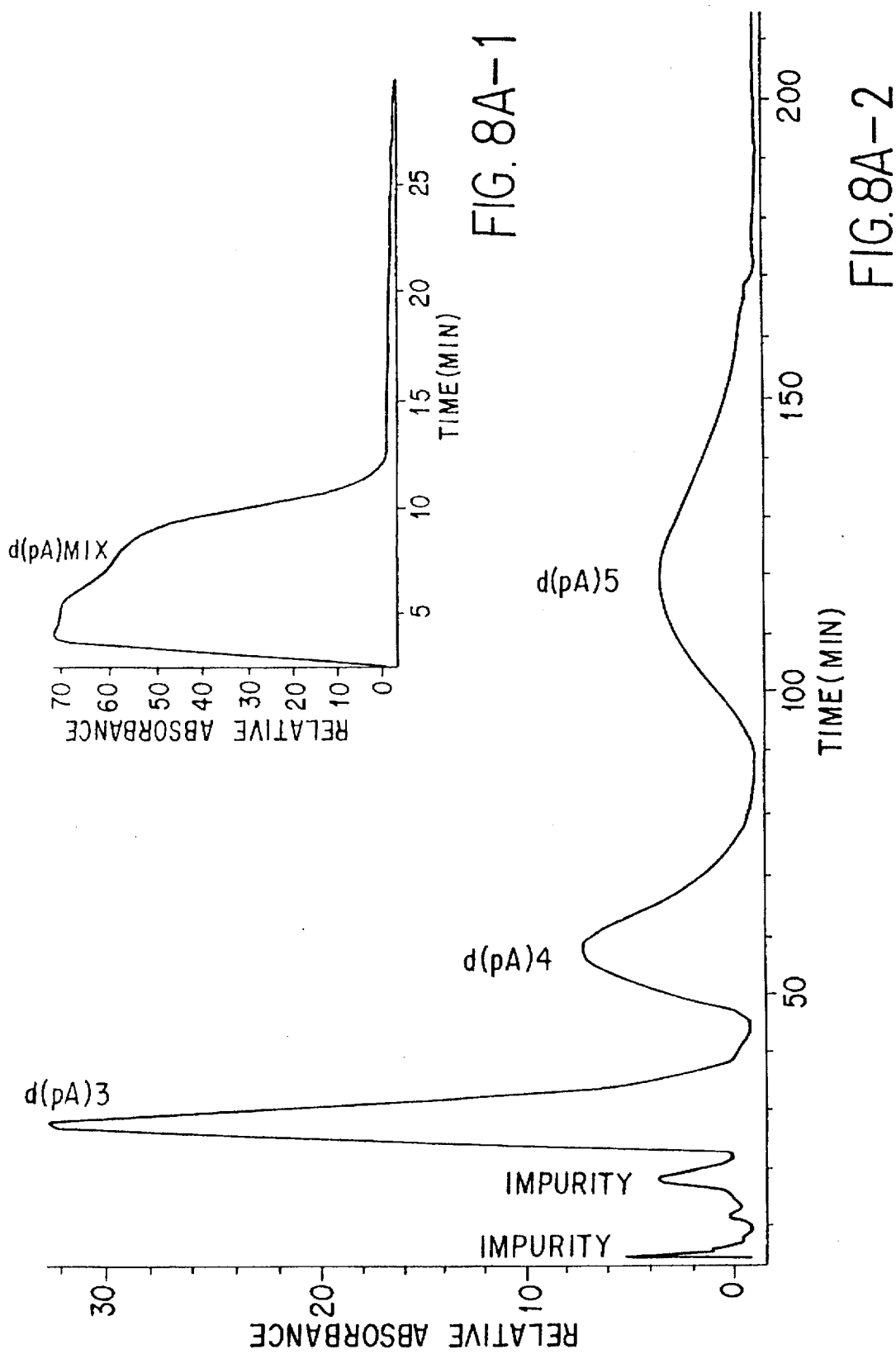

METHOD FOR SEPARATING MOLECULES

This application is a divisional application of copending application Ser. No. 08/424,288, filed Apr. 20, 1995 (and having a PCT filing date of Oct. 18, 1993), which is a continuation-in-part of application Ser. No. 07/964,607, filed Oct. 21, 1992 now U.S. Pat. No. 5,457,195.

BACKGROUND OF THE INVENTION

The entire texts of U.S. patent application Ser. No. 07/964,607, and U.S. patent application Ser. No. 08/015,208, filed Feb. 9, 1993 are specifically incorporated by reference herein without disclaimer. The government owns rights in the present invention pursuant to NIH grant AI 28845 and AI 33572.

1. Field of the Invention

The present invention relates to the field of macrocyclic expanded porphyrins and, more particularly, concerns novel sapphyrin derivatives, conjugates and polymers thereof and polymer-supported expanded porphyrins. Sapphyrin monomer derivatives of the invention include sapphyrin-sugar derivatives and other water soluble sapphyrins; sapphyrin-metal chelating derivatives; and sapphyrin nucleobase conjugates. Also disclosed are oligosapphyrins and polysapphyrins, including sapphyrin nucleobase oligomers and polymers; and silica gel, glass, resin and other polymer-supported expanded porphyrins such as rubyrin- and sapphyrin-containing chromatographic and electroploretic supports.

2. Description of the Related Art

Expanded porphyrins are large pyrrole-containing macrocyclic analogues of the porphyrins (e.g. porphine, structure I, FIG. 1). A number of expanded porphyrin systems are now known. However, only a few fully conjugated examples have been reported that contain more than four pyrrolic subunits, namely the smaragdyrins, sapphyrins, pentaphyrins, hexaphyrins, and superphthalocyanines[1] (Sessler & Burrel, 1991) Sapphyrin, in its generalized substituent-free form, is represented by structure II (FIG. 1). Structure III (FIG. 1) provides a generalized representation of β-substituted sapphyrins.

Sapphyrin, first discovered serendipitously by Woodward[2] is one of the more intriguing products to emerge from initial studies directed towards the synthesis of Vitamin $B_{12}$.[2,3] It is a 22 pi-electron pentapyrrolic macrocycle which exhibits an intense Soret-like band at about 450 nm ($CHCl_3$) along with weaker Q-type transitions in the 620 to 690 nm region. These optical properties, along with the presence of a large central cavity which serves for metal binding, renders sapphyrin useful for certain biomedical applications, including photodynamic therapy (PDT) and magnetic resonance imaging enhancement (MRI).

In addition to the above, certain expanded porphyrins, including especially those of the sapphyrin series, have been found to act as halide anion chelating agents in both solution and the solid state[4]. This finding, along with an appreciation, that the diprotonated form of 3,8,12,13,17,22-hexaethyl-2,7,18,23-tetramethylsapphyrin acts as an efficient carrier for the through-dichloromethane-membrane transport of nucleotide monophosphates, such as e.g. guanosine-5' monophosphate, and related entities at acidic pH[5], led the inventors to consider that the basic sapphyrin structure and related compounds such as the rubyrins, if suitably modified, could be used to bind, recognize, and transport phosphorylated entities at or near neutral pH. The inventors also envisioned that this same approach could be used for the improved chromatographic and electrophoretic separation of anionic species.

Unfortunately, all sapphyrins known at the time of this invention were known both to be essentially insoluble in water and also known to be ineffective as through membrane carriers for phosphate monoesters including those specifically that define the class of compounds known as nucleotides and nucleotide analogues[5]. These two deficiencies limited the potential utility of sapphyrins for any applications associated with their use at or near neutral pH and, more generally, any conditions involving partial or complete association with an aqueous environment.

In addition, the sapphyrins known prior to the present invention were all of such simple character in terms of peripheral substituents, such that only hydrogen, alkyl and carboxyl alkyl were known[1,6], that said systems, even if they were to demonstrate binding to nucleotides or nucleotides, would be expected to do so without any degree of specificity with regards the nature of the nucleic acid base ("nucleobase") attached to the phosphate core. Thus, at the time of this invention, it was considered that the development of a sapphyrin-derived species capable of binding, recognizing, and/or transporting a mononucleotide (or related entity) at or near neutral pH would represent a significant advance, especially if such system or systems could be made to achieve this binding, transport, or recognition in a nucleobase specific manner. This would be particularly valuable if this binding and recognition could be used as the basis for improved chromatographic and electrophoretic separations, such as in the analysis, detection and purification of oligonucleotides.

In addition to the above, it was recognized that the synthesis of one or more water soluble sapphyrins would represent a considerable advantage, not only in terms of phosphate entity recognition and transport, but also because it would allow for a detailed study of the basic binding phenomena in aqueous media. In the case where said water soluble sapphyrins were neutral in character, this would also give an important advantage in applications involving chromatographic and/or electrophetic separations.

A considerable number of ionic (e.g. phosphorylated) nucleotide analogues are known that exhibit antiviral activity in cell-free extracts and yet are inactive in vivo due to their inability to cross lipophilic cell membranes[7,8]. The anti-herpetic agent, acyclovir, is typical in that it enters the cell only in its uncharged nucleoside-like form. However, this compound is phosphorylated in the cytoplasm resulting in the active, ionic triphosphate species. In contrast, many other potential antivirals, including the anti-HIV agent, Xylo-G, are not phosphorylated intracellularly and are therefore largely or completely inactive[9]. If, however, the active monophosphorylated forms of these putative drugs could be transported into cells, it would be possible to fight viral infections with a large battery of otherwise inactive materials.

At present, no general set of nucleotide transport agents exists[10]. In early work, Tabushi was able to effect adenosine nucleotide transport using a lipophilic, diazabicyclooctane-derived, quaternary amine system[10a]. However, this same system failed to mediate the transport of guanosine 5'-monophosphate (GMP) or other guanosine-derived nucleotides. Since then, considerable effort has been devoted to the generalized problem of nucleic acid base ("nucleobase") recognition, and various binding systems have been reported. However, none are believed to have been applied to the problem of specific chromatographic and/or electrophoretic separations.

Currently known nucleotide binding systems include various acyclic, macrocyclic, and macrobicyclic polyaza systems[10a-10n]; nucleotide-binding bis-intercalands[10k]; guanidinium-based receptors[10f,10n]; and various rationally designed H-bonding receptors[10o-10u]. These latter H-bonding receptors have been shown to be effective for the chelation of neutral nucleobase and/or nucleoside derived substrates but, without exception, have all proved unsatisfactory for the important task of charged nucleotide recognition. Thus, despite intensive efforts in this field, there is currently no synthetic system capable of effecting the recognition, or through-membrane transport, of phosphate-bearing species such as anti-viral compounds. Furthermore, there are presently no rationally designed receptors which are "tunable" for the selective complexation of a given nucleobase-derived system.

Not surprisingly, the transport of larger polyphosphorylated compounds across cellular membranes also poses significant problems. The difficulties in transporting oligonucleotides across the plasma membrane and into mammalian cells is one of the factors currently limiting the successful application of antisense technology to human therapy. Further limitations may also result from the dynamics of oligonucleotide recognition, binding and functional inhibition which occurs intracellularly, subsequent to any import that does occur.

There is clearly, therefore, a major need for novel delivery systems to be developed. Compounds which would allow negatively-charged (anionic) structures, particularly phosphate-bearing compounds, including nucleotides and nucleotide derivatives such as anti-viral compounds and anti-sense oligonucleotides, to be transported across naturally lipophilic cellular membranes would represent an important scientific and medical advance.

It is also recognized that there is currently a considerable need for improved chemotherapeutic compounds which act upon DNA once inside a target cell to be designed. Since currently available chemotherapeutic agents have complex structures, or complicated modes of interaction with their targets that preclude systematic improvement, the development of a novel class of DNA binding compounds would open up new avenues for the design of improved therapeutics. In this regard, a class of compounds that can be modified in a number of different ways whilst maintaining their overall monomeric, or preferably polymeric, structure would be particularly advantageous. The same is true for compounds that can be activated by light, or other means, to produce singlet oxygen or hydroxyl radicals, once bound to DNA.

There is also a significant need for improved nucleotide- and nucleotide-binding compounds for use in connection with various laboratory techniques, both in clinical and research embodiments. For example, oligonucleotides are currently purified using polyacrylamide gel electrophoresis (PAGE) which is time-consuming, uses toxic materials, and is low-yielding.[23] Ion exchange columns can, on a limited basis, sometimes separate oligonucleotides containing 40 or fewer residues. However, this process is also generally unsuitable as, for example, severe conditions such as elution at pH 2.7, are often required.[29] The availability of a new column material, or improved functionalized glass capillaries, for use in chromatographically or electrophoretically separating nucleotides and oligonucleotides would thus represent a significant breakthrough in this area.

The foregoing and other considerations provided the present inventors with further impetus for the design and synthesis of the many different classes of improved sapphyrins, sapphyrin conjugates and polymers and polymer-supported expanded porphyrins embodied by the present invention.

SUMMARY OF THE INVENTION

The present invention addresses the above and several other shortcomings in the prior art through the synthesis of several novel monomeric and polymeric sapphyrin derivatives and other compounds and compositions based generally upon the sapphyrin molecule. Novel polymer-supported expanded porphyrins are also provided, including sapphyrin- and rubyrin-containing chromatographic and electrophoretic supports.

The invention therefore encompasses new sapphyrin derivatives and conjugates and polymers thereof. In a general and overall sense, included within the novel compounds of the invention are covalently modified sapphyrin monomers of the following general types: water soluble sapphyrins, sapphyrin-metal chelating derivatives and sapphyrin nucleobase conjugates. The invention also provides sapphyrin oligomers and polymers and polymer-supported expanded porphyrins including sapphyrin- and rubyrin-functionalized materials, such as silica gel, Merrifield resins and glass, for use as chromatographic and electrophoretic supports and columns. The oligomers, polymers and polymer-supported compositions will typically comprise sapphyrin or sapphyrin derivatives alone, or sapphyrin in combination with other units such as nucleobases. Complexes of sapphyrin-nucleobase polymers and polymer-supported expanded porphyrins with oligonucleotides and methods of using such compositions are also encompassed by the invention.

In general terms, sapphyrin derivatives of the present invention can be defined by the following general structure:

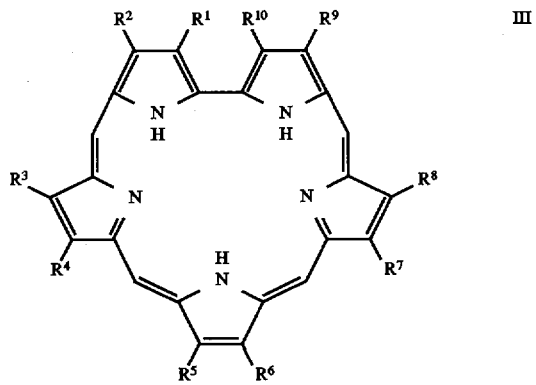

wherein each of $R^1-R^{10}$ is separately or collectively an H, alkyl, alkene, alkyne, halide, alkyl halide, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, aldehyde, ether, ketone, carboxylic acid, phosphate, phosphonate, sulfate, phosphate substituted alkyl, phosphonate substituted alkyl, or sulfate substituted alkyl, such that the total number of carbon atoms in each substituent R is less than or equal to 10.

One of the novel aspects of the foregoing structure is the fact that in the context of the present invention, at least one R group substituent of the foregoing general structure will be of the general formula X—B, wherein X is any sapphyrin compound and B is a substituent that 1) confers water solubility, 2) is a metal chelating compound, 3) is a nucleobase compound, 4) is a polymer or oligomer of sapphyrin or one of the foregoing sapphyrin derivatives or 5) is a polymeric matrix or solid support. As will be made clear hereinbelow, the term "polymeric matrix or solid support" includes common polymeric materials, such as polyacrylamide, polystyrene and the like; and other materials, such as silica gel, glass, Merrifield resins, agarose, clays and zeolites, that can be functionalized by those skilled in the art of chemical synthesis.

The novel aspects of the invention may most readily be denoted through the use of the structure X—$(CH_2)_n$—A—$(CH_2)_m$—B, wherein X is any sapphyrin macrocycle, and A is $CH_2$, O, S, NH or $NR^{11}$, wherein $R^{11}$ is alkyl, alkene, alkyne, halide, alkyl halide, hydroxyalkyl, glycol, polyglycol, thiol, alkyl thiol, substituted alkyl, phosphate, phosphonate, sulfate, phosphate substituted alkyl, phosphonate substituted alkyl, sulfate substituted alkyl, COO, CONH, CSNH, or $CONR^{11}$.

The B substituent will generally include any alkene alkyne, halide, alkyl halide, hydroxyalkyl, glycol, polyglycol, thiol, alkyl thiol, substituted alkyl, phosphate, phosphonate, sulfate, phosphate substituted alkyl, phosphonate substituted alkyl, sulfate substituted alkyl, hydroxyalkyl, aryl, silyl, siloxy, aminoaryl, amino, amidoaryl silyloxy, sugar, sugar derivative, polysaccharide, metal chelating group, nucleobase, modified nucleobase, oligonucleotide, sapphyrin, sapphyrin derivative, polymeric sapphyrin, alkylating agent, steroid, steroid derivative, amino acid, peptide or polypeptide, polymeric matrix or solid support (e.g., polyacrylamide, polystyrene, silica gel, Merrifield resins, glass, clays, zeolites); and n and m will be integers of less than or equal to 10 or are zero.

Certain particular embodiments of the invention relate to sapphyrin derivatives that are polyhydroxylated and therefore water-soluble. Water soluble sapphyrins are particularly desirable where one would like to exploit the various surprising properties of the sapphyrin macrocycle in connection with human or animal applications. The nature of the polyhydroxylation is not particularly critical to achieving water solubility of the sapphyrin derivative, so long as at least three or four hydroxyl groups per sapphyrin macrocycle are incorporated into the structure. The inventors have found that the introduction of at least 3 hydroxyl groups per macrocycle will be sufficient to achieve some degree of water solubility. This aspect of the invention is also important to the improved chromatographic and electrophoretic supports disclosed herein.

One means for introducing hydroxyl groups into the sapphyrin macrocycle structure is simply through the addition of alkyl substituents to the basic sapphyrin macrocycle unit, wherein the added substituents include one or more hydroxyl groups within their structures. Thus, exemplary polyhydroxylated sapphyrins will be those that are modified to include structures such as hydroxymethyl, hydroxyethyl, hydroxypropyl, hydroxybutyl, dihydroxyalkyl, trihydroxyalkyl, or the like, at one or more R positions of the basic sapphyrin structure shown above. Exemplary polyhydroxylated, water soluble sapphyrins are set forth in FIG. 2, and are denoted as structures 1 and 3.

An alternative means of achieving polyhydroxylation is through the addition of sugar moieties such as a saccharide, polysaccharide, saccharide derivative or aminosaccharide, to the sapphyrin macrocycle structure. In such cases, it has been found that the addition of a single saccharide molecule to a sapphyrin macrocycle will achieve a degree of water solubility. These structures are referred to broadly herein simply as sapphyrin-sugar compounds, conjugates or derivatives. The nature of the sugar is not critical to the achievement of water solubility, and a non-exhaustive, exemplary list of sugars contemplated to be useful in this regard is set forth in Table I. Of course, any sugar or modified sugar may be employed including sugars having additional phosphate, methyl or amino groups and the like. Moreover, the use of both D- and L-forms, as well as the $\alpha$ and $\beta$ forms is also contemplated. Particularly preferred are sugars such as glucose, galactose, galactosamine, glucosamine and mannose. Exemplary structures in this category are denoted as structures 4, 4a, 4b, 4c, 6, 6a and 6b of FIG. 2.

In other aspects, the invention concerns sapphyrin derivatives which incorporate a metal chelator or metal chelating moiety at the B position. It has been found that the addition of a chelator moiety confers exciting new properties to the sapphyrin macrocycle including, most notably, an ability to cleave DNA through an as yet unknown mechanism. This is particularly important because it allows one to prepare sapphyrin macrocycles that have the ability to both bind to, and cleave, DNA. Thus, not only will such molecules have clear in vitro uses, such as for DNA shearing or cleaving, but this also opens the door for in vivo uses. For example, it is quite possible that sapphyrin-chelator complexes will have the ability to bind to, and cleave, the DNA of blood-borne viruses.

Additionally, it is possible that the metal chelating sapphyrin structures will be useful in disrupting enzymatic action, by competing for requisite metal cofactors or by cleaving proteins. It is posited that due to their strong attraction for charged phosphate groups, the sapphyrins of the present invention will be particularly useful in selectively cleaving phosphorylated proteins, which are known to play a role in expression and activation of gene products including oncogene products. These structures may also be useful in an in vivo context through their introduction into cells, where they would be expected by the present inventors to effect cleavage of intracellular DNA or RNA. It may even be possible to effect a base or sequence specific cleavage through modification of the sapphyrin macrocycle structure, such as by substituent modification.

In particular embodiments relating to chelator conjugates, the sapphyrin-chelator derivative will include a metal chelating group such as 1,10-phenanthralene, EDTA, EGTA, DTPA, DOTA, crown ether, azacrown, catecholate or ethylene diamine. An exemplary structure is set forth as structure 8 of FIG. 3B, wherein the conjugated chelating group is EDTA. This particular molecule has been found to cleave DNA in a fashion that results in a "ladder" effect upon gel electrophoresis of the fragments that are generated.

In further embodiments, the present invention relates to what are referred to as sapphyrin-nucleobase conjugates. As used herein, the term "sapphyrin-nucleobase conjugate" is intended to refer broadly to any conjugate formed by the covalent conjugation of any sapphyrin macrocycle to any nucleobase. The sapphyrin-nucleobase conjugates may also be attached to a polymeric matrix or solid support, such as silica gel, glass, Merrifield resins, polyacrylamide, polystyrene, sepharose, agarose, clays, zeolites, and the like; to form a chromatography column or filter.

As used herein, the term "nucleobase" is intended to refer broadly to any moiety that includes within its structure a purine or pyrimidine, a nucleic acid, nucleoside, nucleotide, or any derivative of any of these. Thus, the term nucleobase includes adenine, cytosine, guanine, thymidine, uridine, inosine, or the like, bases, nucleotides or nucleosides, as well as any base, nucleotide or nucleoside derivative based upon these or related structures.

A particular example of useful nucleobases are the so-called antimetabolites, which are generally based upon the purine or pyrimidine structures. These compounds typically exert their biological activity as antimetabolites through competing for enzyme sites and thereby inhibiting vital metabolic pathways. However, in the context of the present invention, the inventors are employing the term "antimetabolite nucleobase" quite broadly to refer to any purine or pyrimidine-based molecule that will effect an anticellular, antiviral, antitumor, antiproliferative or antienzymatic effect, regardless of the underlying mechanism. Exemplary structures are shown in Table 2, including preferred conjugates such as purine or pyrimidine antimetabolites such as FU, AraC, AZT, ddI, ddC, xylo-GMP, Ara-AMP, PFA or LOMDP, and phosphorylated versions thereof.

In still further embodiments, the nucleobase component of sapphyrin-nucleobase conjugates will include a protected nucleobase having attached substituents that protect the nucleobase from inappropriate or undesirable chemical reaction. Examples include substituents such as 9-fluorenylmethyl carbonyl, benzyloxycarbonyl, 4-methoxyphenacyloxycarbonyl, t-butyl oxycarbonyl, 1-adamantyloxycarbonyl, benzoyl, N-triphenylmethyl, N-di-(4-methoxyphenyl)phenylmethyl, and the like.

It is contemplated that sapphyrin-nucleobase conjugates will have a wide variety of applications, ranging from their use as agents for selectively delivering an associated, biologically active nucleobase to a particular body, or even subcellular, locale to their use in laboratory protocols concerned with nucleotides or oligonucleotides. For example, in the case of antimetabolite nucleobases, it is contemplated that the sapphyrin-nucleobase conjugates will act to deliver the antimetabolite to subcellular sites through the DNA binding activity of the sapphyrin portion of the conjugate.

Furthermore, and perhaps more importantly, it is recognized that many, many nucleobase antimetabolites can not be readily employed in therapy due to the fact that their charged nature inhibits their uptake by target cells, or otherwise inhibits or suppresses their unencumbered movement across biological membranes. Typically, this shortcoming is due to the presence of charged structures such as phosphates, phosphonates, sulfates or sulfonates on the nucleobase which, due to their charged nature, prevents or inhibits their crossing of a biological membrane. It is proposed that sapphyrins of the present inventions can be employed as transport agents for carrying such nucleobases across membranes, (whether the nucleobase is directly conjugated to the macrocycle or simply complexed with it).

Generally speaking, in the context of sapphyrin-nucleobase constructs designed for drug delivery it will usually be the case that one will employ only one nucleobase-containing substituent for each sapphyrin macrocycle, however this is in no way a limitation upon the invention. For example, sapphyrin-nucleobase conjugates of the present invention may have any number of nucleobases or nucleobase oligomers or polymers attached.

The foregoing can be most readily appreciated through consideration of other embodiments and utilities that are contemplated by the inventors. For example, it is has been surprisingly discovered by the inventors that sapphyrin-nucleobases which include a selected nucleotide nucleobase conjugate will serve to selectively bind, through hydrogen bonding interactions, the complementary nucleotide. Thus, a sapphyrin-nucleobase conjugate such as sapphyrin-adenine will selectively bind thymidine, presumably through a hydrogen bonding of the two nucleotides that is stabilized through the interaction of the charged phosphate groups of the hydrogen bonded nucleotide with the macrocycle structure. Such structures will likely have a wide variety of applications, such as intracellular carriers for nucleobases that are hydrogen bonded rather than being covalently attached. Furthermore, as discussed in more detail below, it is contemplated that polymers of sapphyrin-nucleobase conjugates can be employed to carry hydrogen bonded oligo- or poly-nucleotides into target cells through complementarity with the sequence of bases "encoded" on the sapphyrin-nucleobase polymer.

The foregoing general structure could be exemplified by the formulas:

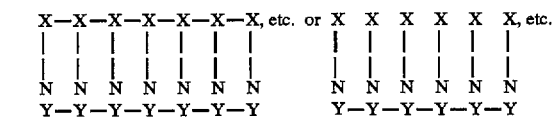

wherein X is the sapphyrin macrocycle, N is the conjugated nucleobase structure, and Y is the hydrogen bonded poly- or oligonucleotide.

Alternatively, it is contemplated that sapphyrins of the present invention may serve as a carrier for polymers of nucleobases, wherein the nucleobase polymers are attached covalently to the sapphyrin macrocycle, such as might be exemplified through the structural designation:

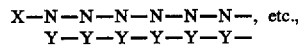

wherein X is a single sapphyrin macrocycle, and N is a selected oligomeric or polymeric nucleotide or other nucleobase, and Y is a hydrogen bonded poly- or oligonucleotide.

Such structures would be useful in a number of contexts, including acting as a specific carrier for complementary nucleotides. The complementary nucleotides could be structures such as antisense molecules, including C-5 propyne-containing antisense oligos, designed to inhibit the transcription, translation or both, of a given gene or construct. Alternatively, they could be coding or "sense" strands of DNA which encode an entire gene, a functional protein domain, or any polypeptide, peptide, or fragment thereof. Such constructs may be used in in vitro molecular biological embodiments or in gene transfer protocols in which the DNA is intended to act as a template for the production of proteins or peptides such as normally-functional or therapeutically-important proteins and peptides.

Chemically speaking, any number of nucleobase structures can be attached to the sapphyrin macrocycle. The ultimate number of such residues that are attached will, of course, depend upon the application. Where one intends to employ such a structure to carry complementary nucleotides, one may well desire to employ a structure having a polymer of at least 10 or so bases attached. However, for other applications, such as for intracellular delivery of the nucleobase or other charged compounds of non-polymeric size, it may be convenient to design and employ sapphyrin-nucleobase constructs employing from one to three nucleobases per single macrocycle. Moreover, the nature of the intended use will dictate the number of attachment points there are on the sapphyrin macrocycle for attaching nucleobase moieties. Thus, will it may typically be the case that a single attachment site will suffice for most applications, for certain particular applications those of skill may find it particularly advantageous to attach various nucleobases at various of the subcomponents of the macrocycle.

Referring to structure III and the general formula presented above, it is contemplated that preferred sapphyrin nucleobase derivatives will be those in which n is an integer of less than or equal to 6 or zero, and m is an integer of less than or equal to 4 or zero. A number of the simpler sapphyrin-nucleobase conjugates contemplated by the inventors are set forth in FIGS. 4A-1 through 4A-6 and 4B-1 through 4B-4, and serve as simple examples of the overall concept. Thus, for example, one may wish to refer to structures 9, 10, 11, 12, 13, 14, 15, 16, 17, 18, 19, and 20 of FIGS. 4A-1 through 4A-6 and FIGS. 4B-1 through 4B-4 as representatives of this class of novel sapphyrin derivatives.

As mentioned above, a particular aspect of the present invention involves the realization that novel sapphyrin structures may be prepared through the construction of sapphyrin polymers or oligomers. As used herein, the terms "sapphyrin polymer" or "polysapphyrin" are intended to refer to any compound which includes at least two sapphyrin macrocycles joined covalently. The terms "oligomer" and "polymer" are generally understood to be overlapping in terms of defining a given length. However, it will still be appreciated that a "sapphyrin oligomer" or "oligosapphyrin" refers to sapphyrin-containing structures having about 2 or 3, and more preferably, about 10, 15, 20 or 30 sapphyrin units/ molecule, up to an including about 40 or 50 units. On the other hand, "sapphyrin polymers" or "polysapphyrins" are sapphyrin-containing structures which generally have upwards of about 40 or 50 sapphyrin units, up to an including about 80, 100 or 150 sapphyrin units, or even up to about 200 sapphyrin units or even more.

The sapphyrin oligomers and polymers of the invention also include sapphyrin dimers and trimers. Examples of such sapphyrin dimer and trimer structures include, but are not limited to, those represented by the dimer structures 21, 22 and 23 of FIGS. 5B-1 through 5B-3 and the trimer structure 24 of FIG. 5B-4. The various sapphyrin oligomers and polymers encompassed by the present invention are represented by, for example, structures 26 and 27 of FIGS. 5C-3i and 5C-3ii in which n, the number of individual sapphyrin derivative units, may be about 5, 10, 20, 30 or 40, for sapphyrin oligomers, and about 50, 75, 100, 150 or about 200 or so for sapphyrin polymers.

In still further embodiments, the present invention encompasses polymer-supported expanded porphyrin compositions and methods of using such compositions. As used herein, "a polymer-supported expanded porphyrin" is an expanded porphyrin or derivative or conjugate thereof which has been covalently joined to a polymeric or solid support. "Polymeric or solid support matrices" include not only such common polymers as polyacrylamide and polystyrene, but also materials such as silica gel, Merrifield resins, glass, sepharose, agarose, clays, zeolites, and the like, that can be functionalized to allow the formation of an expanded porphyrin bonded to a support matrix. Virtually any expanded porphyrin, including sapphyrins, rubyrins and even texaphyrins, may be joined to a polymeric or solid support matrix in accordance with this aspect of the invention. However, in preferred embodiments it is contemplated that one would use an expanded porphyrin capable of binding anions, and more preferably, one capable of phosphate chelation, as the porphyrin part of the polymer-supported expanded porphyrin. As such, the use of expanded porphyrins of the rubyrin and sapphyrin classes will generally be preferred.

The synthesis of rubyrin and derivatives thereof is described in detail in U.S. patent application Ser. No. 08/015,208, incorporated herein by reference. Polymer-supported rubyrins prepared in accordance with the present invention may be further defined as comprising a rubyrin derivative in accordance with Structure 28, 29 or 30 of FIGS. 5D-1, wherein $A_1$ and $A_2$ may be nitrogen, oxygen or sulphur and one of the substituents $R_1$–$R_6$ or $X_1$–$X_4$ will be derivitized to form the $(CH_2)_n$—A—$(CH_2)_m$—B structure, wherein B includes the polymeric support. The other of the substituents $R_1$–$R_6$ and $X_1$–$X_4$ in structures 28, 29 and 30 may be separately and independently H, alkyl, aryl, amino, hydroxyl, alkoxy, carboxyl, carboxamide, ester, amide, sulfonato, hydroxy substituted alkyl, alkoxyl substituted alkyl, carboxyl substituted alkyl, amino substituted alkyl, sulfonato substituted alkyl, ester substituted alkyl, amide substituted alkyl, substituted aryl, substituted alkyl, substituted ester, substituted ether, substituted amide.

In other preferred embodiments, the polymer-supported expanded porphyrin will be a polymer-supported sapphyrin comprising a sapphyrin unit, such as any of those disclosed herein, or a derivative, conjugate or polymer thereof. Exemplary polymer-supported sapphyrin structures are represented by structures 31, 32, 33, 34, 35, 36, 37 and 38 of FIGS. 5D-3 through 5D-10. However, given the synthetic methodology described herein, one of skill in the art will be able to prepare a wide range of sapphyrin-substituted polymeric supports, such as silica gel, glass and a variety of other supports, all of which will be understood to fall within the scope of the claimed invention.

With reference to the general formula of the invention described above and represented in structure III, the polymer-supported sapphyrins may also be defined as a sapphyrin derivative wherein at least one of $R^1$–$R^{10}$ is of the formula $(CH_2)_n$—A—$(CH_2)_m$—B, wherein B comprises the polymeric or solid support matrix. In preferred embodiments, the B substituent will also comprise an aryl, silyl, siloxy, aminoaryl, amino, amidoaryl, or silyloxy group, which will be located between the polymeric or solid support matrix and the expanded porphyrin and hence will act as a linking unit. In certain defined cases, the linkage between the expanded porphyrin and the polymeric or solid support matrix may be defined as matrix —$(CH_2)_3$—$(CH_2)_2$—$SiR_2$—O—B; $(CH_2)_3$—$Si(R)_2O$—B; $(CH_3)_2$—$Si(CH_3)_2$O—B. Exemplary polymer-supported expanded porphyrins are set forth in FIGS. 5D-1 through 5D-10 and include the rubyrin-supported structures of 28–30 in addition to the sapphyrin structures of 31–38.

Many types of polymeric or solid support matrices are contemplated to be of use as supporting matrices in connection with the present invention and as represented in any of structures 28–38. These include, for example, silica-based compounds such as silica gel and various forms of glass, including controlled pore glass; organic polymers such as Merrifield resins; and other compositions such as agarose, sepharose, polyacrylamide, polystyrene, clays, zeolites, and the like.

The polymeric or solid support matrix which forms the supporting part of the polymer-supported expanded porphyrin will generally be chosen according to the intended function and use of the resultant composition. For example, silica gel may be used to prepare bonded, sapphyrin-substituted silica gels for formulation into columns for use in medium to high pressure applications, such as in analytical and preparative HPLC separation technology. Alternatively, for low pressure applications, organic polymer-based expanded porphyrins may be prepared, such as rubyrin- or sapphyrin-substituted Merrifield resins. Also, a glass support such as a glass capillary tube, may be employed to prepare a glass-supported expanded porphyrin for use, e.g., in analytical capillary electrophoresis (CE).

The range of polymer-supported expanded porphyrins contemplated by the present inventors, and described herein, extends to second and third generation compositions designed to separate negatively-charged, phosphorylated species based upon further specific binding modes, in addition to the phosphate recognition provided by the expanded porphyrin moiety. One particular example concerns polymer-supported expanded porphyrins which further comprise long chain alkyl groups, such as, those of the formula $CH_3-(CH_2)_nSi(CH_3)_n$, where n=1–20, such as, e.g., $CH_3(CH_2)_7$, $CH_3(CH_2)_{11}$ or $CH_3(CH_2)_{17}$, and also groups such as $C_6H_5CONH$, phenyl, naphthyl, substituted naphthyl, and the like, to impart hydrophobic and $\pi$—$\pi$ interaction separation capacity to the modified solid support. A second example concerns the use of polymer-supported expanded porphyrin constructs which also comprise nucleobase structures and thus allow separation of nucleobase-containing compounds on the basis of specific base-pairing interactions.

The further modified polymer-supported expanded porphyrins may be constructed by modifying either the appended expanded porphyrin moiety or the polymeric or solid support matrix itself. For example, in the case of expanded porphyrin-nucleobase columns, sapphyrin- or rubyrin-nucleobase conjugates may be used in the initial synthesis, or alternatively, the nucleobase units may be later appended onto available groups of the expanded porphyrin or onto available groups of the solid support itself. Where the addition of long chain alkyl groups is desired, it is contemplated that such groups will generally be introduced onto the surface of the polymeric or solid support matrix, although the invention is not limited to this mode of addition.

As with the sapphyrin-nucleobase conjugates described above, the polymer-supported expanded porphyrin-nucleobase constructs may contain a wide variety of nucleobase compounds. The choice of compound will be tailored to suit the intended function of the solid support, such as, to bind to a specific nucleobase-containing compound which one desires to purify, remove or otherwise separate from a mixture of compounds. The nucleobase-containing group, whether bonded to the expanded porphyrin or to the support matrix, may therefore comprise any purine or pyrimidine base including adenine, cytosine, guanine, thymidine, uridine and inosine, or any analog or derivative thereof, including antimetabolite nucleobases, nucleobase derivatives shown in Table 2, and even protected nucleobases.

The expanded porphyrin-nucleobase solid support matrices may also have appended nucleosides, nucleotides and oligonucleotides, for example, oligonucleotides comprising between two and about 10 nucleobase units. Such polymer-supported sapphyrin nucleobase compounds may be based upon any of the structures 28 through 38 of FIGS. 5D-1 through 5D-10. Constructs bearing a selected nucleotide or oligonucleotide may be formulated into columns, filters or other solid materials such as capillary tubes, and used to selectively bind compounds which include the complementary nucleotide or oligo or poly-nucleotides containing substantially complementary sequences. As used herein, a substantially complementary sequence is one which the nucleotides generally base pair with the complementary nucleotide and in which there are very few base pair mismatches.

Accordingly, the present invention also provides methods for using the polymer-supported expanded porphyrins described above in separating a first molecule from a mixture of at least two molecules. In the present sense, the term "molecule" is being used for simplicity to refer to both molecular and atomic structures and thus encompasses species such as $Cl^-$, $Br^-$, and $I^-$. The columns, capillary tubes, filters and the like, of the invention are contemplated to be of most use in separating negatively-charged or anionic species which include a phosphate, phosphonate, phosphate ester, arsenate, arsenate ester, sulfate, or sulfonate moiety within their structure. However, such constructs, and particularly the polymer-supported rubyrins and sapphryins, may also be used for separating other molecular or atomic anions, including halide or pseudohalide anions like azide or cyanide that contain a negatively-polarized portion within overall their structure.

To separate a first molecule from a mixture of at least two molecules in accordance with the invention, one would generally first prepare a matrix support with an expanded porphyrin and then contact the matrix support with the mixture, thereby separating the first molecule. In more detail, this generally entails binding the mixture containing the molecules or species to be separated to a matrix- or polymer-supported expanded porphyrin, such as a column, capillary tube, filter or such like, and then subsequently removing, or eluting, the bound species in such as way as to result in the formation of distinct fractions containing molecules which have been separated from each other.

The phrases "separated" and "purified" in this context are intended to mean separated away from, and purified relative to, the degree of purity of an individual molecule, atom or species in the original composition. Although the methods of the invention generally result in high resolution separation of, e.g., phosphorylated species such as nucleotides and oligonucleotides, there is no requirement that such high degrees of purity always be achieved and separation methods which result in less substantially separated species also have utility and are thus encompassed by the claimed invention.

These methods for separating or purifying negatively-charged species are generally encompassed by the terms "chromatographic or electrophoretic separation methods". The chromatographic methods are those using columns, such as HPLC columns, whereas the electrophoretic separation methods are exemplified by those using capillary tubes. Chromatographic and electrophoretic separation techniques are well known in the art and any such method may be employed in connection with the invention simply by preparing a polymer-supported expanded porphyrin comprising an expanded porphyrin or derivative joined to a polymeric or solid support matrix, such as silica gel, Merrifield resin, glass or any other suitable matrix, and using this as the column, filter or capillary tube central to the separation technique.

In separating negatively-charged species in accordance with the invention, it is contemplated that one would generally first formulate the composition containing the negatively-charged species to be separated into a solution. One would then contact the polymer-supported expanded porphyrin with the solution under conditions effective to allow binding of the negatively-charged species to the solid support. This is straightforward and may be achieved simply by passing the solution over the solid material with or without the use of pressure or an electrostatic field. The negatively-charged species will, in the simplest case, bind specifically to the expanded porphyrin moiety. Where polymer-supported expanded porphyrins bearing other groups, such as long chain alkyl groups, nucleobases, or aromatic residues for $\pi$—$\pi$ stacking interactions with nucleobases are used, other portions of the negatively-charged compounds, such as hydrophobic portions or purine and pyrimidine nucleobase substituents, will also likely specifically bind to these additional functional groups or interact with the sapphyrin ring.

Suitable conditions effective to allow binding of the species to the solid support will be chosen based upon considerations such as the number and type of the particular species to be separated, the purity of the resultant compositions desired, the type of expanded porphyrin, other functional groups appended to the expanded porphyrin or solid support matrix, and the like. At this stage, the solid support may be washed with the same or other buffers of chosen stringency and for varying periods of time to remove any non-specifically bound species from the solid support such separations in the case of chromatographic applications would be useful both for analysis and purification procedures. In the case of capillary electrophotesis, however, they would be likely to be use only for analysis.

The polymer-supported expanded porphyrin with the bound species should next be treated to remove the bound species which may then be collected in a more separate and purified form than when they were applied, for example, in distinct fractions. This process will generally be achieved by washing the solid support with a second solution effective to detach the bound negatively-charged species, i.e., a solution effective to disrupt the specific binding between the species and the expanded porphyrin or other functional groups of the support. Such separations, in the case of chromatographic applications would be useful both for analysis and purification procedures. In the case of capillary electrophotesis, however, they would be likely to be useful only for analysis.

The second solution will be distinct from that first used and, again, will be chosen based upon the particular application. It may, for example, have a different ionic strength, hydrophobicity or pH to the first solution and may contain different concentrations of salt or other chaotropic agents as desired. This removal process may be termed "elution" and the eluted material will generally be collected in relatively small fractions, such as in 1 to 2 ml fractions, and preferably in fractions of about 1 ml or smaller, so that the fractions contain one or more detached negatively-charged species which have been separated or purified away from the total number of species in the starting composition. Alternatively, for analysis applications, the fractions could be much smaller, i.e. $\leq 10$ μl, and used only as a means of assessing by, e.g. optical absorbance, refractive index, or mass spectral fragmentation, the composition of a given fraction. From such an analysis one would then, in the usual way of the art obtain a profile of the purity and composition of the original solution.

Any of the polymer-supported expanded porphyrin derivatives described above may be used as a separating apparatus in this regard. For example, those comprising a sapphyrin or rubyrin derivative and those including one or more sapphyrin- or rubyrin-nucleobase conjugates may be employed, as may supports comprising long chain alkyl groups and oligonucleotides. The separating apparatus may use, for example, silica gel, Merrifield resins or glass or support matrices and may be prepared in virtually any solid form including columns, filters and tubes. Their use in analytical and preparative modes in both research and clinical laboratories is envisioned.

It is contemplated that these novel polymer-supported expanded porphyrins will be found to be particularly useful in separating compounds which have phosphate groups or phosphate esters within their structure. This includes separating or purifying purine- and pyrimidine-containing compounds, including nucleotides oligonucleotides, gene fragments, nucleobase analogs and derivatives such as antimetabolite purines and pyrimidines, e.g., AZT phosphate, dideoxycytidine phosphate, and other prodrugs used in the treatment of viral infections including HIV. The use of the methods and compositions of the invention in clinical analyses to distinguish active phosphorylated nucleotide analogs from naturally occurring phosphorylated products, such as AMP or GMP, is a further particular utility envisioned by the inventors.

Organophosphorus compounds, particularly pesticides, herbicides, fungicides and even chemical warfare agents may also be separated in the manner of the invention. For example, using polymer-supported expanded porphyrin constructs is envisioned to be of use in removing various such undesirable compounds from contaminated solutions, e.g., in waste-removal and treatment regimens.

As disclosed herein, nucleotide mono-, di- and triphosphates may be advantageously separated from each other using polymer-supported sapphyrins, as may mononucleotides, di-nucleotides and various length oligonucleotides, such as oligo probes and primers. The separation of larger polynucleotides, up to and including gene fragments, genes, and antisense constructs is also encompassed by the present invention. The sequence-specific purification of nucleotide-containing constructs is also envisioned, whereby specific oligo or polynucleotides, whether DNA or RNA species, may be obtained by employing second or third generation polymer-supported expanded porphyrins bearing appended oligos with specific sequences. This allows the separation of nucleotides and oligonucleotides not only on the basis of charge and length but also on the basis of nucleic acid type.

In yet still further embodiments, the invention concerns compositions which are composed of a sapphyrin derivative in accordance with any one of the embodiments discussed above, including the polymer-supported versions, complexed to a second compound, wherein the second compound includes within its structure a negatively charged phosphate, phosphonate, sulfate, or sulfonate moiety. More particularly, the second compound will be one that will bind to the sapphyrin by means of its negative charge, afforded by a sulfate, sulfonate, an ester of sulfate or sulfonate, a phosphate, a phosphate mono or diester, a phosphonate or phosphonate ester moiety.

In particular embodiments, the second compound will include a purine or pyrimidine, or an analog of either, within its structure. Exemplary structures include purine or pyrimidine antimetabolites such as FU, AraC, AZT, ddI, xylo-GMP, Ara-AMP, PFA or LOMDP. In other embodiments, the second compound of the composition will simply be DNA or RNA.

In still further embodiments, the invention concerns a method for forming a complex between a sapphyrin derivative and a second compound which includes within its structure a negatively charged phosphate, phosphonate, sulfate or sulfonate moiety, wherein the method involves preparing a sapphyrin derivative as described above, including the polymer-supported forms such as silica-, Merrifield resin-, glass- and organic polymer-supported expanded porphyrins; obtaining the second compound; and contacting the sapphyrin derivative with the second compound under conditions effective to allow the formation of a complex between the sapphyrin derivative and the second compound.

It will be appreciated by those of skill in the art that the invention is also generally applicable to the introduction of a sapphyrin molecule, alone or complexed with a second molecule, into a cell, including cells contained within an organism and cells maintained in vitro. This may be employed as a means, for example, of successfully introducing the second compound (typically a charged compound) into the cell. An example might be introduction of a complex which includes an antimetabolic or antienzymatic compound such as an antiviral antimetabolic or antienzymatic compound, which one desires to introduce into a virally infected target cell. Another example would be the introduction of an antimetabolic or antienzymatic antitumor or antiproliferative compound that is introduced into a targeted tumor or proliferating cell. A further example would be contacting a cell with a photoactivatable sapphyrin derivative. of course, it is contemplated that the target cell may be located within an animal or human patient, in which case the complex will be formulated into a medicament and an effective amount of the medicament will then be administered to the patient.

Generally speaking, it is contemplated by the inventors that useful medicaments and pharmaceutical compositions of the present invention will include the selected sapphyrin derivative (which preferably incorporates a water soluble sapphyrin macrocycle) in a convenient amount that is diluted in a physiologically acceptable buffer, such as phosphate buffered saline. The route of administration and ultimate amount of material that is administered to the patient or animal under such circumstances will depend upon the intended application and will be apparent to those of skill in the art in light of the examples which follow. Preferred routes of administration will typically include parenteral or topical routes.

In still further embodiments, the invention concerns a method of cleaving DNA comprising preparing a sapphyrin-chelator derivative and contacting DNA with said sapphyrin under conditions effective to promote cleavage of the DNA.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Throughout the figures and text of the present specification, where sapphyrins are concerned, roman numerals are employed to indicate a general sapphyrin structure for which alternative substituents are possible, and arabic numbers are employed when referring to specific and exemplary sapphyrin compounds. However, two points should be noted. First, in regard to the expanded porphyrins of the rubyrin class, structures 28, 29 and 30 of FIG. 5D-1 are general rubyrin structures for which alternative substituents are possible, as detailed in the specification and brief description of the drawings hereinbelow. Second, in the polymer- or matrix-supported expanded porphyrins of structures 28–38, in FIGS. 5D-1 through 5D-10, the polymer or matrix may always be any one of those described throughout the present application.

In Structure III: $R^1$–$R^{10}$ may be H, alkyl, alkene, alkyne, halide, alkyl halide, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, aldehyde, ether, ketone, carboxylic acid, phosphate, phosphonate, sulfate, phosphate substituted alkyl, phosphonate substituted alkyl, or sulfate substituted alkyl; such that the total number of carbon atoms in each substituent, R, is less than or equal to 10. The novelty of these sapphyrin derivatives lies in the fact that at least one of the R ($R^1$–$R^{10}$) will be of the formula $(CH_2)_n$—A—$(CH_2)_m$—B; wherein A may be $CH_2$, O, S, NH or $NR^{11}$, wherein $R^{11}$ is alkyl, alkene, alkyne, halide, alkyl halide, hydroxyalkyl, glycol, polyglycol, thiol, alkyl thiol, substituted alkyl, phosphate, phosphonate, sulfate, phosphate substituted alkyl, phosphonate substituted alkyl, sulfate substituted alkyl, COO, CONH, CSNH, $CONR^{11}$; and wherein B may be alkene, alkyne, halide, alkyl halide, hydroxyalkyl, glycol, polyglycol, thiol, alkyl thiol, substituted alkyl, phosphate, phosphonate, sulfate, phosphate substituted alkyl, phosphonate substituted alkyl, sulfate substituted alkyl, hydroxyalkyl, aryl, silyl, siloxy, aminoaryl, amino, amino aryl silyloxy, amidoaryl, silyloxy, sugar, sugar derivative, polysaccharide, metal chelating group, nucleobase, modified nucleobase, oligonucleotide, sapphyrin, sapphyrin derivative, polymeric sapphyrin, polymeric matrix, solid support, alkylating agent, steroid, steroid derivative, amino acid, peptide or polypeptide, and n and m are integers of less than or equal to 10 or zero.

Figure 2:
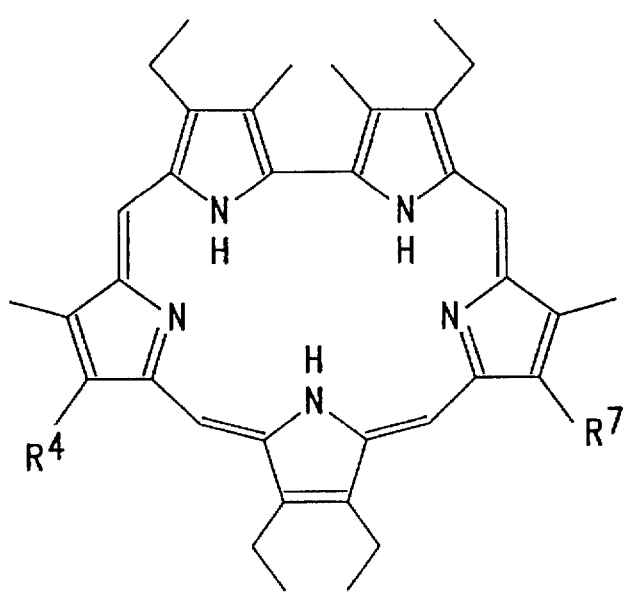
Figure 2:
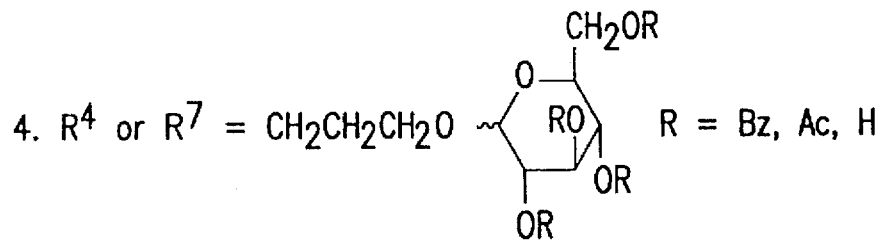
Figure 2:
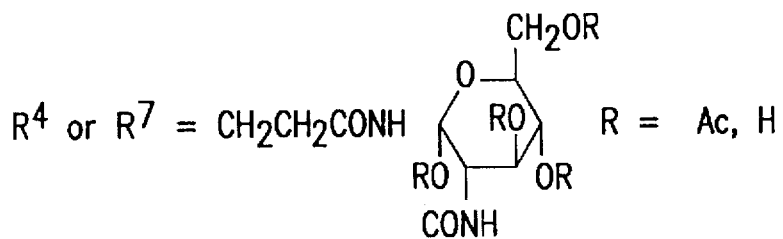

FIG. 2. Water-soluble sapphyrins. FIG. 2 represents examples of the two categories of water-soluble sapphyrins, namely, polyhydroxysapphyrins and sapphyrin-sugar derivatives. In that these structures are generally based upon structure III, it will be understood that $R^1$–$R^{10}$ may include any of the groups listed above, and that at least one of the R ($R^1$–$R^{10}$) will be of the formula $(CH_2)_n$—A—$(CH_2)_m$—B; wherein, again, A may include any of the groups listed above and B will provide the water-soluble polyhydroxy moiety (sugar or non-sugar).

Specific examples of water-soluble polyhydroxysapphyrins include, but are not limited to, compounds such as 1 and 3, which were synthesized from the starting compounds 2a and 2b. Specific examples of water-soluble sapphyrin-sugar derivatives include, but are not limited to, compounds such as 4a–4c and 6, which were synthesized from the starting compounds 2 and 5. Any sugar or sugar derivative, such as those listed in Table 1, may be coupled to sapphyrin to form a water-soluble sapphyrin-sugar derivative in accordance herewith.

Figure 3A:
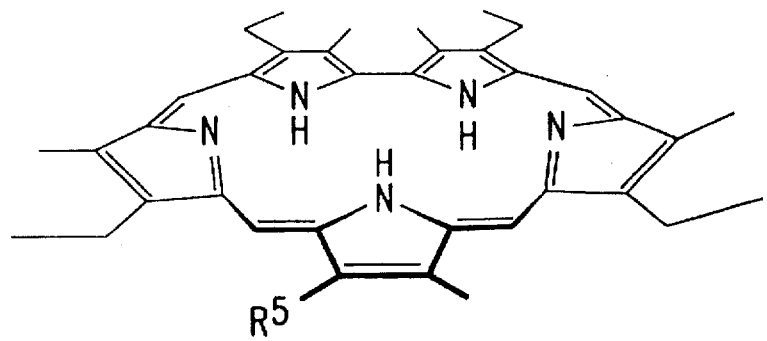

FIG. 3A. Sapphyrin-metal chelating group conjugates. Sapphyrin may be conjugated to a metal chelating moiety such as, for example, EDTA, EGTA, DTPA, DOTA, ethylene diamine, bipyridine, 1,10-phenanthralene, crown ether, aza crown, catechols, and the like. $R^1$–$R^{10}$ may include any of the groups listed above, and at least one of these R groups will be of the formula $(CH_2)_n$—A—$(CH_2)_m$—B; wherein A may include any of the groups listed above and B will be a metal chelating moiety, for example, one of those listed above, such as EDTA, ethylene diamine or 1,10-phenanthralene.

Figure 3B:
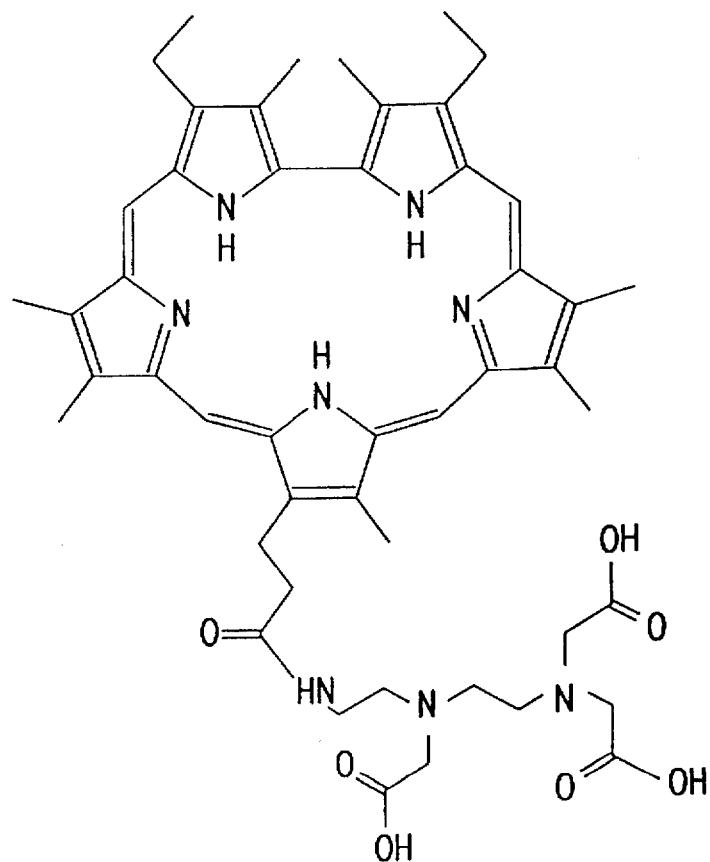

FIG. 3B, Structure 8 is a specific example in which sapphyrin is conjugated to EDTA (the precursors for which compound are represented by structures 7a and 7b, also set forth in FIG. 3A).

Figures 1, 4A:
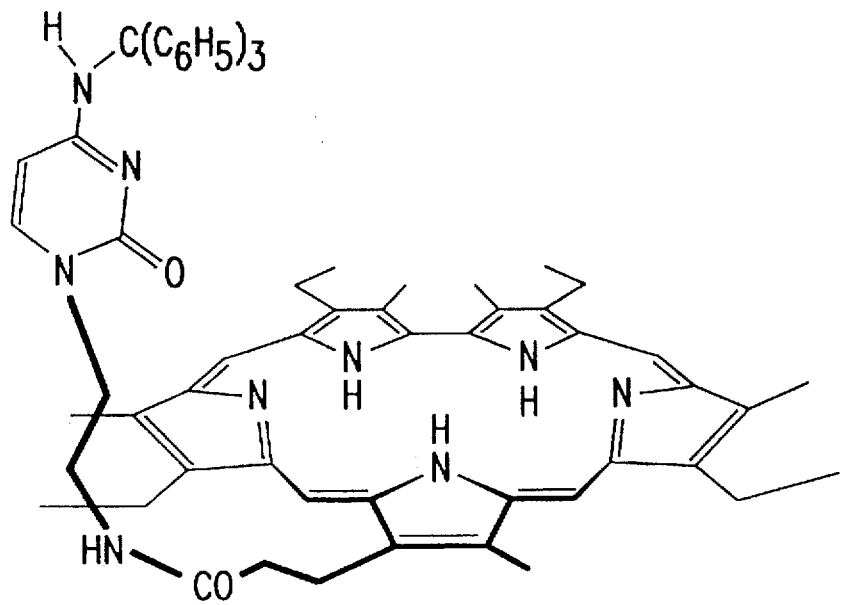
Figures 2, 4A:
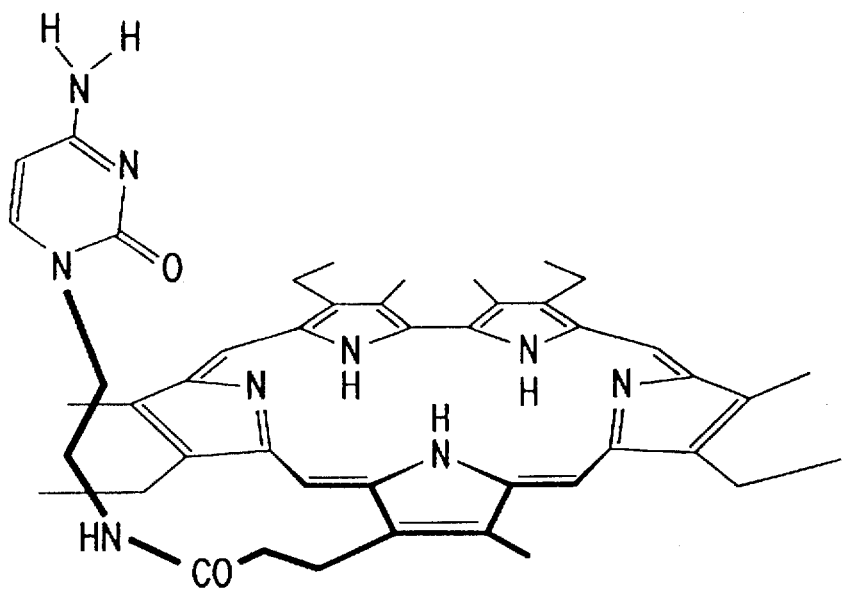
Figures 3, 4A:
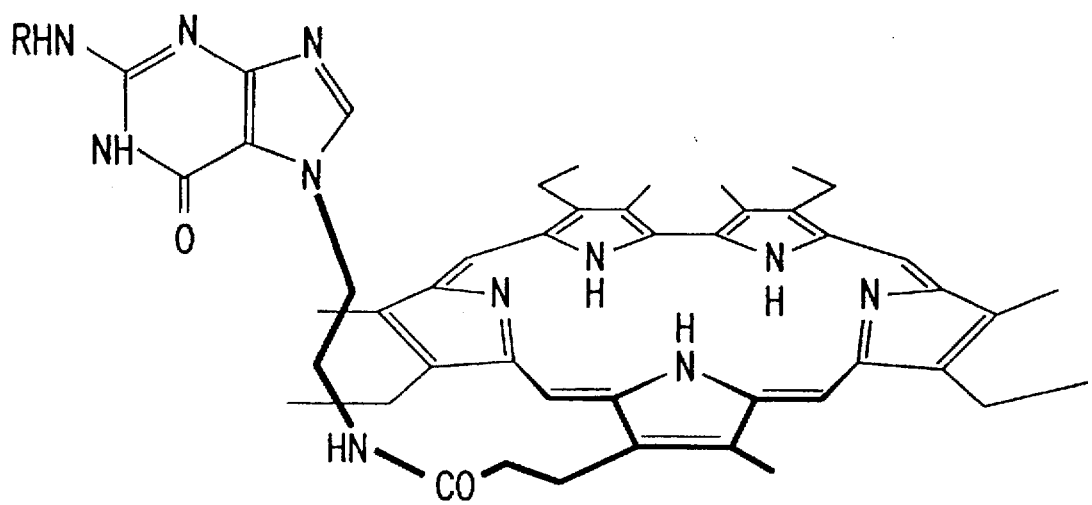
Figures 4, 4A:
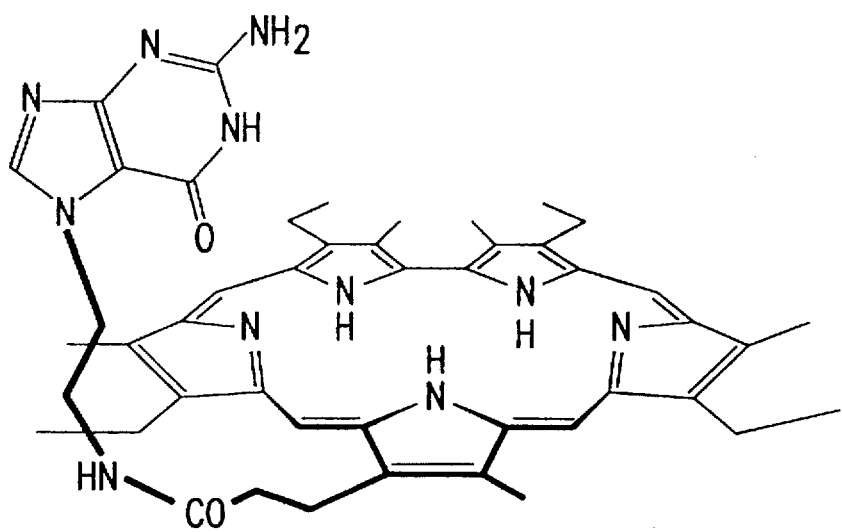

FIG. 4. Sapphyrin nucleobase derivatives. The sapphyrin nucleobase monomer derivatives of the present invention include both ditopic and tritopic sapphyrin receptors in which one or two nucleobases, respectively, are appended to the sapphyrin core. Again, $R^1$–$R^{10}$ may include any of the groups listed above, and at least one of these R groups will be of the formula $(CH_2)_n$—A—$(CH_2)_m$—B; wherein A may include any of the groups listed above and B will be one or more nucleobases, nucleobase derivatives or protected nucleobases. Conjugation of a nucleobase to a sapphyrin derivative to form a mononucleobase sapphyrin conjugate may be via any of the R groups $R^1$–$R^{10}$. Conjugation of the two separate nucleobases to a sapphyrin derivative to form a dinucleobase sapphyrin conjugate may also be via any two of the R groups $R^1$–$R^{10}$. However, it is contemplated that the creation of a symmetrical molecule, such as by substitution on $R^4$ and $R^7$, or $R^5$ and $R^6$, will be generally be preferred. The sapphyrin nucleobase derivatives may include any of the naturally-occurring purine or pyrimidine nucleobases, namely, cytosine, guanine, thymidine, adenine or uridine. Alternatively, they may include modified versions of any of these, such as those listed in Table 2 and phosphorylated forms thereof; or chemically modified nucleobases such as "protected" bases including, for example, a protecting group on the amino group of the nucleobase, such as, for example, 9-fluorenylmethylcarbonyl, benzyloxycarbonyl, 4-methoxyphenacyloxycarbonyl, t-butyloxycarbonyl, 1-adamantyloxycarbonyl, benzoyl, N-triphenylmethyl, N-di-(4-methoxyphenyl)phenylmethyl. FIG. 4 contains FIGS. 4A-1 through 4A-6, FIGS. 4B-1 through 4B-4 and FIG. 4C, a single diagram.

FIGS. 4A-1 through 4A-6: Sapphyrin mononucleobase derivatives. Specific examples of sapphyrin mononucleobase derivatives include, but are not limited to, structures 9–15; for example, the cytosine-containing compound, 10; and the guanine-containing compounds 12, 14 & 15.

Figure 1:
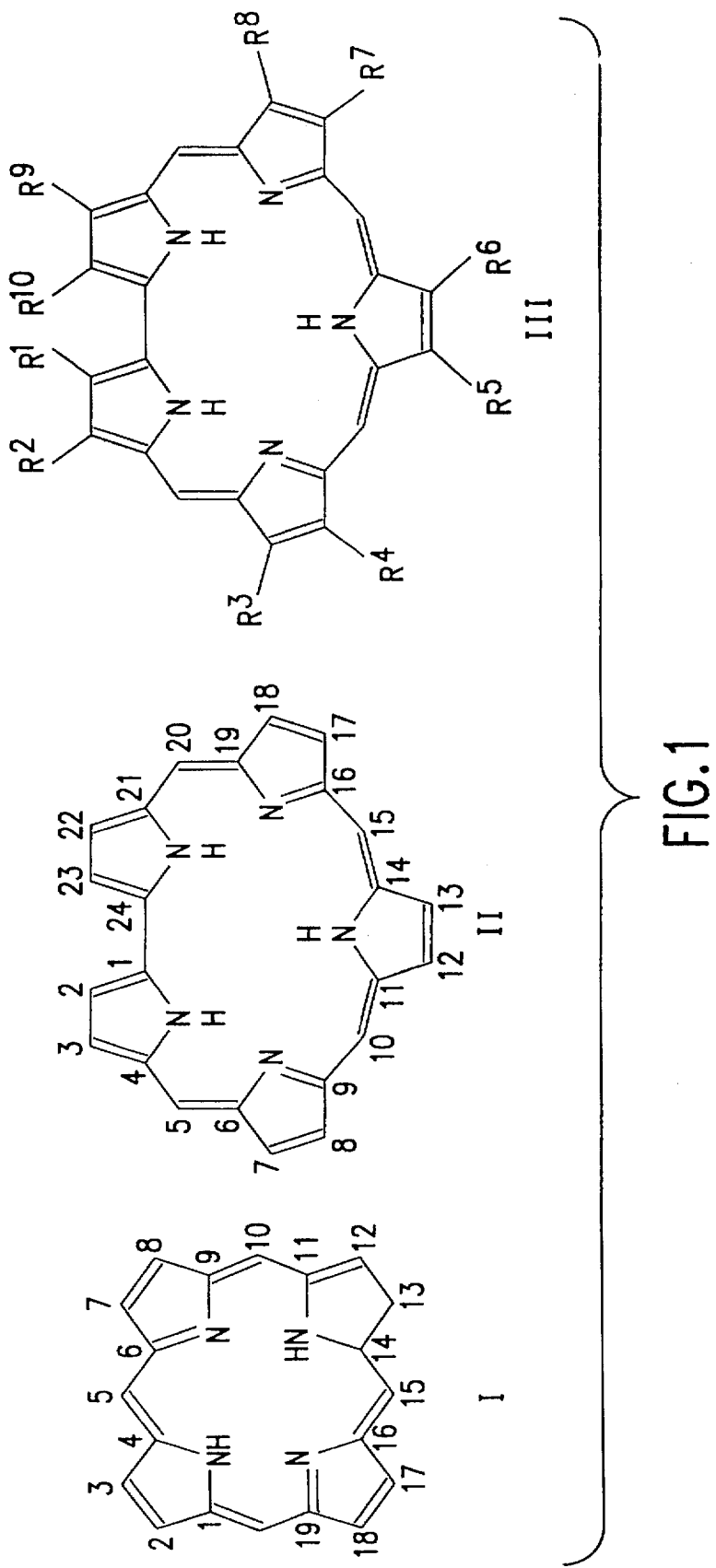
FIG. 1. Porphyrins and expanded porphyrins (large pyrrole-containing macrocyclic porphyrin analogues). Structure I, porphine; structure II, sapphyrin. Compounds I and II are represented in their generalized substituent-free forms, and show the standard numbering scheme. Structure III will be used throughout as a basis to define the novel sapphyrin derivatives, and polymers thereof, of the present invention.
Figures 4, 4A, 5:
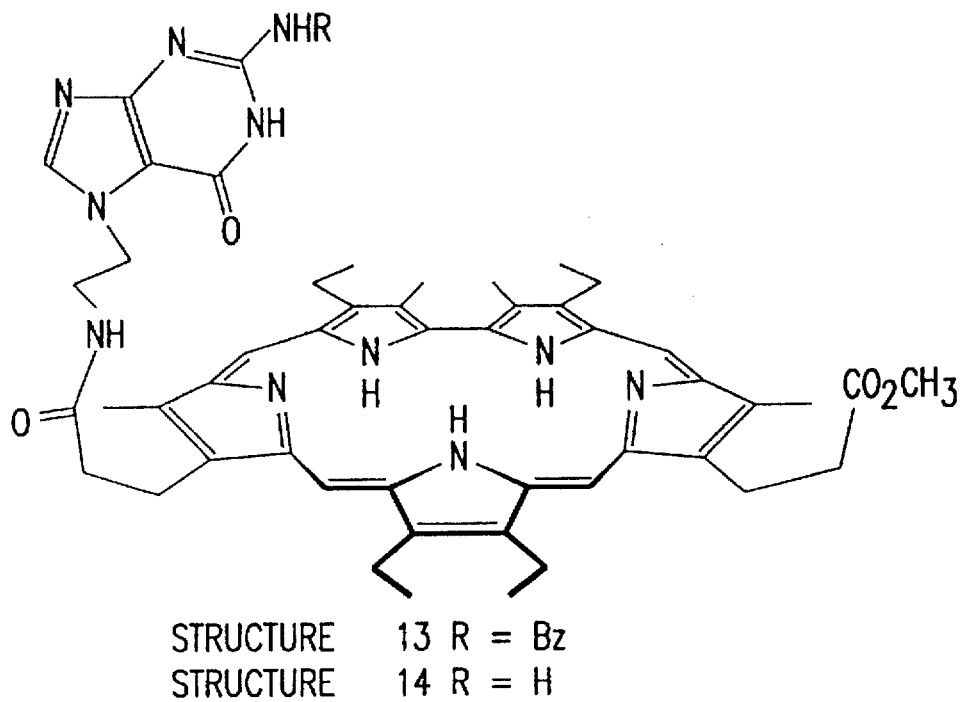
Figures 4, 4A, 5, 6:
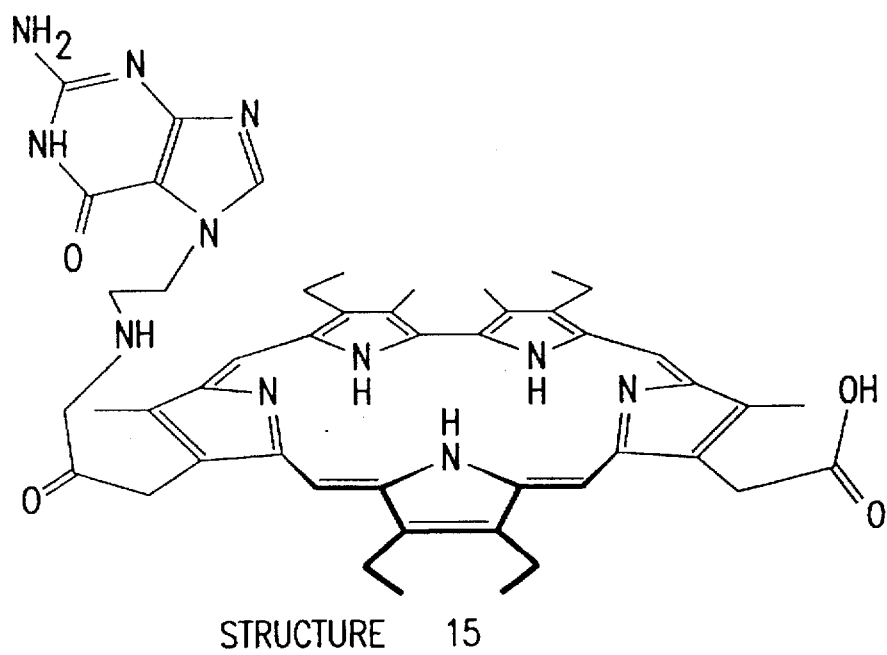
Figures 1, 4B:
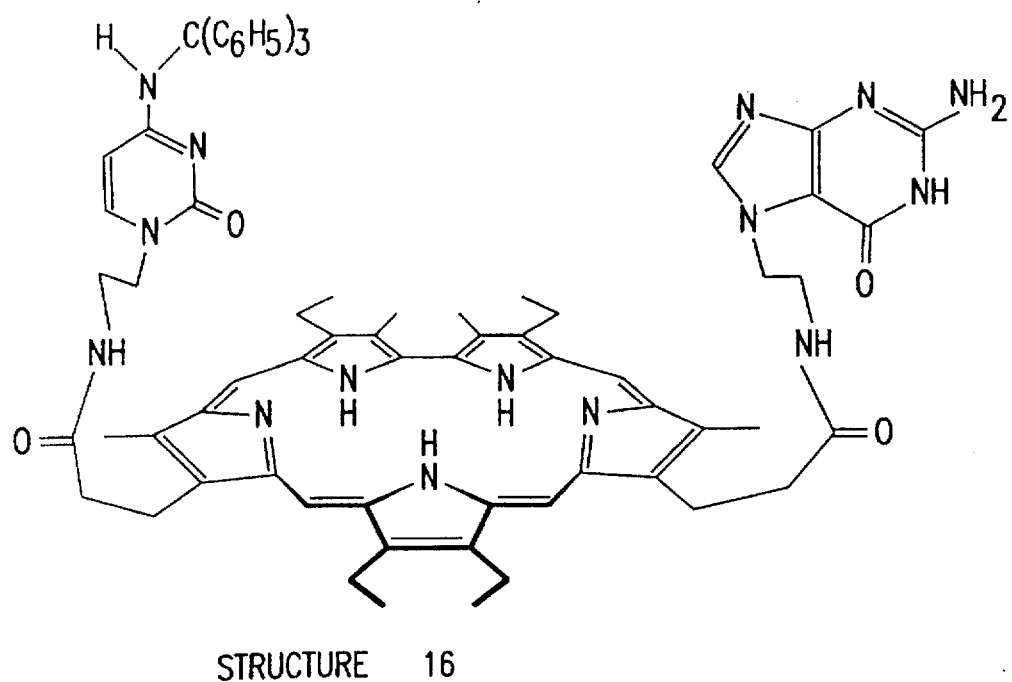
Figures 2, 4B:
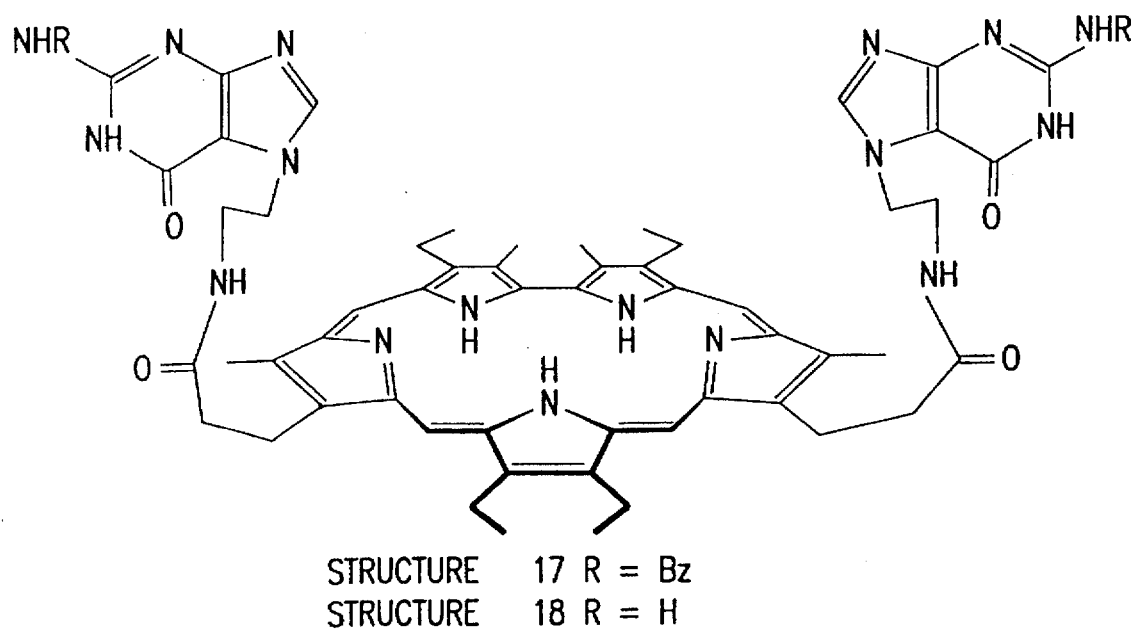
Figures 3, 4B:
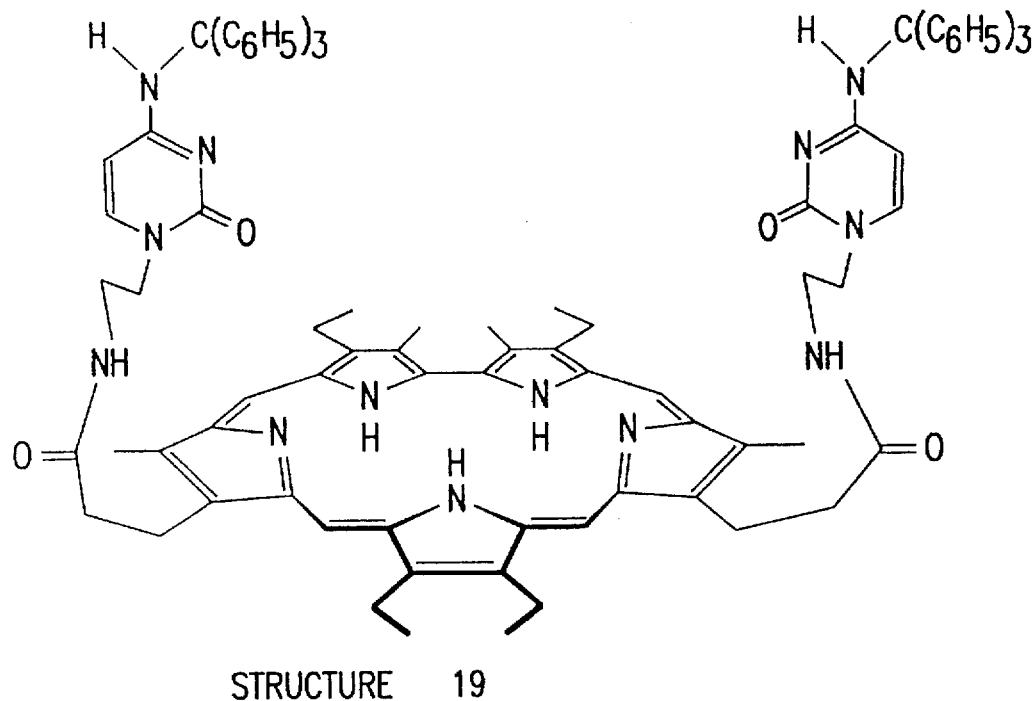
Figures 4, 4B:
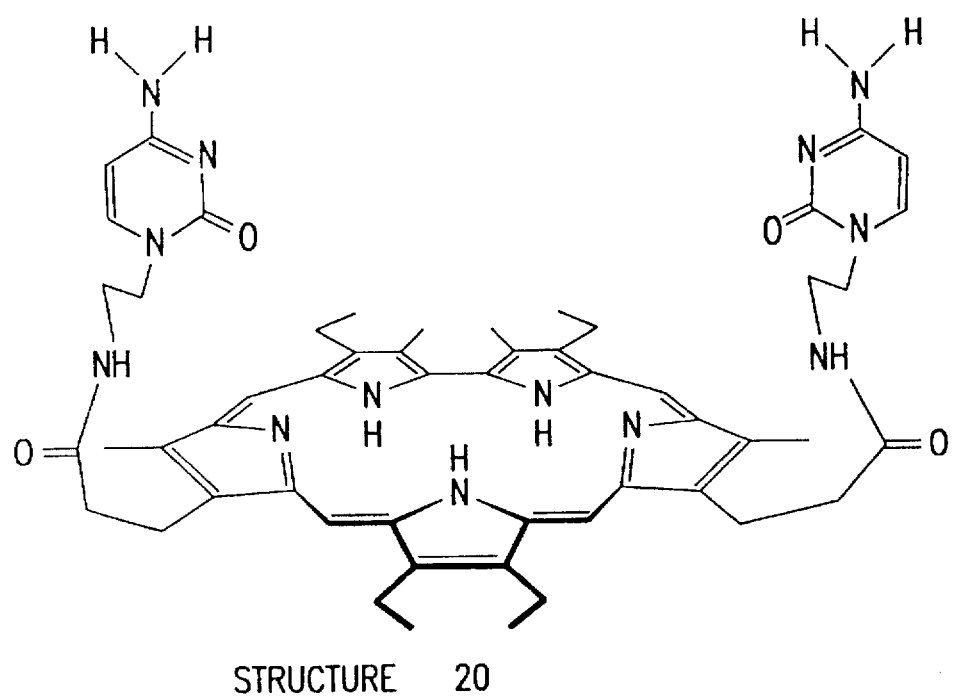

FIGS. 4B-1 thorugh 4B-4: Sapphyrin dinucleobase derivatives. These sapphyrin derivatives may also include any of the naturally-occurring purine or pyrimidine nucleobases in any combination (fifteen possible combinations), or any nucleobase derivatives or chemically modified nucleobases, such as those listed above. Specific examples of sapphyrin dinucleobase conjugates include, but are not limited to, structures 16–20; for example, compound 20, containing two cytosine groups; compound 18, containing two guanine groups; and compound 16, a heteronucleobase sapphyrin conjugate.

Figure 4C:
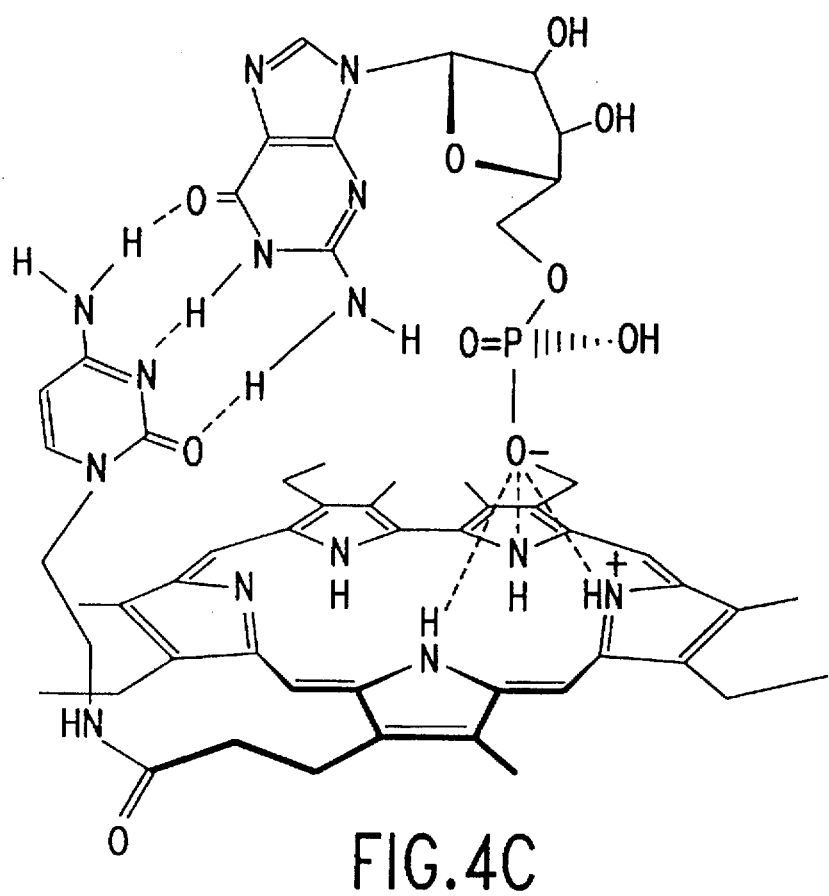

FIG. 4C: A possible structure for the proposed supramolecular complex formed between conjugate 10 and monobasic GMP.

FIG. 5. Sapphyrin oligomers and polymers and polymer-supported expanded porphyrins. FIG. 5 contains FIG. 5A, the general structural guideline; FIGS. 5B-1 through 5B-4, exemplary dimers and trimers; FIGS. 5C-1 through 5C-3, oligomers and polymers; and FIGS. 5D-1 through 5D-10, polymer- and matrix-supported expanded porphyrins.

Figure 5A:
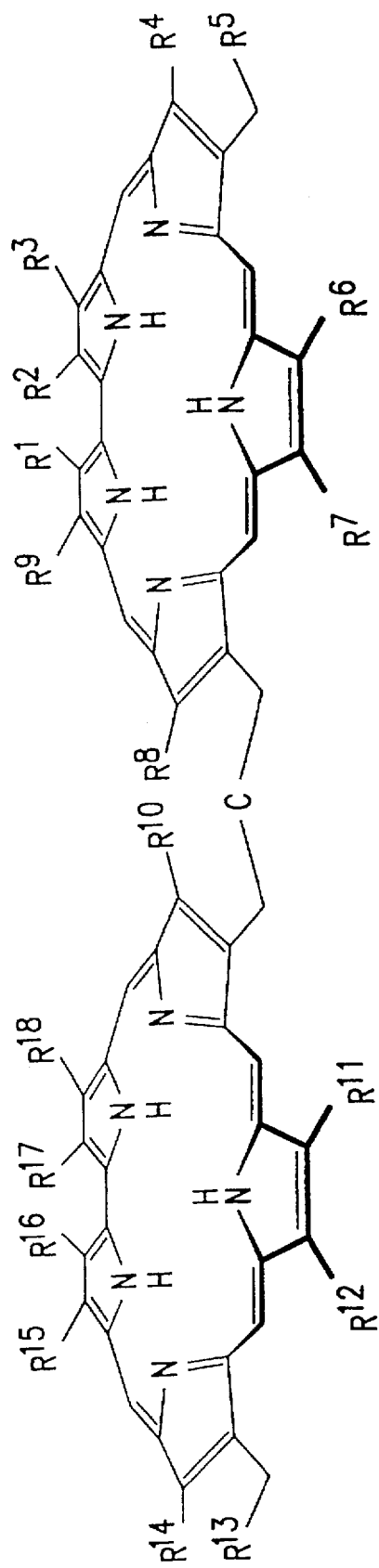
Figures 3, 5B:
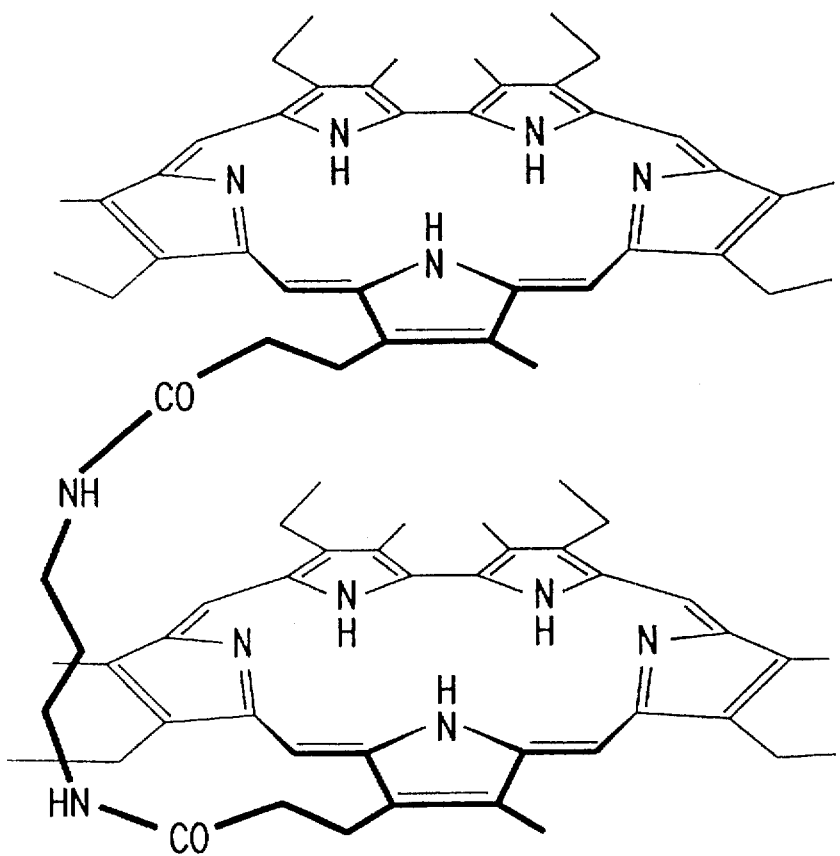
Figures 4, 5B:
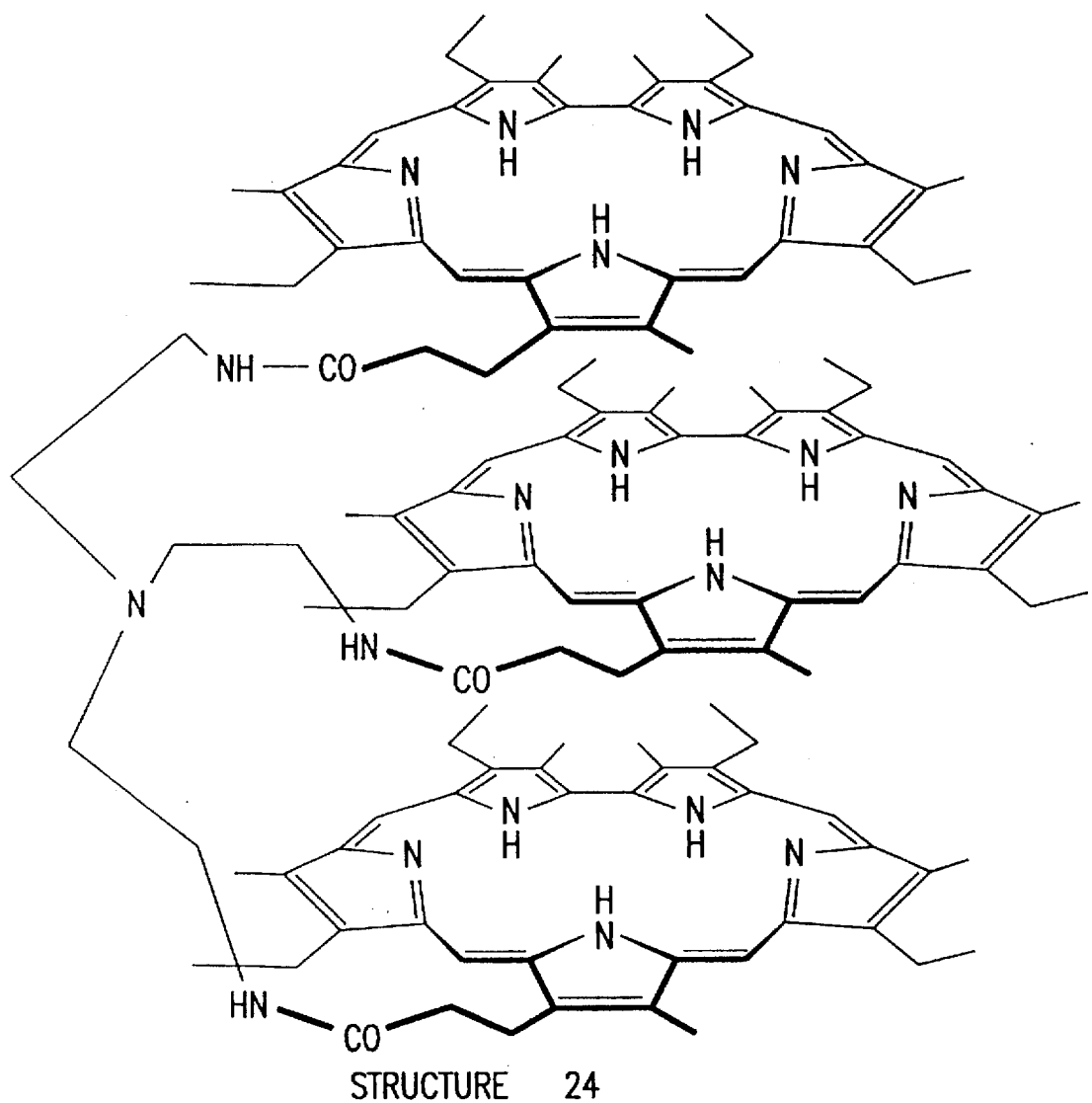
Figures 1, 5C:
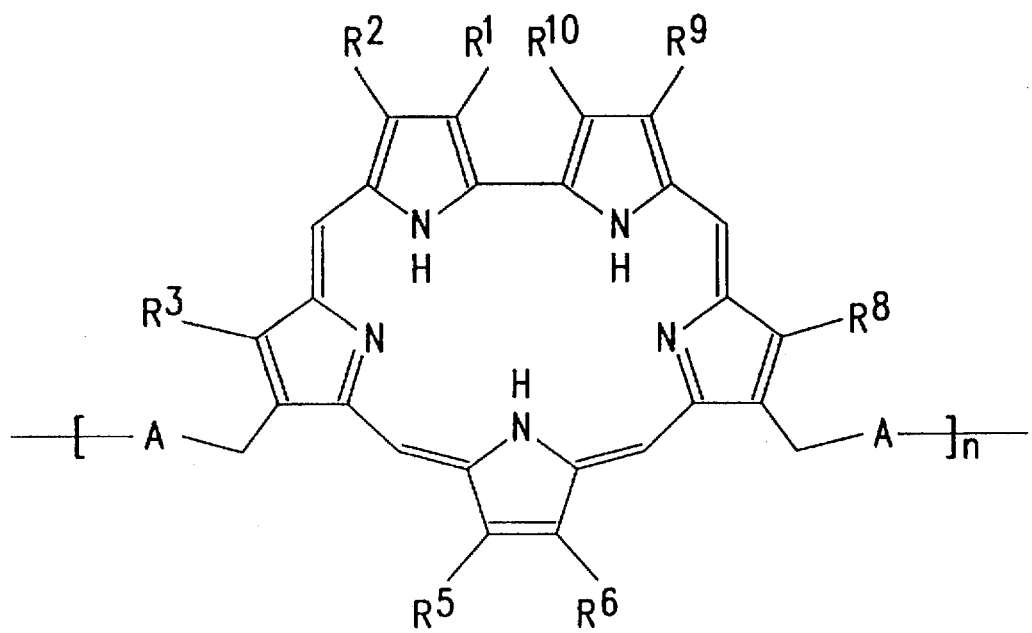
Figures 2, 5C:
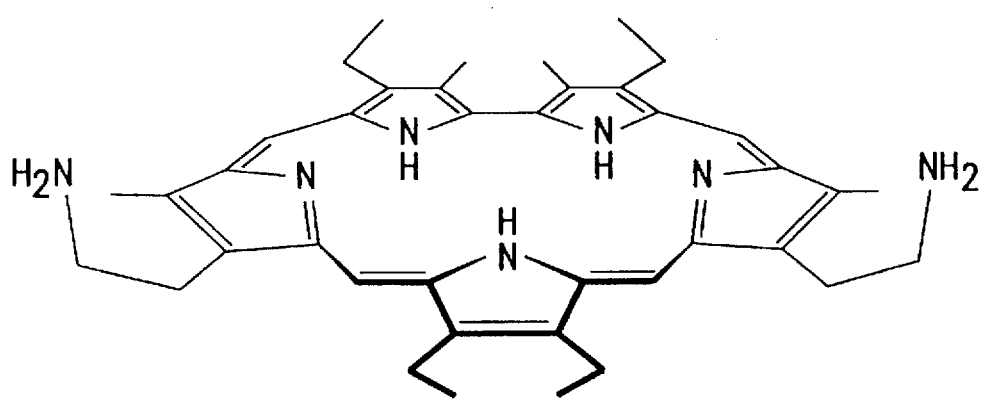
Figures 4, 5C:
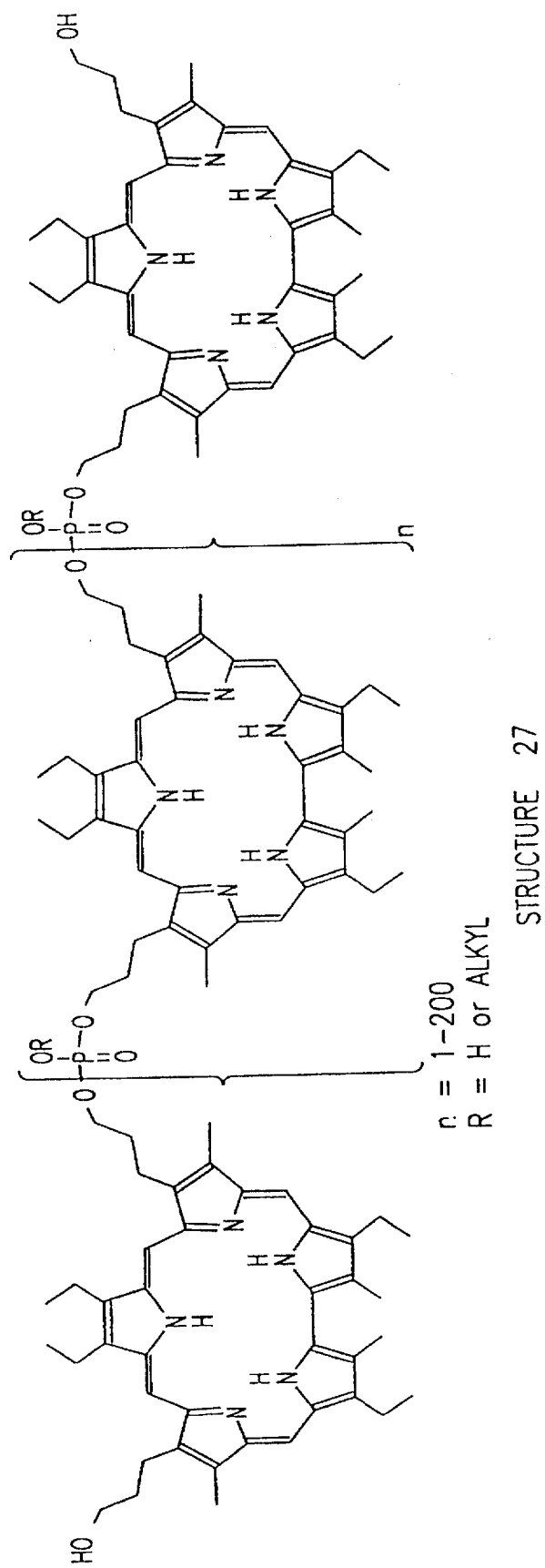

FIG. 5A: The sapphyrin molecules of the general structure III may be derivatized to include further sapphyrins or sapphyrin derivatives, oligosapphyrin derivatives, oligonucleotides or polymeric matrices, thus creating sapphyrin oligomers and polymers. As with the other novel sapphyrins, $R^1$–$R^{10}$ may include any of the groups listed above, wherein at least one of these R groups will be of the formula $(CH_2)_n$—A—$(CH_2)_m$—B, with A being any of the groups listed above. In these cases, B will be a sapphyrin, sapphyrin derivative, oligosapphyrin, polysapphyrin, oligonucleotide or any polymer, polymeric matrix or solid support. Conjugation of further derivatives to form a sapphyrin oligomer or polymer may be via any of the R groups $R^1$–$R_{10}$, with $R^4$, $R^5$ and $R^7$ being preferred targets. Conjugation at more than one point is also contemplated and may be via any two, or more, of the R groups $R^1$–$R^{10}$, such as $R^4$ and $R^7$, $R^3$ and $R^8$, or $R^5$ and $R^6$.

Structure IV of FIG. 5A represents the general structure for the oligomeric sapphyrins of this invention, and is an example of structure III, wherein a further sapphyrin derivative has been added. Structure IV includes $R^1$–$R^{18}$, which may be any of the groups listed above, and also "C" which is a spacer group which may be H, O, S, NH, $NR^{19}$, wherein $R^{19}$ is alkyl, alkene, alkyne, halide, alkyl halide, hydroxyalkyl, glycol, polyglycol, thiol, alkyl thiol, substituted alkyl, phosphate, phosphonate, sulfate, phosphate substituted alkyl, phosphonate substituted alkyl, sulfate substituted alkyl, COO, CONH, CSNH, $CONR^{11}$; alkyl, alkene, polyene, alkyne, aryl, alkyl halide, hydroxyalkyl, glycol, polyglycol, sulfide, disulfide, alkyl thiol, aminoalkyl, carboxyalkyl, alkoxyalkyl, aryloxyalkyl, alkyloxycarbonyl, aryloxycarbonyl, aldehyde, dialkyl, ether, ketone, ester, phosphate, phosphonate, sulfate, phosphate substituted alkyl, phosphonate substituted alkyl, or sulfate substituted alkyl.

FIGS. 5B-1 through 5B-3 includes specific examples of dimeric sapphyrin structures 21–23, and an exemplary trimeric sapphyrin structure, 24, FIG. 5B-4.

FIGS. 5C-1 through 5C-3: Structure V represents the general structure for the polymeric sapphyrins of the present invention. Structure V is a more specific polymeric example of both structures III and IV, wherein further sapphyrin derivatives or other moieties, such as oligonucleotides or sapphyrin-oligonucleotides, have been added. In structure V, n may be from 1–100, or even from 1–200, $R^1$–$R^{10}$ and A may be H, alkyl, alkene, alkyne, halide, alkyl halide, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, aldehyde, ether, ketone, carboxylic acid, phosphate, phosphonate, sulfate, phosphate substituted alkyl, phosphonate substituted alkyl, or sulfate substituted alkyl.

Structure 25 of FIG. 5C-2 represents a sapphyrin derivative which was employed as a precursor in sapphyrin oligomer and sapphyrin polymer syntheses. Examples of sapphyrin polymers include, but are clearly not limited to, the sapphyrin structures 26A and 26B of FIG. 5C-3i where X=NH and X=O, respectively, and structure 27 of FIG. 5C-3ii, where phosphate linkages are employed; in both of these structures, n may be up to and including about 200 units or even more depending on the intended use of the polymer and the synthetic chemistry chosen. Structure 25 represents a precursor sapphyrin derivative employed in oligomer synthesis.

FIGS. 5D-1 through 5D-10: Polymer- and Matrix-supported expanded porphyrins. The polymer- and matrix-supported expanded porphyrins of the invention include both polymer-supported rubyrins and polymer-supported sapphyrins, as exemplified by Structures VI and VII, respectively. The synthesis and use of rubyrin and various rubyrin derivatives is described in detail in U.S. patent application Ser. No. 08/015,208, which is specifically incorporated herein by reference.

Structure VI represents the general structure for the class of polymer-supported expanded porphyrins which include rubyrin and rubyrin derivatives and conjugates. In structure VI, the rubyrin may be derivatized at any position to form a $(CH_2)_n$—A—$(CH_2)_m$—B structure, wherein A may be any of the groups listed above and B will include a polymer, polymeric matrix or solid support. B may also include any of the groups listed above for A, and preferably, will include an aryl, alkyl, silyl, siloxy, aminoaryl, amino, amidoaryl or silyloxy group. The polymer, or solid support, of this structure may also be one of a variety of polymers, polymeric matrices, glasses or solids, such as, for example, silica, agarose, polyacrylamide, controlled pore glass, silica gel, Merrifield resin, polystyrene, glass, clay, zeolites or sepharose.

In structure VI, the "rubyrin" attached to the polymer in Structure VI may be any of the rubyrins represented by structures 28, 29 or 30, as disclosed in U.S. Ser. No. 08/015,208, incorporated herein by reference. In structures 28, 29 and 30, $A_1$ and $A_2$ may be nitrogen, oxygen or sulphur. One of the substituents $R_1$–$R_6$ or $X_1$–$X_4$ will be derivitized to form the $(CH_2)_n$—A—$(CH_2)_m$—B structure, wherein B includes the polymeric support. The other of the substituents $R_1$–$R_6$ and $X_1$–$X_4$ may be separately and independently H, alkyl, aryl, amino, hydroxyl, alkoxy, carboxyl, carboxamide, ester, amide, sulfonato, hydroxy substituted alkyl, alkoxyl substituted alkyl, carboxyl substituted alkyl, amino substituted alkyl, sulfonato substituted alkyl, ester substituted alkyl, amide substituted alkyl, substituted aryl, substituted alkyl, substituted ester, substituted ether, substituted amide; or may be of the formula $(CH_2)_{n-A-(CH2)_m}$—B, as described above.

Structure VII represents the general structure for the class of polymeric sapphyrins termed polymer supported sapphyrins. In structure VII, any of the groups $R^1$–$R^{10}$ may be derivatized to form a $(CH_2)_n$—A—$(CH_2)_m$—B structure, wherein A may be any of the groups listed above and B will include a polymer, polymeric matrix or solid support. B may also include any of the groups listed above for A, and preferably, will include an aryl, alkyl, silyl, siloxy, aminoaryl or amino group. In structure VII and structures 31 through 38, the polymer, or solid support, of this structure may also be one of a variety of polymers, polymeric matrices, glasses or solids, such as, for example, silica, agarose, polyacrylamide, controlled pore glass, silica gel, Merrifield resin, polystyrene, clay, zeolite or sepharose.

In structure VII, Z may be, for example, $CH_3$, $(CH_2)_{11}CH_3$, $(CH_2)_{17}CH_3$, $(CH_2)_7$ $CH_3$, phenyl, naphthyl, substituted naphthyl, a nucleobase, oligonucleotide, or other similar structures which will be known to those of skill in the art. In Structure VII, the other R groups of the sapphyrin molecule, particularly $R^8$ may be, for example, H, $CO_2CH_3$, $CONH(CH_2)_n$-nucleobase, an oligonucleotide or another expanded porphyrin such as a sapphyrin or sapphyrin derivative.

Specific examples of polymer supported sapphyrins include, but are clearly not limited to, the sapphyrin structures 31, 32, 33, 34, 35, 36, 37 and 38 of FIGS. 5D-3 through 5D-10. In structures 34, 36 and 37, Z may again be $CH_3$, $(CH_2)_{11}CH_3$, $(CH_2)_{17}CH_3$, $(CH_2)_7$ $CH_3$, phenyl, naphthyl, substituted naphthyl, a nucleobase or oligonucleotide. In structure 37, Ar is phenyl. In structure 38, T may be benzyl, benzoyl, naphthylmethyl, adamantyl, or an alkyl chain with between 1 and about 18 Carbon atoms ($C_nH_{2n-1}$, where n=1–18); and X may be phenyl, naphthyl, p-nitrobenzoyl or an alkyl chain with between 1 and about 18 Carbon atoms ($C_nH_{2n-1}$, where n=1–18). In structures 31 through 38, the polymer or matrix may be silica gel, Merrifield resin, glass, controlled pore glass, agarose, sepharose, polyacrylamide, polystyrene, clay, zeolite or other polymer or matrix that can be functionalized by one skilled in the art of chemical synthesis.

FIG. 6. Structure 39. This molecule, a tetrahydroxy porphyrin derivative, was employed as a "control" molecule, or as a point of comparison, in the sapphyrin DNA binding studies described herein.

FIGS. 7A-i and 7A-ii: HPLC separation of adenosine phosphates using the first sapphyrin-modified silica gel, 34, in which Z is $CH_3$. 20 µl of a mixture of adenosine, AMP, ADP, and ATP was loaded onto and eluted off the first sapphyrin-modified silica gel using an isochratic buffer of 100 mM dibasic ammonium phosphate buffer at a pH of 7.0 and a flow rate of 0.2 ml/min. The wavelength of 260 nm was monitored and results were confirmed with retention times and UV-visible spectrum obtained from samples of individual compounds. Insert shows the same mixture run through a control column with no sapphyrin.

FIG. 7B: HPLC separation of adenosine phosphates using first sapphyrin-modified silica gel, 34, in which Z is $CH_3$. 20 µl of a mixture of adenosine, AMP, ADP, and ATP was loaded onto and eluted off the first sapphyrin-modified silica gel using an isochratic buffer of 500 mM dibasid ammonium phosphate buffer at a pH of 7.0 and a flow rate of 1.0 ml/min. The wavelength of 260 nm was monitored and results were confirmed with retention times and UV-visible spectrum obtained from samples of individual compounds.

FIGS. 8A-i and 8A-ii: HPLC separation of commercially obtained adenosine-derived oligonucleotides using the first sapphyrin-modified silica gel, 34, in which Z is $CH_3$. 20 µl of a mixture of the 2-, 3-, 4-, 5- and 6-mer of polydeoxyadenylic acid was loaded onto and eluted off the column using an isochratic buffer of 100 mM dibasic ammonium phosphate at pH 7.0 and a flow of 0.35 ml/min. The wavelength of 260 nm was monitored and results were confirmed with retention times and UV-visible spectrum obtained from samples of individual compounds. The insert shows the same mixture run through a control column with no sapphyrin.

Figure 8B:
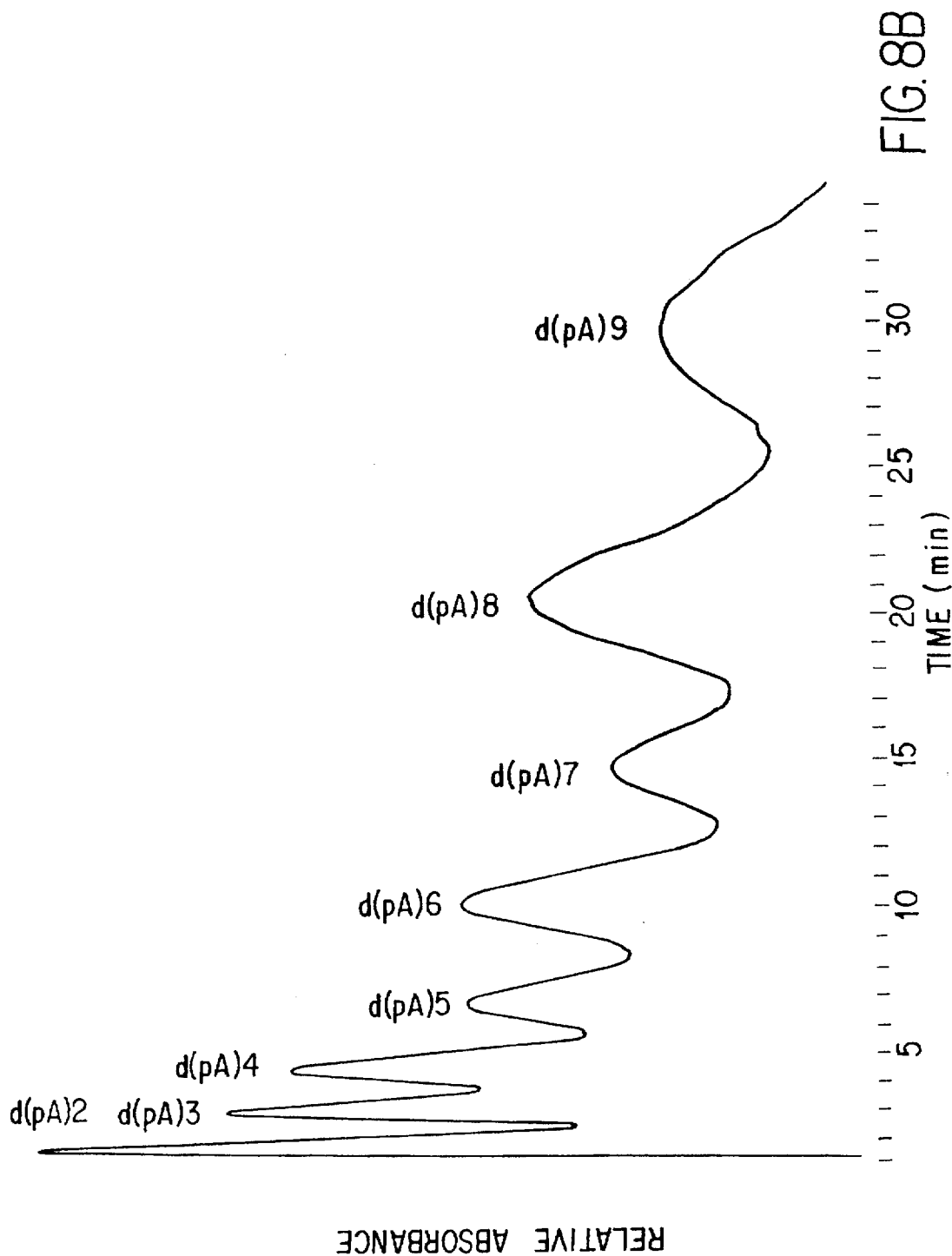

FIG. 8B: HPLC separation of commercially obtained adenosine-derived oligonucleotides using the first sapphyrin-modified silica gel, 34, in which Z is $CH_3$. 20 µl of a mixture of the 2-, 3-, 4-, 5-, 6-, 7-, 8, and 9-mer of polydeoxyadenylic acid was loaded onto and eluted off the column using an isochratic buffer of 1.0M dibasic ammonium phosphate at pH 7.0 and a flow of 1.5 ml/min. The wavelength of 260 nm was monitored and results were confirmed with retention times and UV-visible spectrum obtained from samples of individual compounds.

DETAILED DESCRIPTION OF THE PREFERRED EMBODIMENTS

Sapphyrins are large pyrrole-containing macrocyclic analogous to porphyrins (e.g. porphine, FIG. 1, structure I). The synthesis of various sapphyrins has been previously reported[2-6,11,12], see also U.S. Pat. No. 5,159,065, incorporated herein by reference. Structural information is available for a limited number of sapphyrin analogues, for example[4,6,11]. The present invention concerns a variety of new sapphyrin-based systems, in which the sapphyrin molecule has been derivatized in a number of novel ways. In particular, this invention encompasses, but is not limited to, four to five broad new groups of sapphyrin-based molecular structures. These may be generally defined as: (I) water soluble sapphyrins; (II) sapphyrin-metal chelating conjugates; (III) sapphyrin-nucleobase conjugates; (IV) oligomeric and polymeric sapphyrin derivatives; and (V), the polymer sub-group of polymer-supported sapphyrins which includes new chromatographic supports derived from expanded porphyrins and, particularly, sapphyrin-based chromatographic and electrophoretic supports.

Individually and collectively these new sapphyrin species overcome known deficiencies associated with extant sapphyrins. This is because all sapphyrins known at the time of this invention were exclusively monomeric in nature and insoluble in aqueous media at or near neutral pH. Thus, the sapphyrins known prior to the present invention were incapable of forming well-characterized, water soluble complexes with phosphorylated entities, including DNA, RNA, nucleotides, nucleotide analogues, and simple phosphate and phosphorate monoesters, at or near neutral pH.

In addition, all sapphyrins known at the time of this invention were recognized to be quite limited in terms of their substitution patterns, bearing either hydrogens, alkyl groups, or carboxyl alkyl groups in the so-called β-positions. Thus, these systems could not and did not display any kind of binding selectivity as far as phosphate chelation was concerned; no specificity, for instance, for or against a particular nucleotide (i.e. guanosine-5'-monophosphate vs. cytosine 5-'-monophosphate) was observed in such cases where such binding was inferred[5].

Furthermore, this same lack of substituent versatility meant that sapphyrin systems carrying potentially reactive side chains were completely unknown and this too was recognized as limiting the utility of those few sapphyrins known to be extant at the time of this invention. Thus, the inventors felt it worthwhile to prepare 1) water soluble sapphyrins, 2) sapphyrins bearing specific recognition units such as nucleobases, 3) sapphyrins bearing reactive sites, such as the metal chelating derivatives embodied in modified EDTA side chains, and 4) polymer supported sapphyrins and 5) oligomeric and polymeric sapphyrin systems, wherein the binding and recognition affects achieved in the monomeric sapphyrins might be expected to be greatly amplified. None of these could be prepared using the methods available in the prior art.

Water soluble porphyrin and porphyrin-like derivatives, such as sapphyrins, are known to be of interest in biomedical applications including photodynamic therapy (PDT)[1]. The present inventors also recognized their potential for use in DNA recognition and modification. They reasoned that water soluble sapphyrin-based compounds without ionizable groups may be particularly advantageous for use in a number of ways, such as in PDT, cellular recognition and targeting, in the transport of biologically important molecules, as well as in the preparation of new solid supports for use in chromatographic or electrophoretic applications.

Anionic phosphorylated entities are ubiquitous in biology. They play a critical role in a variety of fundamental processes ranging from gene replication to energy transduction.[13] In addition, certain phosphate-bearing nucleotide analogues, such as, e.g., 9-(β-D-xylofuranosyl)guanine-5'-monophosphate (Xylo-GMP), are known to display antiviral activity in vitro.[9] However, Xylo-GMP, like a considerable number phosphorylated nucleotide analogues which exhibit antiviral activity in cell-free extracts, is inactive in vivo[9] due to its inability to cross lipophilic cell membranes[7,8].

The anti-herpetic agent, acyclovir (9-[(2-hydroxyethoxy)methyl]-9H-guanine), is active in vivo. Acyclovir can enter the cell only in its uncharged nucleoside-like form. Once in the cytoplasm, it is phosphorylated, first by a viral-encoded enzyme, thymidine kinase, and then by relatively nonspecific cellular enzymes to produce an active, ionic triphosphate nucleotide-like species. There it functions both as an inhibitor of the viral DNA polymerase and as a chain terminator for newly synthesized herpes simplex DNA.

The biological limitations of many other potential antiviral agents, including Xylo-G, arise from the fact that they are not phosphorylated once inside the cell and are therefore largely or completely inactive. If, however, the active monophosphorylated forms of these putative drugs could be transported into cells, it would be possible to fight viral infections with a large battery of otherwise inactive materials. If such specific into-cell transport were to be achieved, it would therefore greatly augment the treatment of such debilitating diseases as, for example, AIDS, herpes, hepatitis and measles. Given the fact that AIDS is currently a major national health problem of frightening proportions, and that something so nominally benign as measles still claims over 100,000 lives per year world-wide, treatment of these diseases would be particularly timely and worthwhile.

Not surprisingly, in recent years, increasing effort has been devoted to the problem of phosphate recognition and a number of phosphate-binding receptors are now known.[10] In spite of this, there are currently no artificial entities capable of effecting the selective through-membrane transport of mononucleotides and oligomeric polynucleotides at neutral or near-neutral pH, i.e., at a biological pH. A major aim of the inventors' studies has been therefore to provide a means of trans-porting active mono- and polyphosphorylated forms of these and other agents into cells. This would allow a wide range of otherwise inactive compounds, such as antivirals, to be employed therapeutically, and would also create new possibilities for gene therapy.

In preliminary work concerning nucleoside transport, the present inventors employed triisopropylsilyl (TIPS) substituted (phosphate-free) nucleosides[14]. It was found that efficient and selective through-membrane transport of non-charged nucleoside analogues could be achieved by using the complementary TIPS derivatives as carriers[14]. Not surprisingly, however, these same TIPS derivatives proved completely ineffective as transport agents for the analogous phosphate-containing nucleotide derivatives. Thus, whilst confirming the viability of a base-pairing approach to selective nucleotide recognition, this work served to highlight further the need for an organic soluble, neutralizing, phosphate binding group.

The inventors reasoned that if sapphyrin-based systems were to be made effective as neutral-regime carriers, say, e.g. for GMP, it would require the construction of polytopic receptor systems in which a nucleobase recognition unit, in this case, a cytosine-like group, were "appended" directly onto the phosphate-chelating expanded porphyrin core. Naturally, they also contemplated the use of nucleobases recognition units other than cytosine for use in the specific binding and transport of the complementary nucleobases and nucleobase-containing compounds.

To synthesize multitopic receptors, the inventors developed strategies to address the following objectives: (i) the independent development of molecular recognition strategies for the complexation of two very different kinds of substrates (charged anionic and neutral nucleobase); (ii) their subsequent co-combination so as to provide receptors bearing both kinds of binding subunits; and (iii) various alternative methods of receptor oligomerization so as to provide oligomeric species bearing numerous combinations of multitopic receptors.

Pursuing these strategies led to the development of the sapphyrin-based ditopic receptor systems of the present invention, capable of recognizing both the anionic phosphate and the neutral portions of the nucleotide derivatives, such as the purine or pyrimidine moieties. Molecules of this type are, indeed, capable of the binding and transport of nucleotides and their derivatives. This theme was extended to the preparation of oligomeric, multitopic, receptors capable of recognizing multiple phosphate anions and nucleobase portions of nucleotide derivatives arranged in specific sequences.

The ditopic receptor systems are ideal vehicles for the intracellular transport of nucleotides and their derivatives, including anti-viral agents. The multitopic receptors, likewise, are contemplated to be of use in binding to oligonucleotides and specific sections of DNA or RNA and in transporting such nucleic acid segments into cells. The phosphate and nucleic acid base ("nucleobase") recognition, through-membrane transport and cell delivery properties of the present invention are thus applicable to the recognition and delivery of a large variety of monomeric and oligomeric species, including DNA, RNA and antisense constructs. In certain embodiments, one may wish to employ the novel constructs to transport oligonucleotides which contain C-5 propyne analogues of uridine and cytidine into cells[39].

The sapphyrins and sapphyrin-containing compositions of the invention may be administered to an animal, including human subjects or patients, for a variety of reasons. For example, in order to deliver a specific compound to a cell, as may be used to introduce an anti-proliferative, anti-cancer or anti-viral agent or a sense or antisense oligonucleotide into a cell which would benefit from the actions of such a compound. Therefore, further compositions envisioned are those which comprise an effective amount of a sapphyrin, as disclosed herein, dissolved or dispersed in a pharmaceutically acceptable carrier or aqueous medium.

The phrases "pharmaceutically or pharmacologically acceptable" refers to molecular entities and compositions that do not produce an adverse, allergic or other untoward reaction when administered to a human. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the function of the sapphyrin, its use in the therapeutic compositions is contemplated. Supplementary active ingredients, e.g., other anti-viral agents, can also be incorporated into the compositions.

In addition to the compounds formulated for parenteral administration, such as intravenous or intramuscular injection, other pharmaceutically acceptable forms include those for topical administration, such as sapphyrin-containing compositions formulated into cremes, lotions and the like, and even time release capsules. The preparation of pharmaceutically-acceptable sapphyrin compositions will be known to those of skill in the art in light of the present disclosure.

The inventors' surprising discovery that expanded porphyrins, such as rubyrin and sapphyrin, recognize and bind phosphates (see references 4a, 22 and U.S. Ser. No. 08/015,208, incorporated herein by reference), also lead the inventors to reason that such expanded porphyrins would be ideal for use in laboratory techniques to iseparate and purify nucleotides and oligonucleotides. This is a very important area to both scientists and clinicians as nucleotides, natural and synthetic oligonucleotides play critical roles in modern biotechnology. oligonucleotides ("oligos") are used, for instance, as hybridization probes in blot analyses, primers for PCR amplification, and for site-specific mutagenesis. Furthermore, in areas that are under FDA jurisdiction, oligonucleotide-derived products are currently being used as probes for the detection of genetic diseases and for proviral HIV, the causative agent of Acquired Immunodeficiency Syndrome (AIDS).[23] They are also being considered as potential chemotherapeutic agents, both directly, i.e., in gene therapy, and in an antisense fashion.[24]

All the above applications for using oligos require oligonucleotide materials of impeccable purity (often greater than >99.99%).[25] Such purity, however, is not so easy to obtain using existing technology.[25,26] Presently, gene products and other oligonucleotide-type materials are purified using polyacrylamide gel electrophoresis (PAGE). This approach suffers from the drawbacks of being time-consuming, requiring toxic materials, and is painfully manpower-sensitive and low-yielding.[23]

Liquid chromatography, high performance liquid chromatography (HPLC), and High Performance Affinity Chromatography (HPAC)[27,28] using specialty silica gels are currently used to separate biological molecules. Indeed, silica gel. phases with bonded groups, such as linear hydrocarbons, amino groups, cyano-groups, carboxylic amides and amino acids are all known.[27-29] Unfortunately, few if any of these phases are efficacious for the efficient, high-yielding separation of nucleotides and oligonucleotides.

Those that work best for this purpose are ion exchange columns which, on a limited basis, can sometimes separate oligonucleotides containing 40 or fewer residues. However, this technique still suffer from several limitations, not least that it requires severe conditions, including elution at pH 2.7, for routine operation.[29] The use of high concentration buffers (greater than 1M), and gradients which often include formic acid or formamide, also limits the half lives of ion exchange columns. Furthermore, commercially available hydroxyapatite columns are limited for low pressure only (up to 719 psi). Reverse phase columns are designed for pressures up to 5000 psi. However, this separative technique is based on hydrophobic interaction and, because there is not a specific interaction for phosphorylated species, it is not surprising that effective separation is not generally achieved.

Recently, Takemoto et al. reported a new type of stationary phase in which purine and pyrimidine bases were bonded to the silica gel.[30] With this support, base-pairing interactions between the nucleic acid base pairs and the modified silica gel were expected to improve resolution in nucleic acid separation. Although such stationary phases were used to separate nucleic acid free-bases, purine alkaloids, nucleosides, and mono- and oligonucleotides, this approach unfortunately had least success with oligonucleotide separation, which is the most important area. Thus, there was still a critical need for improved solid supports that would effectively separate nucleotides and oligonucleotides.

The inventors realized that for a solid support to be most useful, it must not only separate similar nucleotides and oligonucleotides from one another, it must do so rigorously and correctly based on chain length or size. Unfortunately, prior to the present invention, there were no suitable phosphate chelating agents which made this an achievable goal for use in either HPLC or electrophoretic separation systems. As described below, the inventors designed and constructed sapphyrin-based supports and used them to achieve the separation of nucleotides and oligonucleotides, thus overcoming many of the existing drawbacks described above.

A further utility of such sapphyrin-substituted materials is their use as tools in the removal of phosphorylated environmental contaminants from ground water, soil, foodstuffs, and the like. They may therefore be employed to analyze and separate pesticides such as Dichlorovos, Phosphamidon, Diazanon, and Parathion,[36] herbicides and fungicides, many of which contain organophosphorus compounds. Sapphyrin-substituted gels and columns may even be employed in the rapid detection and analysis of organophosphorus chemical warfare agents, allowing them to be disposed of where necessary.[37]

Another technical area in which significant improvements could be made is in oligonucleotide analysis. For example, automated gene sequencing is currently carried out using either radio- or fluorescent-labeled nucleic acid gel electrophoresis.[23] This technique is limited by the requirement for either slab or tubular polyacrylamide gels. An alternative approach, currently being considered on a research basis, is to use capillary electrophoresis.[31,32] Unfortunately, this is limited when it comes to achieving separations based purely on electrostatics and oligomer size. A technique which would allow for such separation would therefore represent a significant improvement in this area.

As outlined above, the present invention therefore encompasses, but is not limited to, the following four or five groups of novel sapphyrin-based molecular structures: (I) water soluble sapphyrins; (II) sapphyrin-metal chelating conjugates; (III) sapphyrin-nucleobase conjugates; (IV) oligomeric and polymeric sapphyrin derivatives, a sub-group of which can be independently termed group (V), the polymer-supported sapphyrins and chromatographic supports containing sapphyrin and other expanded porphyrins linked to polymers such as polyacrylamide, polystyrene, glass, clays, zeolites, silica gel or Merrifield resins. The water soluble sapphyrins include sapphyrin hydroxyalkylamide and sugar derivatives. The sapphyrin-nucleobase conjugates include an extensive group of structures in which nucleobase-like recognition units are appended directly into the phosphate-chelating sapphyrin core. The polymer group broadly comprises both group IV, the oligomers and polymers of sapphyrin or sapphyrin derivatives and sapphyrin-nucleotide oligomers and polymers with various linkages, and group V, the polymer supported expanded porphyrin constructs.

In addition, it will be understood that the synthetic strategies developed by the inventors, wherein a functionalized sapphyrin is appended to a moiety of desirable chemical function, can be used to prepare an extremely wide variety of sapphyrin-containing conjugates. Sapphyrins may thus be conjugated to, not only metal chelating agents, sugars, nucleobases, and other sapphyrins, sapphyrin derivatives, or polysapphyrins, but also to a variety of other substances. These include, for example, phosphates, phosphonates, sulfates, sulfonates, amino acids, peptides, polypeptides, steroids, steroid derivatives, alkylating agents, and polymers glasses or solids, such as agarose and sepharose, polyacrylamide, controlled pore glass, silica gel, Merrifield resin, polystyrene, clays or zeolites. It is contemplated that one of skill in the art will be able to prepare sapphyrin conjugates including those listed above, without undue experimentation, given the extensive synthetic methodology disclosed throughout the present application

I. WATER SOLUBLE SAPPHYRIN DERIVATIVES

Water soluble porphyrin and porphyrin-like derivatives, especially sapphyrin derivatives, are of potential interest in a variety of applications ranging from photodynamic therapy (PDT) to DNA recognition and modification to cellular recognition and transport. The present inventors considered that the development of water soluble sapphyrin-based compounds without ionizable groups would likely be advantageous in a number of these applications.

In regard to PDT, water soluble sapphyrins may be used as photosensitization agents for the photodynamic inactivation of infectious agents having membranous envelopes. As such they may be employed in the photoeradication of cell-free viruses from blood samples, such as, for example, the hepatitis viruses HBV and NANB, and especially HIV-1. In this process, sapphyrin localizes selectively at or near the morphologically characteristic viral envelope. Upon photoradiation, it catalyzes the formation of highly reactive singlet oxygen which, in turn, destroys the essential membrane envelope, thus killing the virus and eliminating its infectivity, see U.S. Pat. No. 5,041,078, incorporated herein by reference.

The search for compounds for use in in vivo cellular transport and uptake, where diffusion across a membrane is involved, led the inventors to synthesize and characterize a range of novel water soluble sapphyrin derivatives. Generally speaking, the water soluble sapphyrin derivatives of this invention will include at least four OH groups, such as can be supplied by a variety of different polyhydroxy groups, or a single sugar residue. This broad class of water soluble sapphyrins can be further divided into water soluble polyhydroxysapphyrins and water soluble sapphyrin sugar derivatives. These groups include a variety of distinct molecules, such as, for example, the compounds represented by structures 1 and 3–6 (FIG. 2), and substituted derivatives thereof.

Naturally, those of skill in the art will understand that a wide range of water soluble sapphyrins are encompassed by the present invention. Both a variety of polyhydroxysapphyrins and sapphyrin sugar derivatives may be synthesized according to the methodology disclosed herein. For example, any one, or more, of the many sugar and modified sugar units depicted in Table 1 may be linked to a sapphyrin core to create a water-soluble sapphyrin in accordance herewith.

A. Water Soluble Polyhydroxysapphyrins

These are water soluble sapphyrin derivatives based on two (poly)hydroxyalkylamido units attached to the macrocyclic periphery. Examples of compounds of this type include those represented by structures 1 and 3 (FIG. 2). Although, naturally, it will be understood that a wide variety of different, and yet analogous, substituted derivatives may be prepared in accordance herewith. Polyhydroxysapphyrins may be prepared from an activated form of a sapphyrin acid (acid chloride, mixed anhydride, O-acylurea derivative, N-acylimidazole) and polyhydroxyamines.

B. Water Soluble Sapphyrin-Sugar Derivatives

The second general group of water soluble sapphyrin derivatives are the sapphyrin-sugar derivatives, where any one of a number of various sugar subunits are connected to the macrocycle periphery. Specific examples of this type of compound are represented by structures 4 & 6 (FIG. 2). Again, in light of the present disclosure, those of skill in the art will be able to prepare a wide variety of distinct sapphyrin-sugar derivatives without undue experimentation. Examples of sugars and sugar-derivatives which be employed in accordance herewith are listed in Table 1. The sugars employed may be either D or L forms and may also be either α or β anomeric forms. The use of modified sugars is also envisioned, such as those including, for example, phosphate, methyl or amino groups. It is contemplated that preferred sugars for use in accordance herewith will include, for example, glucose, glucosamine, galactose, galactosamine and mannose.

TABLE 1

Examples of Sugars and Sugar Derivatives

| | |
|---|---|
| Ribose | Fructose |
| Arabinose | Sorbose |
| Xylose | Tagatose |
| Lyxose | Fucose |
| Allose | |
| Altrose | Methylglucoside |
| Glucose | Glucose 6-phosphate |
| Mannose | |
| Gulose | N-Acetylgalactosamine |
| Idose | N-Acetylglucosamine |
| Galactose | Sialic Acid |
| Talose | |
| Ribulose | |
| Xylulose | |
| Psicose | |

For example, the efficiency of those compounds shown in Structures 4c and 6b for singlet oxygen generation has already been tested, when it was found to be 11% (in comparison with $ZnTPPS_4$). These water soluble sapphyrins 4c and 6b thus have apparent utility as a potential cellular targeting agent. As is generally known, glycoconjugates have important roles in the control of cell division and intercellular association. Changes in the biochemical and organizational structures occur during malignant transformation[15]. Therefore it may be therapeutically advantageous to alter or inhibit the biosynthesis of these tumor cell surface constituents. This might result in tumor cell death caused by the inhibition of the biosynthesis of vital membrane components. In this regard, D-glucosamine derivatives have been proven to be efficient inhibitors of tumor growth[16].

It is envisioned that differential tumor toxicity and specific organ targeting can be achieved with different sugar-sapphyrin derivatives. For instance, modified sugars such as e.g., Glc-NAc can be included within the image of substituents that can be appended to the sapphyrin core. All that would be needed is to start with an activated sapphyrin and 2-acetamido-2-deoxy-3,4,6-tri-O-acetyl-β-D-glucopyranosylamine. The synthesis and use of this and other related systems are thus considered to fall within the scope of the present invention.

The synthesis of representative compounds 4 and 6 involve compounds that are connected via glycoside bonds and obtained starting from dihydroxysapphyrin and α-D-acetobromoglucose, as precursors, and using silver triflate in dichloromethane to effect coupling. The second set of systems is connected via amide bonds. These later materials are obtained starting from sapphyrin(bis)acid chloride and 1,3,4,6-tetra-O-acetyl-2-amino-2-deoxy-α-D-glucopyranose (tetraacetyl-D-glucosamine). In both series, after removing the protecting groups from the sugar moieties, the desired water soluble sapphyrin derivatives may be obtained.

It is contemplated that compounds such as those represented by structures 4 and 6 will have utility in both photophysical and biological embodiments. For example, it is envisioned that these new sapphyrins will have improved solubility and/or phosphate anion chelation properties, rendering them of use in protocols such as anti-viral transport and RNA/DNA recognition and binding.

II. SAPPHYRIN-CHELATING CONJUGATES

The second general group of novel monomeric sapphyrin derivatives of the present invention are the sapphyrin-metal chelating derivatives. Suitable chelating groups contemplated for use in such conjugates include, but are not limited to, EDTA, EGTA, DTPA, DOTA, ethylene diamine, bipyridine, 1,10-phenanthralene, crown ether, aza crown and catechols.

A specific example of this type of sapphyrin derivative is the sapphyrin-EDTA conjugate represented by structure 8 (FIG. 3B). The inventors have demonstrated that, in the presence of $Fe^{2+}$ and dithiothreitol, this molecule, in micromolar concentrations, can cleave DNA. Sapphyrin-EDTA conjugates will therefore be useful in effecting affinity cleavage of double stranded DNA. It is particularly contemplated that they will be of use in cleaving double stranded DNA of a defined sequence, or more importantly, perhaps will cleave double stranded DNA with a particular structural motif.

The sapphyrin-EDTA conjugate is believed to bind to DNA in a novel manner, based generally upon binding to the phosphate residues of the sugar-phosphate backbone. As such, it is contemplated that this sapphyrin conjugate will be capable of sensing conformational changes about the DNA back-bone. Sapphyrin-EDTA will thus be particularly useful as a structural probe of DNA, and the sapphyrin-metal chelating derivatives in general will be of use in a variety of photophysical embodiments.

III. SAPPHYRIN NUCLEOBASE DERIVATIVES

The inventors initially found that organic-solubilized, 2',3',5'-tris(triisopropylsilyl)-substituted nucleosides would enhance the through-$CH_2Cl_2$ transport of the corresponding Watson-Crick complementary phosphate-free nucleoside in a standard 3-phase Aq I-$CH_2Cl_2$-Aq II liquid membrane cell.[14] They also reported that the deproteinated form of sapphyrin, a pentapyrrolic "expanded porphyrin",[2,3,4a,6] acts as an efficient but non-selective carrier for nucleotide monophosphates at pH<4.[5] Rubyrin[17], and a large excess of C-Tips (ca. 100-fold) was also found capable of effecting the selective through-transport of GMP at neutral pH (C-Tips is 2',3',5'-tris(triisopropylsilyl)-cytosine).

However, sapphyrin, which remains monoprotonated in the ca. $3.5 \leq pH \leq 10$ regime,[5,18] was itself found to be ineffective as a GMP carrier at pH 7, even in the presence of a large excess of C-Tips.[18] Thus, it was thought that if sapphyrin-based systems were to be made effective as neutral-regime carriers, it would require the construction of sapphyrin systems in which nucleotide recognition units are "appended" directly onto the phosphate-chelating expanded porphyrin core.

Precisely these types of sapphyrin derivatives have now been synthesized and form an important part of the present invention. These sapphyrin nucleobase conjugates are molecules which have been derivatized by the addition of one or more nucleobase compounds, i.e., one or more purines, pyrimidines, or derivatives thereof. Sapphyrin derivatives with one nucleobase per sapphyrin molecule may be referred to as ditopic receptors, whereas those with 2 nucleobases per molecules are termed tritopic receptors.

Sapphyrin mononucleobase derivatives may include any of the naturally-occurring purine or pyrimidine nucleobases, namely, cytosine, guanine, thymidine, adenine or uridine. Equally, they may include modified versions of any of these, such as the heterocyclic components of those nucleoside/nucleotide analogues listed in Table 2 and phosphorylated version of the compounds listed therein.

TABLE 2

MODIFIED NUCLEOSIDE/NUCLEOTIDE ANALOGUE ANTI-METABOLITES

AraC
AraAMP
Azaribine

TABLE 2-continued

MODIFIED NUCLEOSIDE/NUCLEOTIDE ANALOGUE
ANTI-METABOLITES

Azathioprine
Azauridine
AZT
Bromodeoxyuridine
Chlorodeoxyuridine
Cytarabine
Deoxyuridine
Dideoxycytidine ddC
Dideoxylnosine ddI
Erythrohydroxynonyladenine
Floxuridine
Fluorouracil (5-FU)
Idoxuridine
LOMPD
Mercaptopurine
PFA
Thioguanine
Trifluoromethylde-oxyuridine
Xylo-GMP Also included within the invention are the sapphyrin mononucleobase derivatives including chemically modified nucleobase such as "protected" bases. Protecting groups are used to protect reactive groups, such as amino and carboxyl groups, from inappropriate chemical reactions. Sapphyrin-nucleobase conjugates with protected bases include, for example, conjugates wherein one or more base has a protecting group, such as 9-fluorenylmethylcarbonyl, benzyloxycarbonyl, 4-methoxyphenacyloxycarbonyl, t-butyloxycarbonyl, 1-adamantyloxycarbonyl, benzoyl, N-triphenylmethyl or N-di-(4-methoxyphenyl) phenylmethyl on the amino group of the nucleobase.

As clearly detailed in the description of the figures, any of the groups $R^1$–$R^{10}$ may be H, alkyl, alkene, alkyne, halide, alkyl halide, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, aldehyde, ether, ketone, carboxylic acid, phosphate, phosphonate, sulfate, phosphate substituted alkyl, phosphonate substituted alkyl, or sulfate substituted alkyl; with at least one of these R groups being: $(CH_2)_n$—A—$(CH_2)_m$—B, wherein A may include any of the groups listed above and B will be one or more nucleobases, nucleobase derivatives or protected nucleobases.

Conjugation of a nucleobase to a sapphyrin derivative to form a mononucleobase sapphyrin conjugate may be via any of the R groups $R^1$–$R^{10}$. Conjugation of the two separate nucleobases to a sapphyrin derivative to form a dinucleobase sapphyrin conjugate may also be via any two of the R groups $R^1$–$R^{10}$. However, it is contemplated that the creation of a symmetrical molecule, such as by substitution on $R^4$ and $R^7$, or $R^5$ and $R^6$, will be generally be preferred.

Specific examples of sapphyrin mononucleobase derivatives are represented by structures 9–15 (FIGS. 4A-1 through 4A-6). These include, but are clearly not limited to, the cytosine-containing sapphyrin derivative represented by structure 10; and the guanine-containing sapphyrin compounds 12, 14 & 15. The doubly substituted sapphyrin analogues, or tritopic sapphyrin receptors, of this invention may contain any combination of nucleobases. These sapphyrin derivatives may be homonucleobase conjugates, containing two of the same bases, or heteronucleobase constructs containing two distinct nucleobases in any combination. Thus, for example, in the nomenclature used herein, a sapphyrin nucleobase derivative with a single cytosine residue is represented by structure 10; a sapphyrin nucleobase derivative with two guanine residues is represented by structure 18, and a sapphyrin nucleobase derivative with one guanine residue and one cytosine residue is represented by structure 16.

These sapphyrin nucleobase monomers will act as selective carriers for the through-membrane transport of nucleotide monophosphates at biological, i.e. near-neutral pH. Thus, a sapphyrin nucleobase derivative bearing a cytosine residue will function in the binding and transport of GMP, and likewise, each nucleobase conjugates will be able to effect the transport of its complementary base, i.e., the base with which it naturally base-pairs. The nucleobase conjugates will be particularly useful for the transport of nucleotide derivatives, such as acyclovir monophosphate, Xylo-GMP and Ara-AMP, phosphonate derivatives and simple species such as the pyrophosphate derivatives PFA and COMDP, each of which function as antiviral agents.

For initial studies, ditopic and tritopic sapphyrin receptors bearing one and two cytosine molecules were first synthesized. The ditopic receptor is represented by structure 10 (FIG. 4A-2), and the tritopic receptor by structure 20 (FIG. 4B-4). These sapphyrin nucleobase derivatives were prepared by trifluoroacetic acid (TFA) induced detritylation of protected conjugates. The protected conjugates in question are those wherein the nucleobase derivative contains, instead of a single hydrogen, a $C(C_6H_5)_3$ group. These, in turn, were prepared by coupling 1-(2-aminoethyl)-4-[(triphenylmethyl)amino]-pyrimidin-2-one[19] with the appropriate sapphyrin mono- or diacid chlorides.

The inventors have also prepared a variety of sapphyrin nucleobase conjugates by the condensation of sapphyrin mono and bis acids with conveniently modified nucleobases. Various spacers may be used for the connection, such as, for example, oligomethylene bridges with terminal amino, or hydroxy function, which allow formation of amide and ester bond for the connection of the sapphyrin and nucleobase units. This bridge may also be modified, e.g., by the reduction of the amide bond to give the amine function.[19] Satisfactory spectroscopic and analytic data have been obtained for all such new compounds. The present invention thus encompasses many possibilities for the connection of the same or different nucleobases to one sapphyrin macrocycle.

Transport studies, using a standard[20] Aq I-$CH_2Cl_2$-Aq II liquid membrane cell, were carried out using the sapphyrin cytosine conjugates represented by structures 10 and 20. It was found that both 10 and 20 were able to effect the selective through-membrane transport of GMP at, or near, neutral pH (Table 3). In all cases, compound 20 displayed a higher selectivity for GMP, by a factor of 8–100, relative to either AMP or CMP, than its congener 10.

These results clearly demonstrate that the transport of a normally organic-insoluble species, namely guanosine-5'-monophosphate (GMP), can be effected by preparing and using an appropriate sapphyrin-nucleobase conjugate. A similarly designed sapphyrin receptor approach may be used to achieve the into-cell in vivo delivery of other nucleotides and nucleotide derivatives, such as, for example, Xylo-GMP and other antiviral nucleotide-based drugs.

As described in detail below, any of the sapphyrin mono-di- or oligo-nucleobase conjugates and derivatives, including both naturally-occurring nucleobases and modified nucleobases, may also be linked to a solid support to form a polymer-supported sapphyrin composition.

IV. OLIGOMERIC AND POLYMERIC SAPPHYRIN DERIVATIVES

A further group of novel sapphyrin-based compounds embodied by the present invention is the sapphyrin oligomer and polymer group. For convenience, this group can be sub-divided into two further groups, one of sapphyrin-only oligomers and polymers or sapphyrin-conjugate and sapphyrin-nucleobase oligomers and polymers; and another of sapphyrin- and expanded porphyrin-based solid supports, including chromatographic supports and columns.

The first group of sapphyrin oligomers and polymers include relatively low-number conjugates, such as dimers and trimers, and also larger oligomers or polymers. The oligomers will generally include between about 4 or 5 and about 30 or 40 residues, or even up to about 50 residues, whereas the polymers may generally comprise from about 40 or 50 to about 100 or 150 residues, or even up to about 200 sapphyrin units or even more where desired.

The monomeric units employed in the synthesis of sapphyrin-sapphyrin conjugates may be known sapphyrin molecules, such as those described in U.S. Pat. No. 5,159,065, incorporated herein by reference. Equally, any of the novel sapphyrin derivatives disclosed herein may be employed, in any combination, to create further novel sapphyrin dimers, trimers, oligomers or polymers. Encompassed within the terms oligomers or polymers are those sapphyrin conjugates synthesized by the controlled addition of particular monomeric units and those produced by more uncontrolled polymerization methods.

Due to the unique mode of DNA interaction, sapphyrin polymeric molecule will possess an unrivaled ability to act as a general DNA binding platform. This has the distinct advantage that it can be modified so as to adjust both target cell specificity and degree of interaction with the DNA. For sapphyrins and sapphyrin polymers, the basic site of interaction with the DNA involves the interior of the sapphyrin macrocycle, so that the exterior positions $R_1$-$R_{10}$ can be substantially modified without significantly disrupting the DNA binding interaction. These exterior positions can be used to systematically adjust features such as solubility, membrane permeability and cell selectivity. Furthermore, groups designed to modulate interaction with DNA can be attached to the exterior of the sapphyrin polymers including alkylating functions (bromoacetamido groups, ethylene diamine, epoxides etc.) to provide covalent attachment to DNA or ene-diyne moieties to allow for double stranded cleavage.

A further and important advantage of the sapphyrin system is that the simple DNA binding motif has been extended to several multimeric structures, in which multiple sapphyrins covalently linked together will be able to bind simultaneously and thus strengthen the entire interaction. This feature will allow a modular approach in which the appropriate number (2–10) of sapphyrin molecules is attached in a single molecule, perhaps with different sapphyrin units containing sapphyrin derivatives with different groups attached that control such important properties such as solubility, target cell specificity and DNA modification ability.

A. Sapphyrin oligomers

Specific examples of sapphyrin oligomers include, but are not limited to, those compounds represented by the structures 21–24 of FIGS. 5B-1 through 5B-4. Sapphyrin oligomers were been prepared by the condensation of sapphyrin mono and bis acids with amino groups as spacers units. As di- and tri-amino spacers, ethylenediamine, 1,3-diaminopropane, 1,3- and 1,4-phenylenediamine, diaminonaphtalenes and anthracenes, for example, have used in the synthetic approach. Sapphyrin trimers were built in one step reaction, in which 3 molar equivalents of sapphyrin mono acid were combined with a trisamino component, e.g. tris (aminoethyl)amine, in very high yield.

For the coupling reaction, a variety of different methods have been used. These include, for example, acid chloride, O-acylurea, mixed anhydride and N-acylimidazole, which were found to be particularly successful. The synthetic methodology employed was essentially the same as that developed to prepare sapphyrin-nucleobase conjugates. It is important to emphasize that the synthesis of both the sapphyrin nucleobase conjugates and the sapphyrin oligomers and polymers may be readily performed using a standard automated oligonucleotide synthesizer.

The present inventors have prepared mono- di- and tri-sapphyrins and have proven them to be very efficient recognition species for nucleotides, monophospates, diphosphates and triphosphates. The formation of noncovalently bonded complexes between sapphyrin-like oligomers and a nucleotide allows the transport of nucleotide mono, di and triphosphates across cell membranes to occur at physiological pH. This will likely be of direct use in the transport of antiviral triphosphates to mammalian cells, especially for the treatment of AIDS.

As discussed above, any of the novel sapphyrins of the present invention may be employed, in any combination, in the synthesis of novel sapphyrin oligomers or polymers. The synthetic approach developed is equally suitable to the use of one or more novel sapphyrin derivatives as starting materials as it is to the use of known sapphyrins. Importantly, methods are disclosed herein for the generation of covalently bonded sapphyrin-nucleotide complexes. Importantly, the sapphyrin-sapphyrin nucleobase and sapphyrin-DNA linkage chemistry of the present invention is compatible with automated oligonucleotide synthesis, and phosphoramidate chemistry.

The present invention encompasses two categories of sapphyrin polymers; these may be described generally as polymeric sapphyrins and polymer supported sapphyrins (see below, group V). The polymeric sapphyrins may be employed in a variety of different embodiments, for example, relating to oligonucleotide binding and transport, as will be discussed more fully below. The polymer supported sapphyrin group includes resin-synthesized sapphyrins. These sapphyrin polymers may ultimately be cleaved, resulting in the generation of a free polymer. However, following resin-bound synthesis, the polymers may be maintained covalently bound to the parent resin, thus opening further possibilities for their use.

Sapphyrin polymers which are maintained bound to the parent resin may be advantageously employed as a "column material" for use in chromatography, for example, in the separation of nucleotides or in photoactivation. With regards to the latter, it is to be appreciated that polymer-supported sapphyrins could prove particularly advantageous for the in vitro inactivation of viruses and other blood borne pathogens: the fact that no sapphyrin would be left in the blood (or other substance) being purged would militate against any toxicity problems.

B. Polymeric Sapphyrins

One class of sapphyrin polymers contemplated by the present invention are those compounds resulting from the polymerization of monomeric units, by various types of processes other than those using a resin. For example, radical polymerization of olefin substituted sapphyrin may be employed to give a polyethylene type of polymer. Alternatively, polycondensation of sapphyrin bis acid with sapphyrin diamine could be used to give a polyamide type of polymer, or polycondensation of sapphyrin bis acid with sapphyrin bis alcohol may be employed resulting in a polyester type of polymer. In all of these cases, sapphyrin-based polymers may be prepared both with and without covalently bonded nucleobases. Examples of the latter are 26A and 26B.

V. POLYMER-SUPPORTED EXPANDED PORPHYRINS AND DERIVATIVES

The finding that certain expanded porphyrins bind to phosphate moieties led the inventors to propose that sapphyrins or rubyrins, when linked to a solid support, may be advantageously employed to purify complex mixtures of phosphorylated species. Such expanded-porphyrin solid supports were particularly envisioned to be suitable for use in the improved separation of nucleotides and oligonucleotides. This indeed proved to be the case and has given rise to the fifth broad group of novel expanded porphyrins of the present invention, namely polymer-supported rubyrin and sapphyrin constructs. The solid support or matrices of these constructs may be any of a variety of materials such as polyacrylamide, polystyrene, glass, clays, zeolites, silica gel, Merrifield resins and other materials that can be functionalized by those skilled in the art of chemical synthesis.

In the following discussion, the polymer-supported expanded porphyrins will generally be exemplified by those containing sapphyrin, as set forth by general Structure VII. However, it will be understood that both the concepts and the synthetic methodology presented herein can be readily adapted for use with rubyrin and rubyrin derivatives, as in general Structures VI. The synthesis and use of rubyrin, rubyrin derivatives and rubyrin conjugates is detailed in U.S. Ser. No. 08/015,208, incorporated herein by reference.

A. Sapphyrin-Substituted Silica Gels and Merrifield Resins

In certain embodiments, the polymer-supported expanded porphyrins of the present invention will be bonded, sapphyrin-substituted glass capillaries or silica gels that will serve as specific, phosphate-chelating solid supports. These may be used in the chromatographic and electrophoretic separation of phosphorylated species, including nucleotides, oligonucleotides, and DNA or RNA molecules including gene fragments, and will be suitable for both analytical and preparative HPLC applications.

Figure 5D:
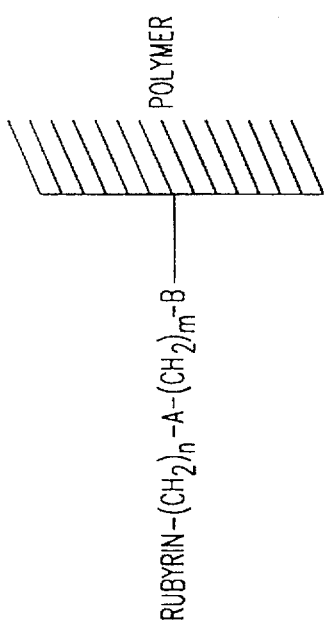
Figure 1:
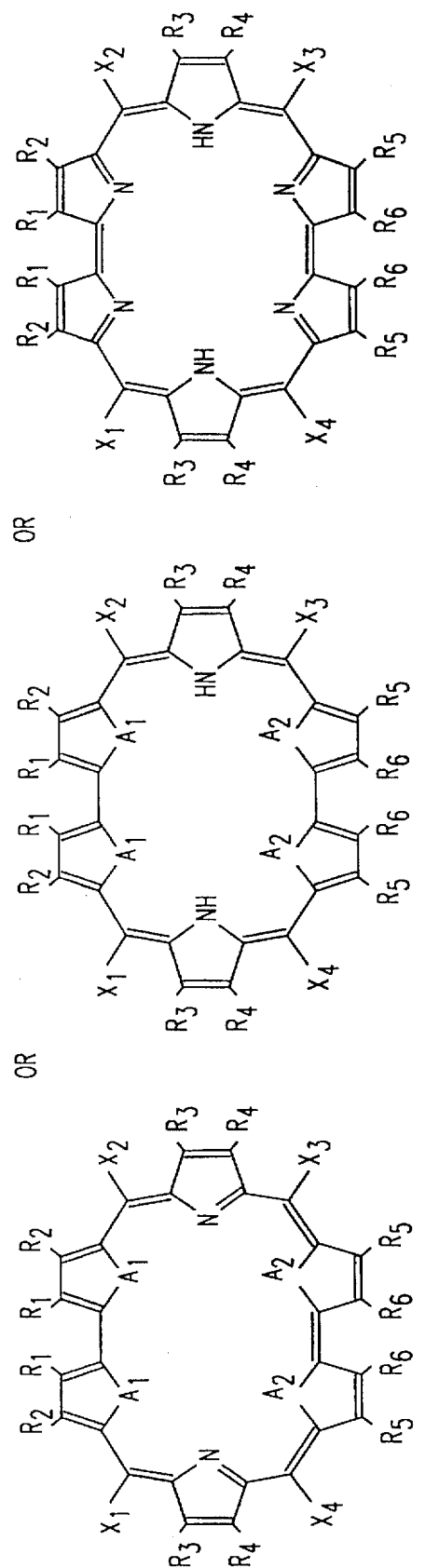
Figures 2, 5D:
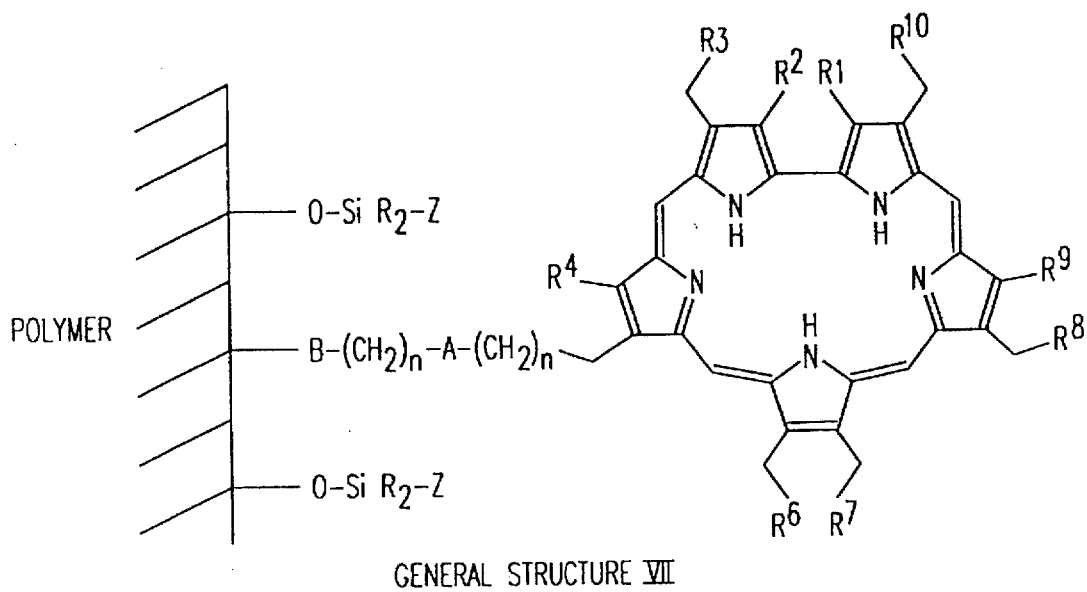
Figures 3, 5D:
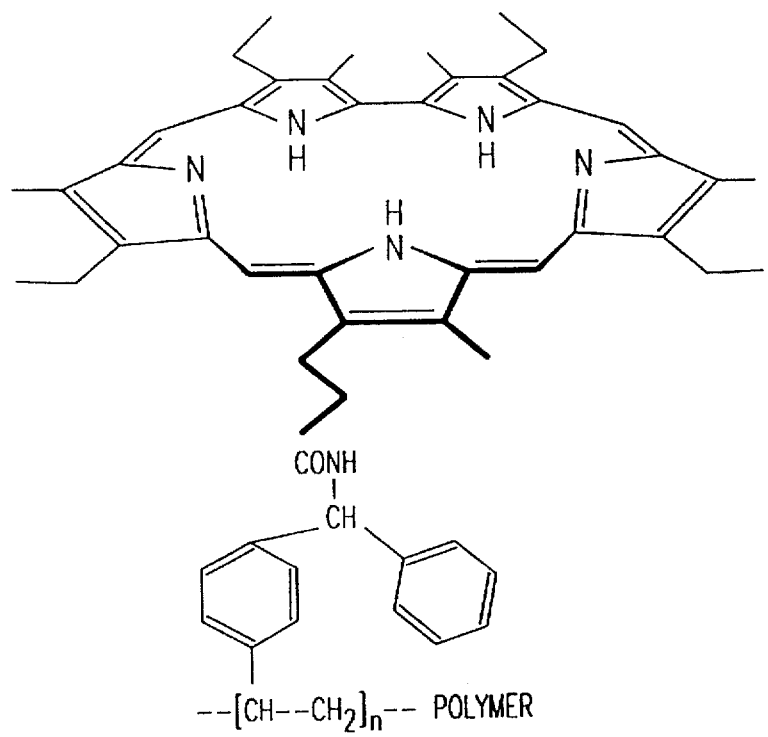
Figures 4, 5D:
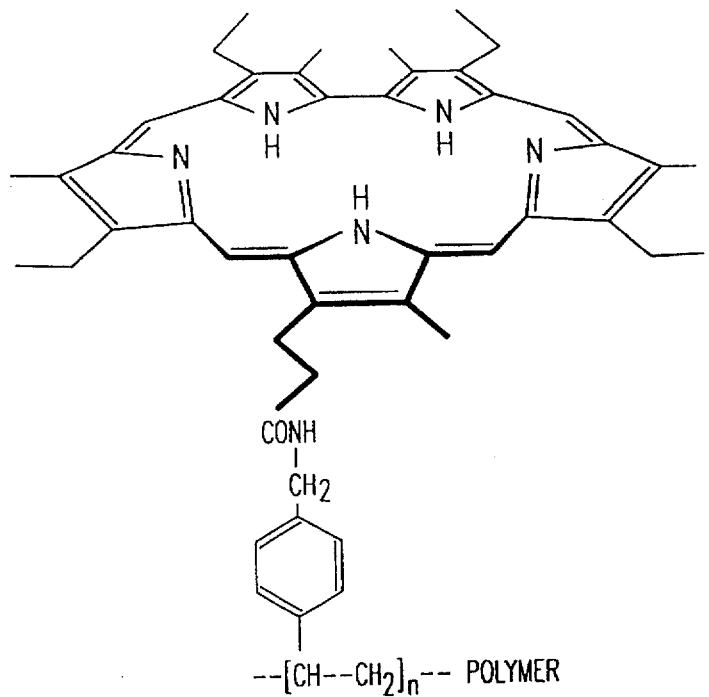
Figures 5, 5D:
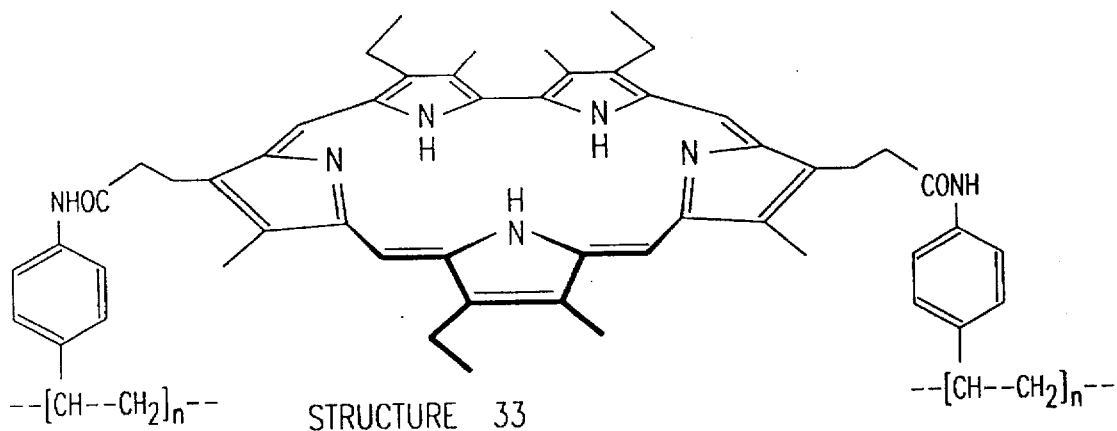
Figures 5, 5D, 6:
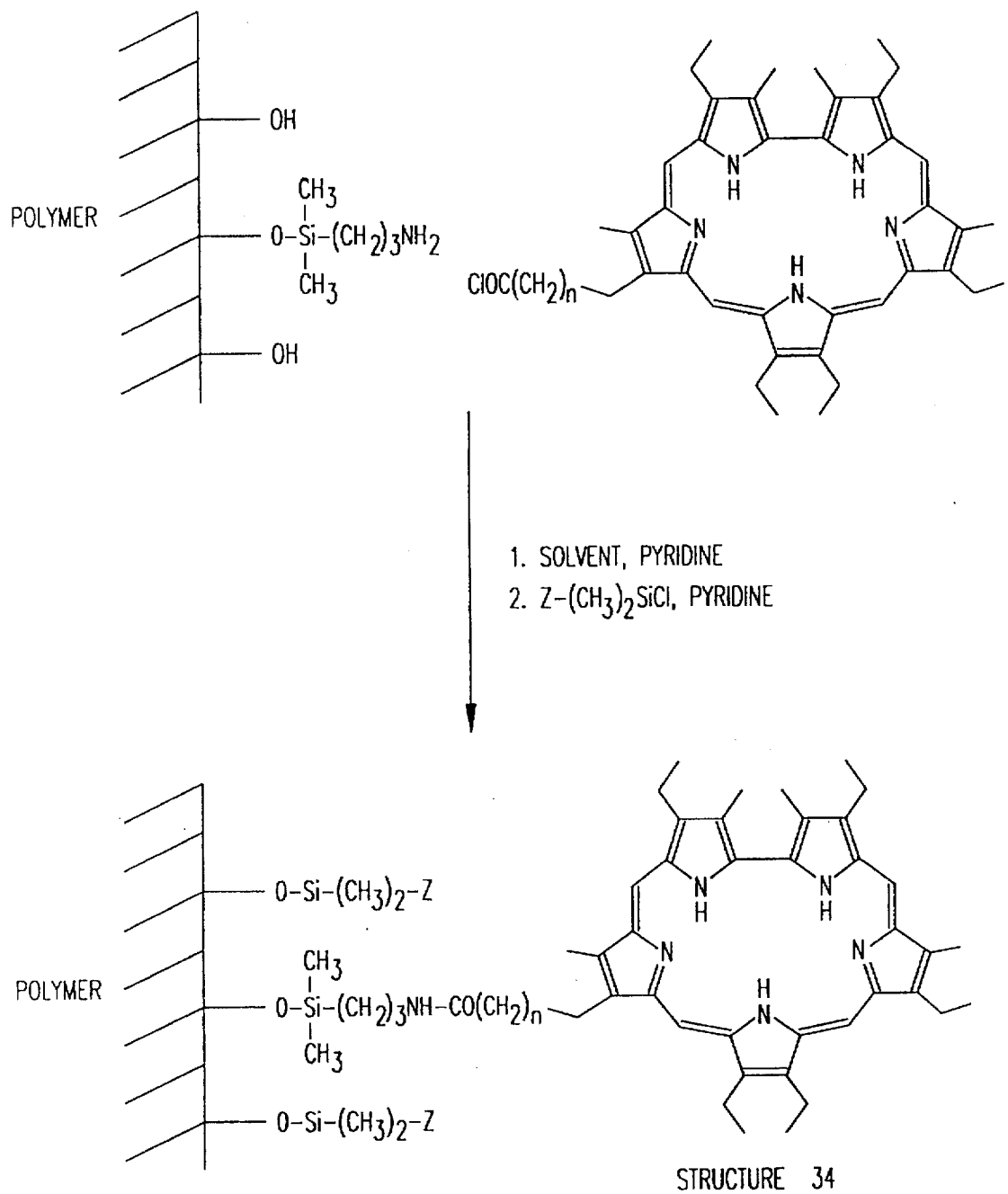
Figures 5, 5D, 6, 7:
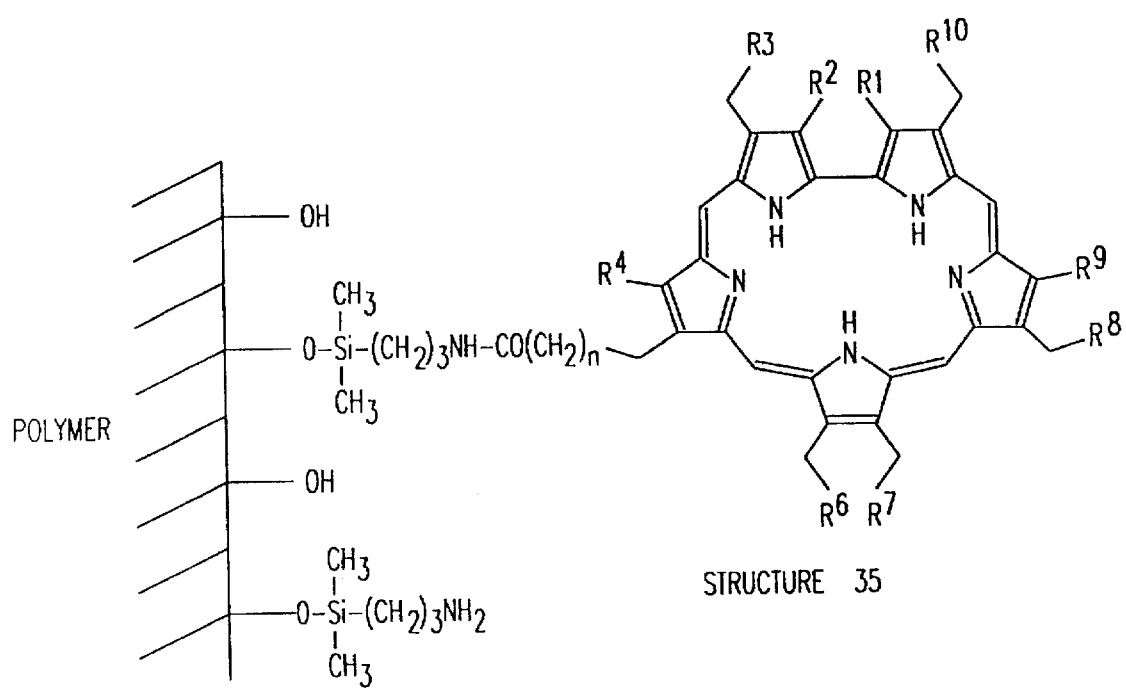
Figures 5, 5D, 6, 7, 8:
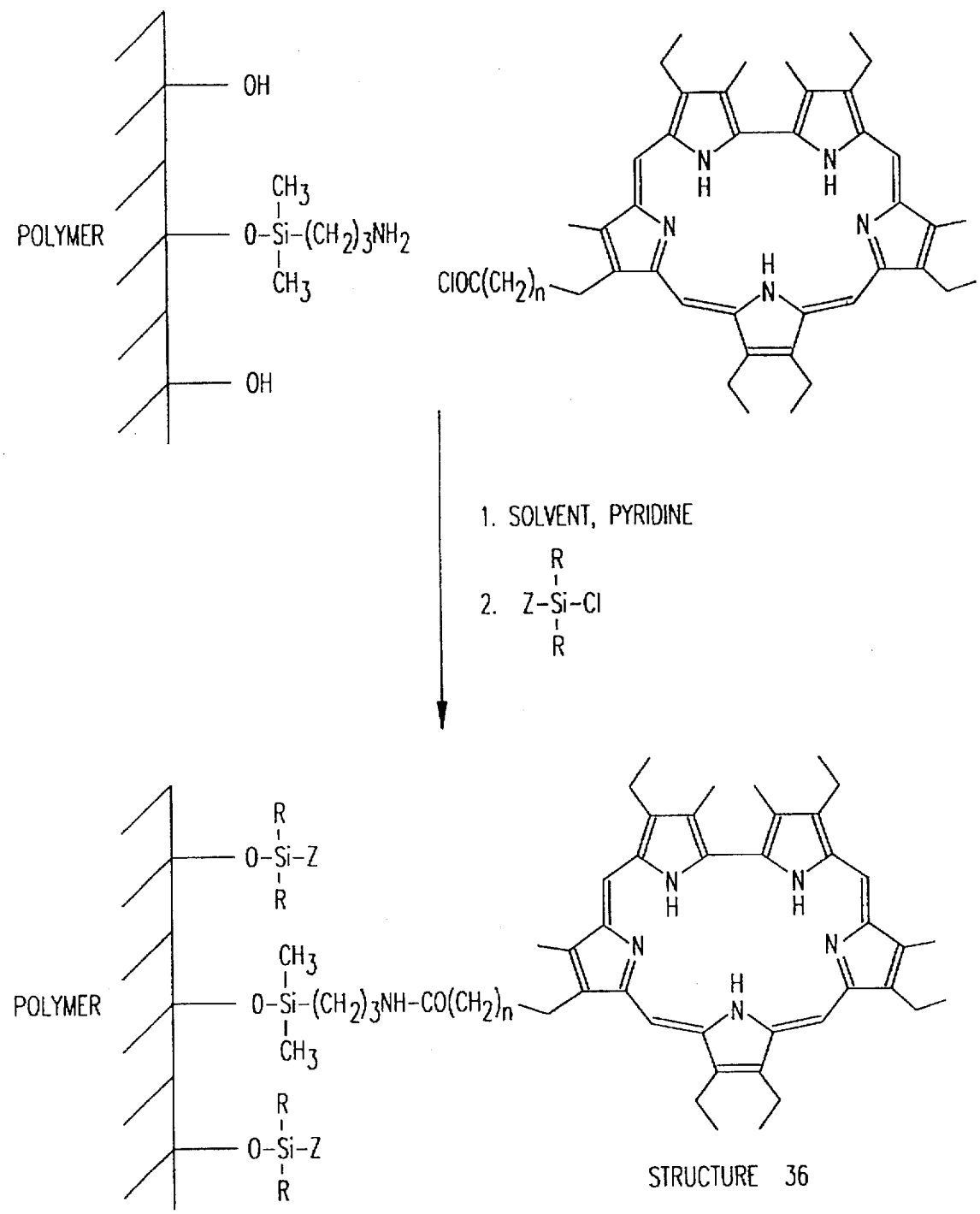
Figures 5, 5D, 6, 7, 8, 9:
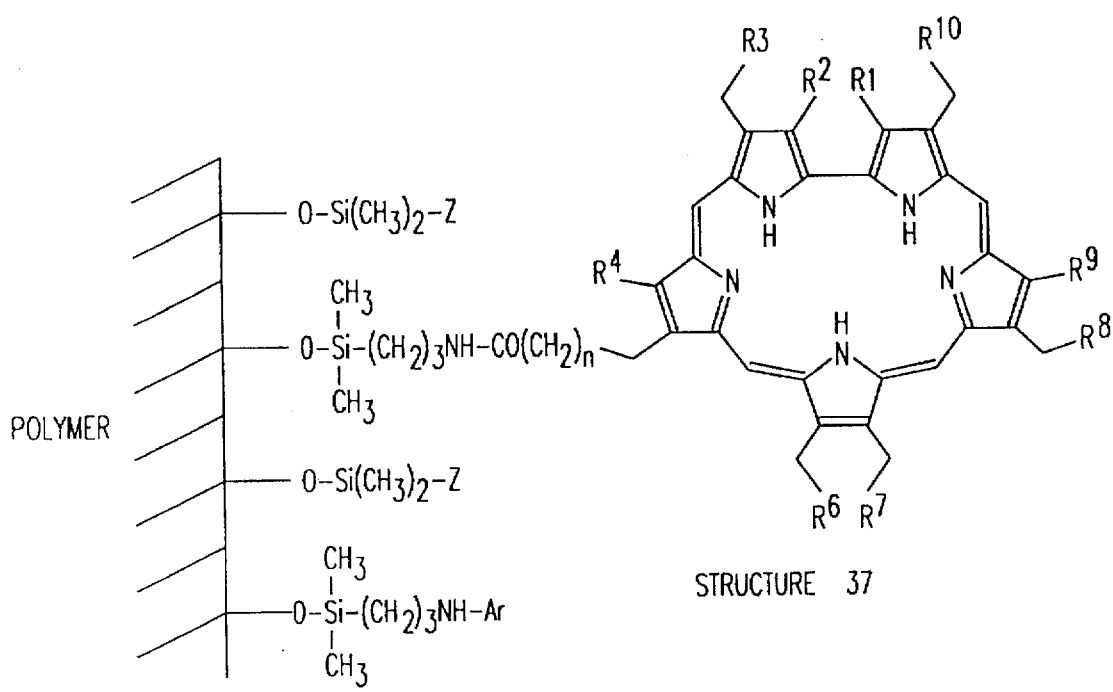
Figures 5, 5D, 6, 7, 8, 9, 10:
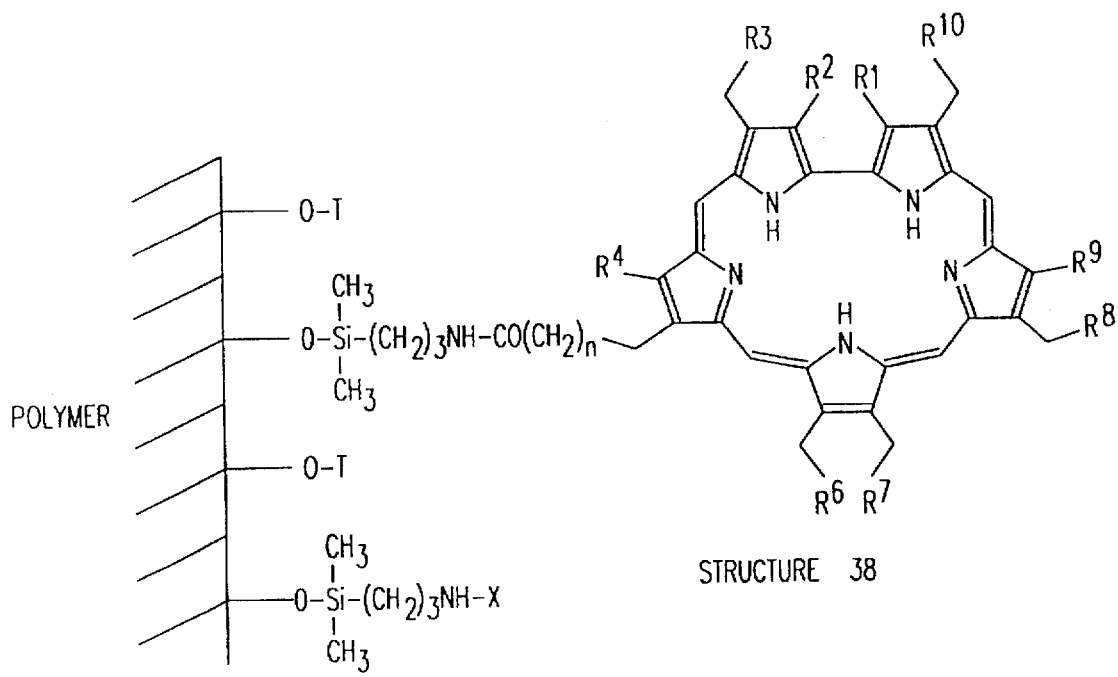
Figure 6:
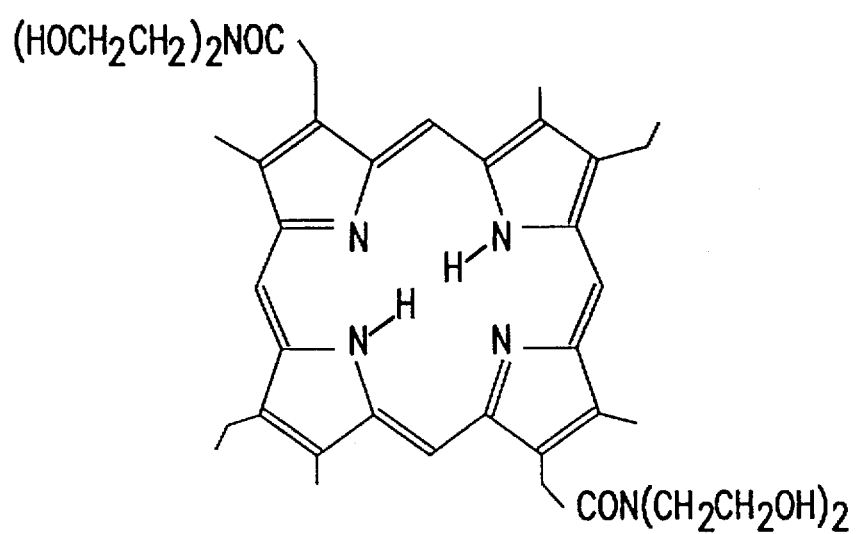

These aspects of the invention therefore encompass a full range of sapphyrin-modified stationary phases in accordance with the generalized Structure VII set forth in FIG. 5D-2. When the bonded stationary phase (termed "polymer" in the figures) is silica gel, the resulting products will be used for medium to high pressure applications. For low pressure applications, organic polymer based sapphyrins, for example, modified Merrifield resins, will be prepared using the same basic strategy. In all cases the wide range of intrinsic variation, imparted via groups Z and the expanded porphyrin R groups such as $R^8$, will afford the opportunity to prepare stationary phases capable of separating a wide range of phosphorylated species.

To date, a sapphyrin substituted Merrifield resin and a first generation sapphyrin-substituted silica gel which correspond to structure 34 have already been prepared. In the sapphyrin-substituted silica gel 34, $R^8$=H and Z=CH$_3$. With this latter silica gel, a 4.6 mm×10.0 cm HPLC column was packed (by Alltech Inc). Then, in the initial series of studies, this column was used to separate various, adenosine-derived nucleotide mono-, di-, and triphosphates with significant success (FIGS. 7A-i, 7A-ii and 7B).

The ability to separate nucleotide mono-, di-, and triphosphates from cell extracts has long been a challenging task. Most of the commercially available HPLC columns provide less than adequate separation of di- from triphosphates.[28,29] However, such separations are instrumental in determining cell energy charge (eq. 1), which is used as an indicator of cell health in the study of many diseases.[33] The successful results shown in FIGS. 7A-i, 7A-ii and 7B are therefore particularly important.

$$\text{Adenylate Energy Charge} = \frac{[ATP] + 0.5\ [ADP]}{[AMP] + [ADP] + [ATP]} \quad (1)$$

A great advantage afforded by these aspects of the invention is that different numbers of sapphyrin molecules may be introduced per polymer unit simply by varying the molar ratio of sapphyrin derivative to the number of the groups bonded on polymer surface. The inventors therefore also propose to vary the micromolar concentration of sapphyrin used per gram of silica gel in order to control the retention times and to influence peak shape characteristics. Straightforward modifications such as these will thus allow such systems to be used in both analytical and preparative modes.

In addition to the separation of nucleotides, as described above, the inventors have also achieved the separation of oligonucleotides using the same first-generation column, 34. They have been able to effectively separate a commercially-obtained (Sigma Chemical Co.) mixture of adenosine-derived 2-, 3-, 4-, 5-, 6-mers, 7-mers, 8-mers and 9-mers (FIGS. 8A-i, 8A-ii and 8B). These results are particularly remarkable as, not only was the separation of the 2-, 3-, 4-, 5-6-, 7-, 8- and 9-mers readily achieved, but that various impurities present in the commercially available mixture were also distinguished. Indeed, the presence of contaminants in this supposedly pure mixture was later confirmed at source (Sigma Chemical Co.). Furthermore, it was found by the inventors that separation at these 2- through 9-mers could be achieved in less than one hour.

Thus, it is clear that these new chromatographic supports are suitable for use in analyzing and purifying a large number of critical products, including small molecule antiviral agents and oligonucleotides such as hybridization probes and primers. They already represent a marked advance over existing technology including PAGE, HPLC, HPAC, ion exchange columns and purine and pyrimidine base-bonded silica gels,[30] and are expected to find many immediate applications in DNA-related biotechnology and medicine.

Such expanded porphyrin polymeric supports are also contemplated for use in separating very large RNA or DNA molecules such as gene fragments and antisense constructs. In order to achieve separation of higher order oligonucleotides, the inventors envision that various elution-related parameters, such as, e.g., flow rate, buffer strength, and sapphyrin-to-silica loading level, may be optimized so as to achieve the best possible separations. Second and/or third generation polymer-supported expanded porphyrins may also be prepared for use in connection with RNA or DNA separation and purification.

B. Second and Third Generation Sapphyrin Solid Supports

The preparation of improved, i.e., second and third generation, expanded porphyrin solid supports is also contemplated. Such new systems will be designed to separate phosphorylated compounds based upon other specific binding modes in addition to the phosphate recognition provided by the expanded porphyrin moiety. For example, hydrophobic interaction separation is contemplated, and can be provided by modifying the length of alkyl chains employed. Recognition mediated by Watson-Crick hydrogen bonding interactions is also contemplated. This may be achieved by using expanded porphyrin-nucleobase conjugates, by appending nucleobases onto the solid support itself, or by using a combination of both methods. Introduction of aromatic ring (phenyl, substituted phenyl) or amino or silanol groups gives the possibility for π—π stacking interactions.

The second generation stage of this new synthetic development may be considered to be the stage of long chain alkyl addition. Long chain alkyl groups will thus be introduced onto the surface of the sapphyrin-substituted silica-gel. This will result in columns that will combine the properties of both reverse phase separation and sapphyrin-based phosphate chelation and ion exchange. Further, in light of the existing theories of HPLC[34], the inventors contemplate using appropriate synthetic modifications to optimize the retention characteristics of the columns so that they separate selectively any desired length of oligonucleotide and/or gene fragment.

The yet superior third-generation systems contemplated by the inventors are those in which the stationary phases will combine the best features of three different known modes of separation: hydrogen bonding, electrostatics, and reverse phase hydrophobicity. This will be achieved by using various different substituents on both the expanded porphyrin molecules and on the stationary phase material itself (e.g., Z and $R^8$ groups).

For example, in certain embodiments, the Z or $R^8$ groups may be varied so as to introduce a nucleobase or nucleobase analog. Such nucleobase-bearing systems[30,35] are expected to act in conjunction with the combined sapphyrin electrostatic and reverse phase hydrophobic interactions described above. Thus, by this triple combination, it is expected that the resultant solid phase will be able to separate nucleotides and oligonucleotides not only on the basis of charge and length but also on the basis of nucleic acid type. Such phases, of course, would prove to be of tremendous value in applications involving the analysis and purification of gene fragments since these are often of similar size but of very different chemical (i.e., nucleic acid) composition.

These same third generation phases would also be of tremendous benefit in the separation and analysis of AZT phosphate, dideoxycytidine phosphate, and other prodrugs used in the asymptomatic treatment of HIV and other viral infections. Here, in particular, it would be of significant value to have access to an analytical method that would allow one to distinguish the active phosphorylated nucleotide analogs from naturally occurring phosphorylated products, such as AMP or GMP, since this would allow for facile, on-line clinical analysis.

C. Sapphyrin Substituted Capillary Electrophoresis

In still further embodiments, the inventors also contemplate using polymer-supported expanded porphyrins in connection with capillary electrophoresis (CE). In CE, unlike HPLC, no solid silica or Merrifield resin support is used. Rather, differential adherence to the glass surface of a capillary is used to effect separation.[31] Thus, in this embodiment, sapphyrin-modified glass capillary surfaces will be prepared and used for improved CE resolution. In these embodiments, the polymer in any of the structures 31 to 38 will be an untreated glass capillary rather than silica gel. Since glass is chemically similar to silica gel (both are silicate-derived), the preparation of a range of modified glass surfaces, as represented by structures 31 to 38 can be straightforwardly achieved in light of the present disclosure.

Such sapphyrin-glass constructs may be used to separate natural and synthetic nucleotides and oligonucleotides. Here, as above, the best combination of Z and $R^8$ groups needed to effect any given type of separation will be determined. The information gained using silica gels will be applied in these considerations and supplemented by further straightforward studies. It is expected that this will lead to a significantly improved new CE system. To highlight the utility of such a system, the inventors contemplate carrying out a Sanger sequencing of pBR322 using fluorescently labeled dideoxy nucleotides (Applied Biosystems Inc.). Since an entire range of fragment sizes is produced here, this will allow the superiority of the new sapphyrin-based approach to be quickly demonstrated.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. For example, other macrocyclic, positively-charged entities can be envisioned as binding to phosphate-containing species such as nucleotides, oligonucleotides and DNA by means of the same or similar oriented electrostatic interactions described herein.

EXAMPLE 1

SYNTHESIS OF POLYHYDROXYSAPPHYRINS

A. Preparation of 3,12,13,22-tetraethyl-8,17-bis{[tris(hydroxymethyl)methylamino]-carbonylethyl}-2,7,18,23-tetramethylsapphryin, structure 3

Sapphyrin bis acid structure 2a (66 mg, 0.1 mmol) was dissolved in dry tetrahydrofuran (20 ml) and 1,1'-carbonyldiimidazole (33 mg, 0.2 mmol) was added and solution was stirred at room temperature for 1 hour. A solution of tris(hydroxymethyl)aminomethane (24.2 mg, 0.2 mmol) in 3 ml of water was added. The reaction mixture was stirred for 12 hours then imidazole was filtered off, the solvent was evaporated in vacuo and the product crystallized from mixture methanol-dichloromethane (1:10), the yield of product 3 was 73 mg (81.5%).

FAB MS m/e (rel. intensity) 896 (100, $[M]^+$), 897 (60, $[MH]^+$).

HRMS: Calcd. $C_{50}H_{69}N_7O_8$ 895.52072. Found 895.52099. UV/VIS ($H_2O$):$\lambda_{max}$ 412,622,673.

B. Preparation of 3,12,13,22-Tetraethyl-8,17-di(hydroxypropyl)-2,7,18,23-tetramethylsapphyrin, structure 5

4,4'-Diethyl-5,5'-diformyl-3,3'-dimethyl-2,2'-bipyrrole (544 mg, 2.0 mmol) and 2,5-bis (5-carboxyl-3-hydroxypropyl-4-methypyrrol-2-ylmethyl)-3,4-diethylpyrrole (1.02 g, 2.0 mmol) were dissolved in absolute ethanol (2 L) under heating. The reaction mixture was allowed to cool to room temperature and p-toluenesulfonic acid monohydrate (1.5 g) was added. The air was vigorously bubbled through reaction mixture for 4 days. The ethanol was then removed on rotorary evaporator and product was isolated by column chromatography on silica gel with dichloromethane with 1–5% of methanol. Bis hydrochloride salt was prepared by washing of dichloromethane solution of sapphyrin with 1N HCl and gave a yield of product of 1.151 g (78.0%).

$^1$H NMR for 5. 2HCl: (300 MHz, $CDCl_3$) δ: −4.93 (2H,s,NH), −4.63 (1H,s,NH), −4.30 (2H,s,NH), 2.07 (6H,t, $CH_2CH_3$), 2.76 (4H, pentet, $CH_2CH_2CH_2OH$), 4.03 (6H,s, $CH_3$), 4.06 (4H,t,$CH_2CH_2CH_2OH$), 4.20 (6H,s,$CH_3$), 4.59 (4H,q,$CH_2CH_3$), 4.68 (4H, q,$CH_2CH_3$), 4.77 (4H,t, $CH_2CH_2CH_2OH$), 11.59 (2H,s,meso-H), 11.66 (2H,s,meso-H); $^{13}$C NMR (80 MHz, $CDCl_3$) δ: 13.15, 16.19, 17.84, 19.14, 21.85, 21.94, 25.04, 36.94, 62.25, 91.17, 97.53, 127.30, 128.38, 128.77, 131.77, 133.65, 134.46, 138.63, 140.54, 142.26, 143.88; Vis $\lambda_{max}$(MeOh) (log ε), 443 (5.36), 573 (3.26), 618 (3.81), 669 (3.83)

HRMS FAB calcd for $C_{42}H_{55}N_5O2Cl_2 \cdot H_2O$: C,67.19; H,7.65; N,9.33; Cl,9.44. Found: C,67.25; H,7.61; N,9.41; Cl,9.35.

C. Preparation of 3,12,13,22-Tetraethyl-8,17-bis[di(hydroxyethyl)aminocarbonylethyl]-2,7,18,23-tetramethylsapphyrin, structure 1

3,12,13,22-Tetraethyl-8,17-bis(carboxyethyl)-2,7,18,23-tetramethylsapphyrin 2a (69 mg, 0.1 mmol) was dissolved/suspended in dry dichloromethane (30 ml) and 0.5 ml oxalylchloride and 1 drop of DMF was added under argon. The reaction mixture was stirred at room temperature for 3 hours, then evaporated to dryness. Sapphyrin bis acid chloride was dissolved in dry dichloromethane (20 ml) and slowly added under argon to the solution of diethanolamine (52.5 mg, 0.5 mmol) in dry dichloromethane (30 ml), (or tetrahydrofrane, 30 ml) which also contained 5 mg of 4-dimethylaminopyridine and 0.2 ml pyridine. Reaction mixture was stirred at room temperature for 24 hours and then evaporated to dryness, 30 ml of 1M NaOH added, stirred for 10 min, precipitated product was filtered off, washed with cold water (30 ml), dried, crystallization from ethanol-hexane (1:3). Free base sapphyrin is not soluble in water; conversion to freely water soluble hydrochloric acid salt was made by adding 3 ml of 5% HCl and evaporation. Crystallization from ethanol-hexane (1:3) gave 75 mg (80.12%) of product 1 as bis chloride salt.

$^1$H NMR 1 (300 MHz, CDCl$_3$) ∂: −5.13 (2H,s,NH),−4.95 (1H,s,NH), −4.78 (2H,s,NH), 2.00 (6H,t,CH$_2$CH$_3$), 3.26 (8H,m,NCH$_3$), 4.18 (6H,s,CH$_3$), 4.47 (4H,q,CH$_2$CH$_3$), 5.02 (4H,t,CH$_2$CH$_2$CON), 11.58 (2H,s,meso-H), 11.61 (2H,s, meso-H).

$^1$H NMR 1 free base (300 MHz, CDCl$_3$ with 10% CD$_3$OD) ∂: 1.98 (6H,t,CH$_2$CH$_3$), 2.11 (6H,t,CH$_2$CH$_3$), 3.13 (4H,t,CONCH$_2$CH$_2$), 3.42 (4H,t,CH$_2$CH$_2$CON), 3.59 (8H, t,CH$_2$CH$_2$OH), 3.91 (6H,s,CH$_3$), 4.09 (6H,s,CH$_3$), 4.39 (4H, q,CH$_2$CH$_3$), 4.57 (4H,s,CH$_2$CH$_3$), 4.94 (4H,t, CH$_2$CH$_2$CON), 11.16 (2H,s,methine, 11.18 (2H,s,methine).

$^{13}$C NMR (75 MHz, CDCl$_3$ with 10% CD$_3$OD) ∂: 12.46, 15.59, 16.02, 16.51, 17.76, 18.46, 20.52, 20.56, 23.23, 35.50, 36.39, 37.02, 51.63, 59.63, 60.67, 60.74, 75.66, 90.27, 90.50, 90.91, 97.94, 127.17, 130.88, 135.74, 136.07, 137.14, 137.53, 142.55, 142.69, 172.98.

FAB MS m/e (rel. intensity) 862 (98, [MH]+), 863 (78, [MH$_2$]+), 861 (56, [M]+).

HRMS Calcd for $C_{50}H_{68}N_7O_6$: 862.520676. Obds 862.523102 UV/VIS (H$_2$O, pH 7.0): $\lambda_{max}$ 400.5 (5.01), 623.0 (3.75) 672.0 (3.62)

Anal. Calcd for $C_{50}H_{67}N_7O_6 \cdot H_2O$: C,68.23; H,7.83; N,11.17. Found: C,68.11; H,7.85; N,11.04. Calcd. for $C_{50}H_{67}N_7O_6 \cdot 2HCl$: C,64.23; H,7.44; N,10.49; Cl,7.58. Found: C,64.12; H,7.61; N,10.52; Cl,7.38.

D. Preparation of 8,18-diethyl-3,13-bis[di(hydroxyethyl)aminocarbonylmethyl]-2,7,12,17-tetramethylporphyrin, structure 39

3,13-bis(carboxymethyl)-8,18-diethyl-2,7,12,17-tetramethylporphyrin (5 mmol) was converted to bis(p-nitrophenyl ester). Bis(p-nitrophenyl ester) of porphyrin diacid (106 mg, 0.1356 mmol) was added under argon to dry pyridine (150 ml) at 55° C., followed by diethanolamine (104 mg, 1 mmol). The reaction mixture was stirred for 4 days at 55° C. under argon in the dark. The pyridine was then removed in vaccuo, 25 ml of 0.1N NaOH was added, stirred for 15 min, the product filtered off, washed with cold water (5 ml) and dried. The porphyrin is freely soluble in acidic condition (bellow pH 5). Conversion to bishydrochloric salt: 5% HCl (10 ml, 5%) was added and evaporated to dryness, crystallization from water (pH adjusted to 8, compound precipitate from solution). Porphyrin 5.2 HCl is freely soluble in water. Product for elemental analysis was obtained by precipitation from water after adding solution of NaHCO$_3$, washing (water) and dryed.

$^1$H NMR (300 MHz, CDCl$_3$, with 3% TFA): δ−3.99 (4H,bs,NH) 1.72 (6H,t,CH$_2$CH$_3$), 4.04 (4H,q,CH$_2$CH$_3$), 5.53 (4H,s,CH$_2$CON), 10.62 (2H,s,methine), 10.81 (2H,s, methine).

$^{13}$C NMR (80 MHz, CDCl$_3$, TFA): δ 11.37, 11.98, 16.48, 19.86, 31.58, 51.73, 59.37, 59.89, 98.10, 99.48, 112.26, 135.84, 138.11, 140.11, 141.04, 141.84, 142.23, 143.71, 158.65, 159.17, 171.62.

FAB HRMS Calcd for $C_{40}H_{54}N_6O_6$ 714.410484., obsd 714.411287; Calcd for $C_{40}H_{53}N_6O_6$ 713.402659, obsd 713.400834. UV-Vis (H$_2$O, pH 1): $\lambda_{max}$ 400.0

Anal. Calcd for $C_{40}H_{54}N_6O_6 \cdot 2H_2O$: C,63.98; H,7.79; N,11.19. Found: C,64.07; H,7.84; N,11.22.

EXAMPLE 2

SYNTHESIS OF SAPPHYRIN DIGLYCOSIDES

Sapphyrin mono and diglycosides were prepared by the glycosylation of sapphyrin alcohols with α-D-acetobromoglucose and α-D-acetobromogalactose with a silver catalyst. The most advantageous catalyst was found to be silver triflate, although silver tetrafluoroborate and silver carbonate also gave very good results. With polyalcohols it is possible to determine the conversion to glycosides by the molar ratio alcohol-halogenose/silver catalyst. The inventors were able to introduce 1 or 2 sugar units as a function of the molar ratio of hydroxy groups/halogenose/silver catalyst.

A. Preparation of 8,17-di(tetraacetate-α,β-D-glucopyranoxypropyl)-3,12,13,22-tetraethyl-2,7,18,23-tetramethylsapphyrin, structure 4A.

3,12,13,22-Tetraethyl-2,7,18,23-tetramethyl-8,17-di(hydroxypropyl) sapphyrin structure 5 (132 mg, 0.2 mmol) was dried with silver triflate (0.2569 g, 1 mmol) and barium carbonate (0.5 g) for 2 hours at 20° C./1.32 mm Hg in apparatus equipped with septum. The apparatus was flushed with argon (2×) and dry dichloromethane (50 ml) was added through the septum. After dissolution, the mixture was cooled to −45° C. and solution of α-D-glucopyranosylbromide tetraacetate (0.411 g 1 mmol) in dichloromethane (20 ml) was gradually added through septum under stirring. The reaction mixture was stirred at −45° C. for 1 hour, then allowed to warm to room temperature with exclusion if light and stirred for 8 hours. The reaction mixture was diluted with 50 ml of dichloromethane, filtered with celite, the filtrate was washed with saturated solution of sodium hydrogencarbonate and water, dried over sodium sulfate and solvent was evaporated. Pure product was obtained by column chromatography on silica gel with dichloromethane with 4% of methanol as a eluent. The yield of product 4a was 250 mg (94.7%).

$^1$H NMR spectrum (300 MHz, CDCl$_3$): δ −6.21–6.07, −5.81, −5.75, 2.03, 2.05, 2.11, 2.13, 2.16, 2.28, 2.31, 3.09, 4.11, 4.17, 4.24, 4.33, 4.51, 4.53, 4.72, 4.74, 5.29, 11.59, 11.66.

FAB MS, m/e (rel. intensity): 1321 (90, [MH]$^+$), 1322 (56, [MH$_2$]$^+$), 1320 (45, [M]$^+$).

HRMS Calcd. for $C_{70}H_{89}N_5O_{20}$ 1319.6100. Found 1320.617916 ([MH]$^+$).

The same experimental procedure was used for the preparation of tetraacetylgalactose and tetraacetylmannose substituted sapphyrins. In these cases, the sugar unit was varied using the same protecting group.

B. Preparation of 8,17-di(tetrabenzoate-α,β-D-glucopyranoxypropyl)-3,12,13,22-tetraethyl-2,7,18,23-tetramethylsapphyrin, structure 4B.

The same procedure as for tetraacetylderivative with α-D-glucopyranosylbromide tetrabenzoate (0.660 g, 1 mmol) gave product 4b in 97.6% yield.

FAB MS m/e (rel. intensity):1817 (95, [MH]$^+$), 1818 (67, [MH$_2$]$^+$), 1816 (62, [M]$^+$). HRMS Calcd. for $C_{110}H_{105}N_5O_{20}$ 1815.7346. Found 1816.743117 ([MH]$^+$)

C. Preparation of 8,17-di(α,β-D-glucopyranoxypropyl)-3,12,13,22-tetraethyl-2,7,18,23-tetramethylsapphyrin, structure 4c.

The product was prepared from protected derivatives (acetyl, benzoyl) by splitting of protecting group in methanol with a catalytic amount of sodium methoxide, or potassium hydroxide, or potassium cyanide. Pure product was obtained by crystallization, or reverse phase chromatography ($C_{18}$-modified silicagel) with methanol as a eluent. The yield of product 4c was 67%.

FAB MS m/e (rel. intensity):986 (70, [M]$^+$), 987 (56, [MH]$^+$).

HRMS Calcd. for $C_{54}H_{75}N_5O_{12}$ 985.54108. Found 985.5417. Elemental analysis: calc. 65.77% C, 7.67% H, 7.10% N; found 65.65% C, 7.69% H, 7.04% N.

UV/VIS (H$_2$O): $\lambda_{max}$ 416,597.5, 642,712; (MeOH): $\lambda_{max}$ 445.

EXAMPLE 3

SYNTHESIS OF SAPPHYRIN BIS (GLYCOSAMIDES)

Sapphyrin bis(glycosamides) were prepared by condensation of an activated form of the above-described sapphyrin acid (acid chloride, mixed anhydride, O-acylurea, N-acylimidazole derivative) with free, or O-acetylated glycoamines (2-amino-2-deoxy-glucopyranose, mannopyranose, galactopyranose).

A. Preparation of 3,12,13,22-Tetraethyl-8,17-bis[1,3,4,6-tetra-O-acetyl-2-amino-2-deoxy-α,β-D-glucopyranose)-carbonylethyl]-2,7,18,23-tetramethylsapphyrin, structure 6A Sapphyrin bis acid structure 2a (69 mg, 0.1 mmol) was converted to bis acid chloride as previously described. Bis acid chloride was dissolved in dry dichloromethane under argon and slowly added to the solution of 1,3,4,6-tetra-O-acetyl-2-amino-2-desoxy-α-D-glucopyranose (0.1736, 0.5 mmol) in dichloromethane, which also contained 10 mg of 4-dimethylaminopyridine and 0.5 ml of dry pyridine at room temperature. The reaction mixture was stirred for 14 hours, then washed with water, the organic layer was evaporated and the product obtained by column chromatography on silica gel with dichloromethane containing 2–10% methanol as an eluent. The yield of product 6a was 114.6 mg (85.0%).

$^1$H NMR spectrum (300 MHz, CDCl$_3$): δ=−4.91, −4.59, 1.94, 2.06, 2.12, 2.27, 3.41, 3.689, 3.84, 3.91, 3.93, 4.05, 4.12, 4.22, 4.54, 4.63, 4.72, 5.04, 5.19, 5.22, 11.59, 11.69.

FAB MS, m/e (rel. intensity):1347 (96, [M]$^+$), 1348 (84, [MH]$^+$).

HRMS: Calcd. $C_{70}H_{89}N_7O_{20}$ 1347.61428. Found 1347.61624.

B. Preparation of 3,12,13,22-Tetraethyl-8,17-bis[(2-amino-2-deoxy-α,β-D-glucopyranose)-carbonylethyl]-2,7,18,23-tetramethylsapphyrin, structure 6b The above-described acetylated sapphyrin derivative 6a (13.4 mg, 0.01 mmol) was dissolved in methanol (10 ml) and a solution of 3 mg KOH in methanol was added. The reaction mixture was stirred for 4 hours and then the pH adjusted to 6 by adding hydrochloric acid. After evaporating to dryness, the product was crystallized from methanol-dichloromethane (1:1), or obtained by reverse phase chromatography with methanol as eluent. The yield of product 6b was 10.38 mg (88.0%).

FAB MS, m/e (rel. intensity): 1012 (76, [MH]$^+$), 1011 (54, [M]$^+$).

UV/VIS (H$_2$O): $\lambda_{max}$ 413,621,671.

Deacetylation could also be achieved under basic conditions by using, e.g., NH$_3$ in methanol, sodium methoxide in methanol, DABCO in methanol, or KCN in methanol, each with good yields.

EXAMPLE 4

SYNTHESIS OF SAPPHYRIN-EDTA CONJUGATE (STRUCTURE 8)

One example of the sapphyrin-metal chelating conjugates of the present invention is sapphyrin-EDTA. To a solution of diethylenetriamine (22.0 ml, 210 mmol) in 200 ml of dry dichloromethane at 0° C., was added triphenylmethylchoride (1.8 g, 6.5 mmol) and the solution was warmed to room temperature with stirring overnight. The organic layer was washed 1M NaOH (200 ml×3), dried with Na$_2$SO$_4$, and the solvent was removed by rotary evaporation. Purification on silica gel using methanol/dichloromethane yielded 2.1 g (94%) of a viscous oil that gave a positive test using ninhydrin.

$^1$H NMR δ (CD$_2$Cl$_2$) 2.27 (2H, t, ø$_3$CNHCH$_2$CH$_2$), 2.55 (2H, t, ø$_3$CNHCH$_2$CH$_2$), 2.70 (4H, m, RNHCH$_2$CH$_2$NH$_2$), 7.23–7.65 (15H, m, aromatic-H's), $^{13}$CNMR δ (CDCl$_3$) 41.5, 43.1, 49.9, 42.1, 70.7, 126.1, 127.7, 128.4, 146.1; MS FAB, [MH]$^+$:m/z 346; HRMS, [MH]$^+$: 346.2278 (calcd for $C_{23}H_{28}N_3$:346.2283).

Tert-butyl bromoacetate (1.3 ml, 8.5 mmol), tritylated diethylenetriamine (4, 0.89 g, 2.6 mmol), K$_2$CO$_3$ (1.18 g, 8.5 mmol), and Cs$_2$CO$_3$ (1.69 g, 5.2 mmol) in 15 ml of acetonitrile were stirred at 0° C. overnight. The inorganic salts were removed by vacuum filtration, and the solvent was removed by rotary evaporation. Purification on silica gel using dichloromethane/hexanes yielded 1.2 g (68%) of a light yellow oil:

$^1$H NMR δ (CD$_2$Cl$_2$) 1.41 (9H, s, ø$_3$CNRCH$_2$CO$_2$C(CH$_3$)$_3$), 1.44 (18H, s, N(CH$_2$CO$_2$C(CH$_3$)$_3$)$_2$) 2.21 (2H, t, ø$_3$CNRCH$_2$), 2.62 (2H, t, ø$_3$CNRCH$_2$CH$_2$), 2.72 (4H, m, NRCH$_2$CH$_2$NR$_2$), 3.11 (2H, s, CH$_2$CH$_2$NRCH$_2$CO$_2$t-butyl), 3.36 (4H, s, N(CH$_2$CO$_2$t-butyl)$_2$), 7.17–7.51 (15H, m, aromatic H's); $^{13}$ CNMR: δ (CDCl$_3$) 27.9, 28.1, 41.1, 52.6, 52.8, 54.5, 55.0, 55.6, 56.1, 70.6, 80.8, 126.1, 127.7, 128.7, 146.3, 170.6, 170.9 (one quaternary carbon missing); MS FAB, [MH]$^+$: 688.5; HRMS, [MH]$^+$:688.4323 (calcd for $C_{41}H_{58}N_3O_6$:688.4326).

The tritylated amine (120 mg, 0.2 mmol) and palladium black (150 mg) were stirred in 5.0 ml of methanol for 16 hours under an atmosphere of hydrogen gas. The palladium metal was removed by vacuum filtration and the solvent removed by rotary evaporation. Purification on silica gel using methanol/chloroform yielded 50 mg (64%) of a yellow oil:

$^1$H NMR: δ (CDCl$_3$) 1.42 (27H, s, CO$_2$C(CH$_3$)$_3$), 2.14 (2H, b, NH$_2$), 2.69 (4H, m, H$_2$NCH$_2$CH$_2$), 2.77 (4H, m, RHNCH$_2$CH$_2$NR$_2$), 3.27 (2H, s, CH$_2$CH$_2$NRCH$_2$CO$_2$t-butyl), 3.42 (4H, s, N(CH$_2$CO$_2$t-butyl); $^{13}$CNMR δ (CDCl$_3$) 28.1, 39.9, 52.3, 52.8, 56.1, 57.1, 80.8, 80.9, 170.6, 171.1; MS FAB, [MH]$^+$:m/z 446; HRMS, [MH]$^+$:446.3242 (calcd for $C_{22}H_{44}N_3O_6$:446.3230).

To the sapphyrin mono-carboxylic acid structure 7a (37 mg, 50 μmol) in 20 ml of dry dichloromethane was added one drop of dimethylformamide followed by the cautious dropwise addition of 2.5 ml (5.0 mmol) of a 2.0M solution of oxalyl chloride in dichloromethane. The resulting solution was stirred at room temperature for 4 hours and the solvent was removed under vacuum. The resulting solids were redissolved in 20 ml of dry dichloromethane and 0.1 ml of dry pyridine and the amine (68 mg, 150 μmol) in 20 ml of dry dichloromethane was added dropwise over 1 hour. The reaction was allowed to stir overnight and the solvent was removed under vacuum. Purification on silica gel using methanol/dichloromethane yielded 32 mg of structure 8 as a blue solid (57%). The macrocycle can be further purified by recrystallization from dichloromethane/pentane:

$^1$H NMR: δ (CDCl$_3$) −5.03 (2H, m, NH), −4.57 (1H, s, NH), −4.38 (2H, s, NH), 1.32 (18H, s, CO$_2$C(CH$_3$)$_3$), 1.38 (9H, s, CO$_2$C(CH$_3$)$_3$), 3.29 (2H, s, R$_2$NCH$_2$CO), 3.42 (4H, s, N(CH$_2$CO)$_2$), 3.49 (4H, m, NCH$_2$CH$_2$N), 4.12 (6H, s, CH$_3$) 4.23 (6H, s, CH$_3$), 4.28 (3H, s, CH$_3$), 4.53 (4H, q, CH$_2$CH$_3$), 4.70 (4H, q, CH$_2$CH$_3$), 5.09 (2H, t, CH$_2$CH$_2$CONH), 7.58 (1H, b, CONH), 11.62 (s, 1H, meso-H), 11.70 (s, 2H, meso-H), 11.80 (s, 1H, meso-H); MS FAB, M$^+$: 1057; HRMS, M$^+$: 1056.6790 (calcd for C$_{62}$H$_{88}$N$_8$O$_7$: 1056.6776).

EXAMPLE 5

SYNTHESIS OF SAPPHYRIN DERIVATIVES 7a;7b, FOR USE AS PRECURSORS

The synthesis of the precursor 3,8,17,22-Tetraethyl-12-(carboxyethyl)-2,7,13,18,23-pentamethyl-sapphyrin, structure 7a, is a two part procedure requiring the preparation of the ester 3,8,17,22-tetraethyl-12-(methoxycarbonylethyl)-2, 7,13,18,23-pentamethylsapphyrin, structure 7b and subsequent hydrolysis to the sapphyrin acid of general structure 7a. Ester 7b was prepared in accord with the general optimized procedure for the production of substituted sapphyrins[4]a, incorporated herein by reference. 4,4'-diethyl-5,5'-diformyl-3,3'-dimethyl-2,2'-bipyrrole (272 mg, 1.0 mmol) and 2,5-bis(5-carboxyl-3-ethyl-4-methyl-pyrrol-2-ylmethyl)-3-methoxycarbonylethyl-4-methylpyrrole (523 mg, 1.0 mmol) were condensed to give this desired sapphyrin product in 75.4% yield (0.490 g).

$^1$H NMR (300 MHz, CDCl$_3$): δ=−4.78 (1H, s, NH), −4.76 (1H, s, NH), −4.32 (1H, s, NH), −4.13 (2H, s, NH), 2.35–2.43 (12H, m, CH$_2$CH$_3$), 3.85 (2H, t, CH$_2$CH$_2$CO$_2$CH$_3$), 3.99 (3H, s, CH$_3$), 4.29 (6H, s, CH$_3$), 4.38 (3H, s, CH$_3$), 4.44 (3H, s, CH$_3$), 4.67–4.74 (8H, m, CH$_2$CH$_3$), 5.22 (2H, t, CH$_2$CH$_2$CO$_2$CH$_3$), 11.82 (1H, s, meso-H), 11.85 (1H, s, meso-H), 11.88 (2H, s, meso-H). $^{13}$C NMR (75 MHz, CDCl$_3$): δ=12.7, 13.1, 15.9, 17.8, 17.9, 21.0, 23.0, 37.1, 52.1, 91.5, 92.0, 98.3, 98.4, 126.9, 127.0, 129.5, 129.6, 130.2, 132.7, 132.8, 134.7, 135.3, 135.5, 136.6, 136.7, 137.7, 139.1, 141.5, 141.7, 173.3. HRMS: Calcd. for C$_{41}$H$_{49}$N$_5$O$_2$: 643.3886. Found 643.3887.

The second part of the procedure involves the synthesis of sapphyrin acid 7a which was prepared as follows: a ca. 1:1 v.v. mixture of trifluoroacetic acid and conc. hydrochloric acid (10 ml for 100 mg of starting sapphyrin 7b) was used to hydrolyze the ester. The reaction was run at 50° C. for 2 days after which time the desired sapphyrin acid product was obtained as its bis HCl adduct. After drying in vacuo, this protonated product was purified by column chromatography on silica gel (methanol 5% in dichloromethane, eluent). The yield was ca. 95%. $^1$H NMR (300 MHz, CDCl$_3$): δ=−5.84 (2H, bs, NH), −5.35 (3H, bs, NH), 2.20 (12H, t, CH$_3$CH$_2$), 3.23 (2H, t, CH$_2$CH$_2$CO$_2$H), 4.03 (3H, s, CH$_3$), 4.15 (6H, s, CH$_3$), 4.23 (3H, s, CH$_3$), 4.41 (3H, s, CH$_3$), 4.65 (4H, q, CH$_2$CH$_3$) 4.74 (4H, q, CH$_2$CH$_3$), 4.79 (2H, m, CH$_2$CH$_2$CO$_2$H), 11.42 (2H, s, meso-H), 11.55 (1H, s, meso-H), 11.58 (1H, s, meso-H). $^{13}$C NMR (75 MHz, CDCl$_3$): δ 12.7, 12.9, 14.3, 15.9, 17.7, 17.9, 20.6, 20.9, 22.8, 36.5, 36.7, 61.9, 91.6, 98.1, 120.7, 120.9, 125.4, 125.4, 127.3, 129.1, 129.2, 130.0, 132.7, 132.8, 134.8, 134.9, 135.2, 135.4, 135.6, 135.7, 136.1, 136.8, 136.9, 137.0, 137.7, 139.31, 141.4, 141.8, 141.8, 174.4. FAB MS, m/e (rel intensity): 631 (48, [MH$_2$]$^+$), 630 (100, [MH]$^+$), 629 (52, M$^+$); HRMS: Calcd. for C$_{40}$H$_{47}$N$_5$O$_2$: 629.3730. Found 630.3798 ([MH]$^+$); for C$_{40}$H$_{48}$N$_5$O$_2$ [MH]$^+$: Calcd. 630.3808.

EXAMPLE 6

SYNTHESIS OF SAPPHYRIN MONONUCLEOBASE DERIVATIVES 3,8,17,22-Tetraethyl-12-[2-[1-[2-oxo-4-[(triphenylmethyl)amino]-pyrimidyl]ethyl] aminocarbonylethyl]-2,7,13,18,23-pentamethylsapphyrin, structure 9

Method A: The sapphyrin acid 7a, as prepared above (63 mg, 0.1 mmol), was dissolved in 10 ml of dry dichloromethane under argon. Oxalyl chloride (0.2 ml) was added followed by 0.03 ml of DMF. The reaction mixture was stirred at room temperature for 3 hours under argon and then evaporated to dryness in vacuo. The sapphyrin acid chloride so obtained was then redissolved in dry dichloromethane (20 ml) and added slowly under argon and at room temperature to a solution of 59.4 mg (0.15 mmol) of 1-(2-aminoethyl)-4-[(triphenylmethyl)-amino]-pyrimidin-2-one[19] containing 5 mg of 4-dimethylaminopyridine and 0.4 ml of dry pyridine in 20 ml of dry dichloromethane. After the addition was complete (ca. 1 hour), the reaction mixture was stirred overnight. The reaction mixture was then washed in succession with first dilute hydrochloric acid (3%, 20 ml), then water (20 ml) followed by saturated sodium bicarbonate (20 ml), and then finally water (20 ml) once again. The organic phase was then dried over sodium sulfate and the solvent removed in vacuo. The desired product 9 was isolated by column chromatography on silica gel using methanol, 2–5% in dichloromethane, as the eluent. The yield obtained this way was 91.0 mg (ca. 90%).

Method B. The sapphyrin acid 7a, described above (31.5 mg, 0.05 mmol), was dissolved in dry dichloromethane (20 ml). The resulting solution was then cooled to 0° C. and dicyclohexylcarbodiimide (41.27 mg, 0.2 mmol) and 1-hydroxybenzotriazole (5 mg) were added. The resulting solution was then stirred in an ice bath for 30 min. and the amino-functionalized cytosine, 1-(2-aminoethyl)-4-[(triphenylmethyl)amino]pyrimidin-2-one (29.7 mg, 0.075 mmol) was then added followed by 0.1 ml of dry pyridine. The reaction mixture was then stirred, first for 0.5 hours at 0° C. and then for 48 hours at room temperature. Acetic acid (0.2 ml) was then added and the solution stirred a further 1 hour at room temperature. Dicyclohexylurea was then filtered off and the reaction worked up as per method A. The yield of 9 obtained using this method was 42 mg (83.3%).

$^1$H NMR (300 MHz, CDCl$_3$): δ=−5.43 (2H, bs, NH), −4.67 (2H, bs, NH), 2.21 (12H, t, CH$_2$CH$_3$), 2.73 (2H, t, CONHCH$_2$CH$_2$), 3.11 (2H, t, CH$_2$CH$_2$CONH), 4.07 (9H, s, CH$_3$) 4.18 (3H, s, CH$_3$), 4.30 (3H, s, CH$_3$), 4.50 (4H, m, CH$_2$CH$_3$), 4.60 (4H, m, CH$_2$CH$_3$), 4.67 (2H, m, CONHCH$_2$C

H$_2$) 4.90 (2H, m, CH$_2$CH$_2$CONH), 6.20 (1H, d, C$^5$H), 6.80, (1H, bs, NH), 7.06–7.26 (15H, m, Tr), 7.54 (1H, s, CONH), 7.73 (1H, d, C$^6$H), 11.55 (2H, s, meso-H), 11.56 (2H, s, meso-H). FAB MS, m/e (rel. intensity): 1008 (25, [MH]$^+$), 1007 (58, M$^+$), 1006 (22, [M–H]$^+$), 765 (22, [M–Tr]$^+$). HRMS: Calcd. for C$_{65}$H$_{69}$N$_9$O$_2$ (M$^+$): 1007.5574. Found 1008.5654 ([MH]$^+$); for C$_{65}$H$_{70}$N$_9$O$_2$ ([MH]$^+$) calcd. 1008.5652.

EXAMPLE 7

SYNTHESIS OF SAPPHYRIN MONONUCLEOBASE STRUCTURES 3,8,17,22-Tetraethyl-12-[2-[1-(4-amino-2-oxopyrimidinyl)ethyl]-aminocarbonylethyl]-2,7,13,18,23-pentamethylsapphyrin, structure 10

Compound 9 (50.4 mg, 0.05 mmol) was dissolved in trifluoroacetic acid (5 ml) and the solution was heated at reflux for 1 hour. After allowing the solution to cool, the solvent was removed in vacuo. The residue was then redissolved in dichloromethane, filtered, and taken to dryness on a rotary evaporator. The crude product so obtained was purified by recrystallization from a dichloromethane-hexane (1:3, v.v.) mixture, or by column chromatography on silica gel using dichloromethane-methanol 9:1 v.v. as the eluent. Such purifications afforded compound 10 as its bis trifluoroacetic salt in ca. 75% yield (28.5 mg). Prior to use in transport studies, this trifluoroacetate salt was dissolved in dichloromethane and washed with either a 1M solution of NaOH in H$_2$O or with a saturated aqueous solution of sodium bicarbonate.

$^1$H NMR (300 MHz, CDCl$_3$): δ=–6.66 (1H, s, NH), –6.57 (1H, s, NH), –6.50 (1H, s, NH), –6.45 (1H, s, NH), –5.79 (1H, s, NH), 2.17 (12H, m, CH$_3$CH$_2$), 2.37 (2H, t, CONHCH$_2$CH$_2$), 3.08 (2H, t, CH$_2$CH$_2$CONH), 3.35 (2H, t, CONHCH$_2$CH$_2$), 4.11 (6H, s, CH$_3$), 4.20 (3H, s, CH$_3$), 4.23 (3H, s, CH$_3$), 4.25 (3H, s, CH$_3$), 4.54 (4H, q, CH$_2$CH$_3$), 4.68 (4H, q, CH$_2$CH$_3$), 5.12 (2H, t, CH$_2$CH$_2$CONH), 5.50 (1H, d, J=7.2, C$^5$H), 6.26 (2H, s, NH$_2$), 6.84 (1H, d, J=7.2, C$^6$H), 7.47 (1H, s, CONH), 11.52 (1H, s, meso-H), 11.65 (1H, s, meso-H), 11.69 (1H, s meso H), 11.70 (1H, s, meso-H). $^{13}$C NMR (125 MHz, CDCl$_3$): δ=12.52, 12.67, 12.86, 15.47, 15.83, 17.33, 17.51, 17.55, 17.57, 20.57, 20.68, 20.75, 22.55, 36.99, 37.74, 48.46, 91.50, 91.81, 91.87, 98.08, 98.22, 121.47, 126.37, 127.08, 127.82, 129.08, 129.92, 130.15, 130.20, 132.95, 132.98, 135.02, 135.25, 135.35, 135.61, 137.41, 138.51, 138.59, 140.49, 142.03, 142.10, 142.48, 147.08, 158.57, 173.65. FAB MS, m/e (rel. intensity): 768 (65, [MH$_2$]$^+$), 767 (78, [MH]$^+$), 766 (100, M$^+$), 766 (45, [M–H]$^+$). HRMS: Calcd. for C$_{46}$H$_{55}$N$_9$O$_2$ (M$^+$): 765.4478. Found 766.4535 ([MH]$^+$); for C$_{46}$H$_{56}$N$_9$O$_2$ ([MH]$^+$): calcd. 766.4556.

B. Preparation of 3,8,17,22-tetraethyl-12-{2-[7-(2-benzamide-6-oxopurinyl)ethyl]-aminocarbonylethyl}-2,7,13,18,23-pentamethylsapphyrin, structure 11

Sapphyrin monoacid 7a (63 mg, 0.1 mmol) was dissolved in dry tetrahydrofurane (30 ml) and cooled to 0° C., dicyclohexylcarbodiimide (103.2 mg, 0.5) was added with 10 mg of hydroxybenzotriazole and solution was kept at 0° C. for 30 minutes. 7-(2-Aminoethyl)-2-benzamidopurin-6-one was added with stirring. Reaction mixture was kept at 0° C. for 1 hour, then allowed to room temperature, and stirred for 48 hours. Acetic acid (0.1 ml) was added and stirred 1 hour, dicyclohexylurea was filtered off, solvent evaporated in vacuo. Redissolved in dichloromethane with 5% methanol, washed with diluted hydrochloric acid (10 ml, 3%), saturated solution of sodium hydrogencarbonate (10 ml) and with water (10 ml). Organic phase was dried over sodium sulfate and evaporated to dryness. Product 11 was purified by column chromatography on silica gel with 2–5% methanol. The yield was 81 mg (89.0%).

FAB MS, m/e (rel. intensity): 911 (96, [MH]$^+$), 910 (86, [M]$^+$).

HRMS: Calcd. for C$_{54}$H$_{60}$N$_{11}$O$_3$ 910.48739. Found 910.48806.

C. Preparation of 3,8,17,22-tetraethyl-12-{2-[7-(2-amino-6-oxopurinyl)ethyl]amino-carbonylethyl}-2,7,13,18,23-pentamethylsapphyrin, structure 12

This was prepared by splitting of benzoyl protecting group from derivative 11 described above using NH$_3$ in methanol at room temperature for 24 hours in 85% yield.

FAB MS, m/e (rel. intensity: 806 (96, [M]$^+$), 807 (68, [MH]$^+$).

HRMS: Calcd. for C$_{47}$H$_{56}$N$_{11}$O$_2$ 806.46131. Found 806.46185.

D. 3,12,13,22-Tetraethyl-8-(methoxycarbonylethyl)-17-{2-[7(2-benzamido-6-oxopurinyl)ethyl]aminocarbonylethyl}-2,7,18,23-tetramethylsapphyrin, structure 13

3,12,13,22-Tetraethyl-8-(carboxymethyl)-17-(methoxycarbonylethyl)-2,7,18,23-tetramethylsapphyrin 2c (23.5 mg, 0.033 mmol) was dissolved in dry dichloromethane (20 ml), solution was cooled by ice, dicyclohexylcarbodiimide (51.2 mg, 0.2 mmol) was added together with 5 mg of hydroxybenzotriazol, reaction mixture was kept at 0° C. for 30 minutes and then 7-(2-aminoethyl)-2-benzamidopurin-6-one (30 mg, 0.1 mmol) was added. The solution was kept cooled for 1 hour, then allowed to warm to room temperature and stirred for 30 hours. Acetic acid (0.1 ml) was added and stirred for 1 hour, dicyclohexylurea was filtered off, organic phase washed with water (10 ml), product was purified by crystallization from dichloromethane-hexane (1:1), final purification was made by column chromatography on silica gel with dichloromethane with 10% methanol and 0.3% of trifluoroacetic acid as a eluent. The yield of product 13 28 mg (79.5%).

$^1$H NMR spectrum (300 MHz, CDCl$_3$): δ=–5.50 (1H, s, NH), –5.31 (1H, s, NH), –5.04 (1H, s, NH), –4.97 (1H, s, NH), –4.95 (1H, s, NH), 2.05 (6H, t, CH$_2$CH$_3$), 2.20 (6H, t, CH$_2$CH$_3$), 2.91 (2H, t, CH$_2$CH$_2$NH), 3.46 (2H, t, CH$_2$CH$_2$N) 3.51 (3H, s, CO$_2$CH$_3$), 3.63 (2H, t, CH$_2$CH$_2$CO), 4.08 (6H, s, CH$_3$), 4.23 (6H, s, CH$_3$), 4.50 (2H, t, CH$_2$CH$_2$NH), 4.52 (4H, q, CH$_2$CH$_3$), 4.67 (4H, q, CH$_2$CH$_3$) 4.96 (2H, t, CH$_2$CH$_2$CONH) 7.40 (2H, m, BzH), 7.58 (1H, m, BzH), 7.65 (2H, m, BzH) 7.98 (1H, br s, C$^8$H), 8.01 (1H, s, CONH), 11.62 (2H, s, meso-H), 11.63 (2H, s, meso-H).

$^{13}$C NMR (125 MHz, CDCl$_3$ with 20% CD$_3$OD): δ=12.68, 12.82, 16.52, 16.61, 17.76, 17.86, 18.47, 18.57, 20.56, 20.61, 20.65, 20.76, 22.76, 23.50, 29.58, 36.97, 51.98, 91.71, 96.25, 126.88, 127.41, 127.46, 128.27, 129.44, 129.59, 129.85, 129.96, 132.23, 133.96, 134.45, 138.12, 139.23, 143.45, 144.79, 145.10, 173.23, 173.35, 173.45. FAB MS m/e (rel. intensity): 982 (95, [M–H]$^+$), 983 (87, [M]$^+$).

HRMS: Calcd. for C$_{57}$H$_{64}$N$_{11}$O$_5$ 982.51087. Found 982.50919.

E. Preparation 3,12,13,22-Tetraethyl-8-(methoxycarbonylethyl)-17-{2-[17-(2-amino-6-oxopurinyl)ethyl]-aminocarbonylethyl}-2,7,18,23-tetramethylsapphyrin, structure 14

This compound was prepared in 88% yield from the benzoyl derivative 13 previously described using a saturated solution of NH$_3$ in methanol at room temperature for 30 hours.

FAB MS, m/e (re. intensity): 879 (98, [M]⁺), 880 (68, [MH]⁺).

HRMS: Calcd. for $C_{50}H_{61}N_{11}O_4$ 879.49291. Found 879.080.

F. Preparation of 3,12,13,22-Tetraethyl-8-(carboxymethyl)-17-{2-[7-(2-amino-6-oxopurinyl)ethyl]aminocarbonylethyl}-2,7,18,23-tetramethylsapphyrin, structure 15

This compound was prepared in 75% yield from the benzoyl derivative 13 by hydrolysis with KOH solution in methanol at room temperature for 48 hours. This is a very convenient building block for construction of sapphyrin conjugates with different nucleobases.

FAB MS, m/e (re. intensity): 866 (68, [M]⁺), 867 (56, [MH]⁺, 865 (54, [M–H]⁺).

HRMS: Calcd. for $C_{49}H_{59}N_{11}O_4$ 865.47511. Found 865.47451.

EXAMPLE 8

SYNTHESIS OF SAPPHYRIN DINUCLEOBASE STRUCTURES

A. Preparation of 3,12,13,22-Tetraethyl-8-{2-[1-[2-oxo-4-[triphenylmethyl)amino]pyrimidyl]ethyl]aminocarbonylethyl}-17-{2-[7-(2-amino-6-oxopurinyl)ethyl]-aminocarbonylethyl}-2,7,18,23-tetramethylsapphyrin, structure 16

This compound was prepared in 69% yield from sapphyrin 15 as described above by condensation (carbodiimide method) with 1-(2-aminoethyl-4-[(triphenylmethyl)amino]-pyrimidin-2-one.

FAB MS, m/e (rel. intensity): 1244 (78, [M]⁺), 1245 (65, [MH]⁺).

HRMS: Calcd. for $C_{74}H_{81}N_{15}O_4$ 1243.659547. Found 1243.65940.

B. Preparation of 3,12,13,22-Tetraethyl-8,17-bis{2-[7-(2-benzamido-6-oxopurinyl)ethyl]-aminocarbonylethyl}-2,7,18,23-tetramethylsapphyrin, structure 17

Sapphyrin bis acid 2a (34.5 mg, 0.05 mmol) was converted to its corresponding bis acid chloride as previously described herein. A solution of this acid chloride in dry dichloromethane (20 ml) was then slowly added to a solution of 7-(2-aminoethyl)-2-benzamidopurin-6-one (60 mg, 0.2 mmol), which contained 0.3 ml of dry pyridine and 10 mg of 4-dimethylaminopyridine. The reaction mixture was stirred at room temperature for 36 hours. Dichloromethane-methanol (5:1) 20 ml was added and the resulting solution then washed first with diluted hydrochloric acid (10 ml, 3%), then with saturated solution of sodium hydrogencarbonate (10 ml) and then finally with water (10 ml). The organic phase was dried over sodium sulfate and evaporated to dryness. The product 17 was crystallized from methanol-dichloromethane (1:15). The yield was 55 mg (88.0%).

¹³C NMR spectrum (125 MHz, CDCl₃ with 25% CD₃OD): δ=13.90, 15.63, 17.63, 18.41, 20.72, 20.83, 22.20, 22.81, 23.26, 33.99, 46.32, 46.36, 63.07, 92.00, 98.80, 111.59, 1111.59, 123.02, 127.16, 127.73, 127.89, 128.34, 128.65, 128.95, 129.97, 131.09, 133.21, 133.41, 138.57, 138.91, 142.66, 144.00, 148.28, 151.44, 168.59, 168.89, 172.91, 173.30.

FAB MS, m/e (rel. intensity): 1249 (88, [M]⁺), 1250 (56, [MH]⁺), 1251 (45, [M+2H]⁺).

HRMS: Calcd. for $C_{70}H_{77}N_{17}O_6$ 1251.62667. Found 1251.62427. [MH₂]⁺.

C. Preparation of 3,12,13,22-tetraethyl-8,17-bis{2-[7-(2-amino-6-oxopurinyl)ethyl]-amino-carbonylethyl}-2,7,18,23-tetramethylsapphyrin, structure 18

This compound was prepared in 78% yield from the above-described bis benzoyl derivative 17 by stirring with $NH_3$ in methanol at room temperature for 30 hours.

FAM MS, m/e (rel. intensity): 1041 (95, [M]⁺), 1040 (78, [M–H]⁺), 1042 (56, [MH]⁺).

HRMS: Calcd. for $C_{56}H_{76}N_{17}O_4$ 1041.55787. Found 1041.55619.

D. 3,12,13,22-tetraethyl-8,17-bis[2-[1-[2-oxo-4-[(triphenylmethyl)amino]pyrimidyl]-ethyl]aminocarbonylethyl]-2,7,13,18,23-tetramethylsapphyrin, structure 19

3,12,13,22-Tetraethyl-8,17-bis(methoxycarbonylethyl)-2,7,18,23-tetramethyl-sapphyrin 2b and 3,12,13,22-tetraethyl-8,17-bis(carboxyethyl)-2,7,18,23-tetramethylsapphyrin 2a were prepared as described by Sessler et al. (1990; reference 4a), incorporated herein by reference. This latter diacid 2a (34.5 mg, 0.05 mmol) was then suspended in dry dichloromethane (20 ml), and, under argon, treated with oxalyl chloride (0.3 ml) and DMF (0.03 ml). The reaction mixture was stirred at room temperature for 3 hours and then taken to dryness in vacuo. The resulting sapphyrin bis acid chloride was redissolved in dry dichloromethane (15 ml) and added slowly to a solution of 1-(2-aminoethyl-4-[(triphenylmethyl)amino]-pyrimidin-2-one (51.48 mg, 0.13 mmol) in dry dichloromethane (20 ml) containing 4-dimethylaminopyridine (5 mg) and dry pyridine (0.3 ml). The reaction mixture was stirred under argon at room temperature for 12 additional hours, then washed with first dilute hydrochloric acid (3%, 30 ml), then water followed by saturated aqueous sodium bicarbonate, and then, finally, with water once again. After drying over anhydrous sodium sulfate, the product was isolated by column chromatography on silica gel using dichloromethane-methanol (1→10%, gradient) as the eluent. The yield of compound 19 obtained in this manner was 65.0 mg (89.9%).

¹H NMR (300 MHz, CDCl₃): δ=–5.25 (2H, s, NH), –5.05 (2H, s, NH), 2.13 (12H, t, C$\underline{H}_3$CH₂), 2.93 (4H, m, CONHC$\underline{H}_2$CH₂), 3.23 (4H, m, CH₂C$\underline{H}_2$CONH), 3.83 (4H, t, CONHCH₂C$\underline{H}_2$), 4.00 (6H, s, CH₃), 4.15 (3H, s, CH₃), 4.25 (3H, s, CH₃), 4.57 (4H, q, C$\underline{H}_2$CH₃), 4.75 (4H, q, C$\underline{H}_2$CH₃), 4.99 (4H, m, C$\underline{H}_2$CH₂CONH), 5.50 (2H, d, C⁵H), 6.73 (2H, s, NH), 7.01–7.29 (30H, m, Tr), 7.28 (2H, d, C⁶H), 7.67 (2H, s, CONH), 11.43 (4H, bs, meso-H). FAB MS m/e (rel intensity): 1446 (58, M⁺), 1447 (38, [MH]⁺). HRMS Calcd for $C_{92}H_{95}N_{13}O_4$: 1445.7645. Found 1445.7658.

E. 3,12,13,22-Tetraethyl-8,17-bis(2-[1-(4-amino-2-oxopyrimidinyl)-ethyl]-aminocarbonylethyl]-2,7,13,18,23-pentamethylsapphyrin, structure 20

The bis(trityl) sapphyrin-cytosine derivative 19 (72.3 mg, 0.05 mmol) was dissolved in trifluoroacetic acid (5 ml) and heated to reflux for 0.5 hour. After cooling, the trifluoroacetic acid was removed by evaporation and the product purified (as its trifluoroacetate salt) by column chromatography on silica gel using methanol (15% by volume) in dichloromethane as the eluent. Alternatively, this salt could be purified by recrystallization from dichloromethane-hexane-methanol (1:1:0.1 v.v.v.) to give 38.0 mg (79.0%) of deprotected product 20, $(CF^3CO_2H)_2$. Prior to use in transport studies, this trifluoroacetate salt was dissolved in dichloromethane and washed with either a 1M solution of NaOH in H₂O or with a saturated aqueous solution of sodium bicarbonate.

¹H NMR (300 MHz, CDCl₃): δ=–5.91 (1H, s, NH), –5.70 (2H, s, NH), –5.47 (2H, s, NH), 2.08 (6H, m, C$\underline{H}_3$CH₂), 2.13 (6H, m, C$\underline{H}_3$CH₂), 2.71 (4H, t, CONHC$\underline{H}_2$CH₂), 3.08 (4H, t, CH₂C$\underline{H}_2$CONH), 3.50 (4H, t, CONHCH₂C$\underline{H}_2$), 4.07 (3H, s, CH₃), 4.13 (3H, s, CH₃), 4.20 (3H, s, CH₃), 4.23 (3H, s, CH₃), 4.51 (4H, q, C$\underline{H}_2$CH₃), 4.68 (4H, q, C$\underline{H}_2$CH₃), 5.29 (4H, m, C$\underline{H}_2$CH₂CONH), 5.69 (2H, d, J=7.20, C⁵H), 6.35 (4H, bs, NH₂), 6.89 (2H, d, J=7.20, C⁶H), 7.50 (2H, s, CONH) 11.52 (1H, s, meso-H), 11.57 (1H, s, meso-H), 11.61 (1H, s, meso-H), 11.63 (1H, s, meso-H). $^{13}$C NMR (125 2 MHz, CDCl$_3$ with 10% CD$_3$OD): δ=12.88, 12.90, 12.98, 16.03, 17.55, 17.63, 17.70, 18.23, 18.29, 18.37, 18.43, 20.23, 20.55, 20.75, 20.89, 20.91, 20.96, 22.58, 29.59, 35.58, 37.69, 37.84, 37.91, 48.80, 48.98, 49.15, 49.32, 49.48, 49.66, 49.83, 97.79, 97.91, 97.94, 97.97, 122.99, 128.27, 129.62, 129.74, 129.84, 129.86, 129.91, 129.95, 130.06, 130.10, 130.15, 130.24, 130.32, 135.38, 135.43, 138.93, 139.53, 143.23, 144.23, 144.59, 172.66. FAB MS m/e (rel intensity): 962 (45, M$^+$), 963 (38, [MH]$^+$). HRMS: Calcd for C$_{54}$H$_{67}$N$_{13}$O$_4$: 961.5439. Found 961.5448.

EXAMPLE 9

PREPARATION OF OLIGOMERIC SAPPHYRINS

A. Preparation of sapphyrin dimers

Sapphyrin monoacid 7a (126 mg, 0.2 mmol) was converted to acid chloride as previously described hereinabove. A solution of acid chloride in dry dichloromethane (20 ml) was slowly added to the solution of 0.1 mmol aromatic bis(amino) compound in dry dichloromethane (20 ml), which contained 5 mg 4-dimethylaminopyridine and 0.3 ml of dry pyridine. The reaction mixture was stirred 48 hours at room temperature, then washed with water, organic phase was dried with magnesium sulfate and evaporated. The product was isolated by column chromatography on silica gel in dichloromethane with 2–10% of methanol as a eluent. Reaction with 1,8-diaminonapthalene (0.1 mmol, 15.8 mg) gave 80 mg (57.89%) of product 21.

FAB MS m/e (rel. intensity) 1382 (67, [MH]$^+$), 1381 (56, [M]$^+$).

HRMS Calcd. for C$_{90}$H$_{100}$N$_{12}$O$_2$ : 1380.80916. Found 1380.8093.

Reaction with m-phenylenediamine (0.1 mmol, 10.8 mg) gave 69 mg (51.80%) of product 22.

FAB MS m/e (rel. intensity) 1333 (78, [MH]$^+$), 1332 (65, [M]$^+$).

HRMS Calcd. for C$_{86}$H$_{98}$N$_{12}$O$_2$ : 1330.79352. Found 1330.79349.

Reaction with aliphatic diamino compounds was carried with DCC as a coupling reagent. Sapphyrin acid 7a (126 mg, 0.2 mmol) was dissolved in dry dichloromethane under argon and cooled by ice. Dicyclohexylcarbodiimide (0.5 g) was added with 5 mg of hydroxybenzotriazole. The reaction mixture was stirred at 0° C. for 30 minutes and then 1,3-diaminopropane (7.4 mg, 0.1 mmol) was added. The reaction mixture was stirred 30 minutes at 0° C. and 48 hours at room temperature. Acetic acid (0.2 ml) was added, stirred 1 hour, dicyclohexylurea was filtered off, and the product was isolated by column chromatography on silica gel with dichloromethane contains 5–10% of methanol. The yield of compound 23 was 96 mg (73.97%).

B. Preparation of sapphyrin trimers

The inventors used the same coupling procedures as described above for the sapphyrin dimers. Thus sapphyrin monoacid 7a (189 mg, 0.3 mmol) was coupled (DCC method, 0.75 g) with tris(2-aminoethyl)amine (14.6 mg, 0.1 mmol) giving 160 mg (80.73%) of compound 24.

FAB MS m/e (rel. intensity) 1983 (36, [MH]$^+$), 1982 (32, [M]$^+$).

HRMS Calcd. for C$_{126}$H$_{153}$N$_{19}$O$_3$ : 1980.240296. Found 1980.240289.

EXAMPLE 10

PREPARATION OF SAPPHYRIN POLYMERS (CLASS I)

This class of sapphyrin polymers may be termed Class I of the broad group of sapphyrin polymers, or may be referred to as group IV of these wide-ranging sapphyrin inventions. For the preparation of this class of polymers, sapphyrins with ethylene units could be used, as prepared by the elimination of acetoxy derivative, as well as sapphyrin bis acid, sapphyrin diamino and dihydroxyderivatives. Sapphyrins bearing covalently attached nucleobases could also be used for the polymerization reactions.

Radical polymerization may be catalyzed by dibenzoylperoxide, or bisazaisobutyronitril in inert solvent at temperature 120°–200° C.

Polycondensation reaction 3,12,13,22-Tetraethyl-8,17-bis(carboxyethyl)-2,7,18,23-tetramethylsapphyrin 2a (1 mmol) and 1,1'-carbonyldiimidazole (1.1 mmol) were mixed in diphenylether for 1 hour, then 3,12,13,22-tetraethyl-8,17-diaminoethyl-2,7,18,23-tetramethylsapphyrin 25 (1 mmol) was added and reaction heated at 190°–250° C. for 2 hours. After cooling dichloromethane was added, polymeric sapphyrin structure 26A (where X=NH) was filtered off, washed with water (50 ml) and methanol (50 ml).

Polymeric sapphyrin was obtained also with using sulfolan, hexamethylphosphortriamide as a solvent. The reaction could be also carried out without solvent.

The same procedure was used for the sapphyrin dialcohol as a starting compound for the reaction with sapphyrin diacid structure 26B (where X=O).

To synthesize structure 27, it is contemplated that one would employ standard phosphoramidate chemistry, as will be known to those of skill in the art in light of the present disclosure.

EXAMPLE 11

SYNTHESIS OF POLYMER SUPPORTED SAPPHYRINS (CLASS II)

This class of sapphyrin polymers may be termed Class II of the broad sapphyrin polymer group, and is also referred to as group V of the overall sapphyrin invention.

The new chromatographic bonded phases that are the subject of these aspects of the present invention were prepared in two steps. In the first, a phosphate thioether recognition unit was connected (via amide, ether, thioether, or NH bonds) with silica gel. This was followed, as a second step, by protection of residual silanol groups on the silica gel surface using variety of silylating reagents (from C$_1$ to C$_{18}$). The density of coverage for the covalently bonded recognition groups on the silica gel was controlled by the amount of expanded porphyrin, or guanidinium derivatives (in mmol) that was attached to 1 g of the starting silica gel. Elemental analysis data, namely comparison of the % C and % N in the starting material and the product, provided a measure of the ratio of phosphate receptor (in µM) to 1 g of silica gel. Solid state $^{31}$P NMR spectra also provided a unique tool for the detailed study of the mechanism of phosphate binding.

A. 3,8,17,22-Tetraethyl-12-(propylamidoethyl)-2,7,13,18,23-pentamethylsapphyrin-silica gel, structure 34 where Z=CH$_3$ 3,8,17,22-Tetraethyl-12-carboxyethyl)-2,7,13,18,23-pentamethylsapphyrin (0.63 g, 1 mmol) was dissolved under nitrogen in 100 ml of dry dichloromethane and 1 ml of oxalylchloride was added, followed by 0.05 ml of dry N,N-dimethylformamide. The reaction mixture was then stirred at room temperature for 2 hours, and subsequently evaporated to dryness. Sapphyrin acid chloride was redissolved in dry dichloromethane (50 ml) and slowly (2 hours, dropping funnel) added to suspension of 5 g of 3-aminopropyl functionalized silica-gel (from Aldrich, 9% functionalized, dried for 24 hours at high vacuum) in 100 ml of dichloromethane, which contained 1 ml of dry pyridine and 10 mg of 4-dimethylaminopyridine. After addition was complete, the reaction mixture was stirred for two days. The product was then filtered off, washed with dichloromethane (300 ml), dichloromethane-methanol (5:1; 200 ml), methanol (200 ml), water (300 ml), methanol (300 ml), dichloromethane (300 ml) and hexane (300 ml). The produce was then dried at high vacuum giving 5.35 g of the sapphyrin bonded silica gel. Elemental analysis: starting 3-aminopropyl-functionalized silica gel: 4.85% C, 1.48% H, 1.62% N. Product: 6.28% C, 1.73% H, 1.99% N.

IR: Solid state $^{13}$C NMR: Shift 3.5 ppm (up field) was observed for AMP (standard AMP on aminopropylsilica gel).

As a coupling reagent, 1,1'-carbonyldiimidazol, active ester (generated by reaction 1,1'-carbonyldiimidazol and 1-hydroxybenzotriazole), carbodiimide derivatives e.g. 1-(3-dimethylaminopropyl)-3-ethyl-carbodiimide were also used.

B. 3,8,17,22-Tetraethyl-12-(amidoethyl)-2,7,13,18,23-pentamethyl-silica gel, structure 34 where Z=CH$_3$ Sapphyrin acid (63 mg, 0.1 mmol) was dissolved in dry tetrahydrofuran (100 ml) and cooled to 0° C. Then 0.2 g of 1-(3-dimethylaminopropyl)-3-ethyl-carbodiimide was added along with 10 mg of 1-hydroxybenzotriazol. The reaction mixture was then stirred at 0° C. for 45 minutes. After this 3 g of dried 3-aminopropyl-functionalized silica gel was added and the resulting mixture kept at 0° C. for 1 hour and 24 hours at room temperature. After that, another 0.1 g of carbodiimide was added and the whole stirred for another 2 days. The product was then filtered off and washed as described above. The yield of sapphyrin-bonded silica gel is 3.05 g.

C. 3,8,17,22-Tetraethyl-12-(amidoethyl)-2,7,13,18,23-pentamethyl-silica gel, structure 34 where Z=CH$_3$ This represents another synthetic method for preparing the silica gel version of structure 34 where Z=CH$_3$. This would be conducted as described in previous, except that 0.25 g of 1,1'-carbonyldiimidazol would be used as the coupling agent at room temperature.

D. Preparation of partially sapphyrin-functionalized 3-aminopropyl silica gel, structure 35

This sorbent was prepared for the second and third generation of columns, with the intention to leave a certain number of amino groups free (unbound to sapphyrin) for the binding of another type of recognition unit—second generation—hydrogen-bond recognition unit for nucleobases; the third generation—aromatic residue for introduction π—π stacking interaction with pyrimidine or purine ring of nucleotides.

1 g of 3-Aminopropyl silica gel (from Sigma, 1.0 mmol N per gram) was suspended in dry dichloromethane (25 ml) with 0.5 ml of dry pyridine. 3,8,17,22-tetraethyl-12-(carboxyethyl)-2,7,13,18,23-pentamethylsapphyrin (0.567 g, 0.9 mmol) was converted to acid chloride as described before and slowly added to the 3-aminopropyl silica gel. The reaction mixture was stirred at room temperature for 3 days, then product was filtered off, washed with dichloromethane (30 ml), methanol (50 ml), water (100 ml), methanol (50 ml) and dichloromethane (50 ml). The product was dried (giving 1.49 g; 95% yield) and used for further derivatization—10% of amino groups were left unbound for coupling with hydrogen-bond recognition unit, or aryl substituent for π—π stacking interaction.

EXAMPLE 12

SILYLATION PROCEDURE

For the separation of highly polar phosphorylated species on both analytical and preparative scale, the surface of silica gel must be modified by a silylation procedure. This procedure basically converts most, if not all, the free silanol groups (—Si—OH) to —Si—O—Z type residues, where Z is an alkyl chain, or aryl substitution (ArCO$_2$—, ArCO—). Silylation reagents which have been employed are those of type Z$_2$SiCl$_2$, ZSiCl$_3$, and Z(CH$_3$)$_2$SiCl, where Z is an alkyl residue with 1 to 18 carbon atoms in it or an aryl (phenyl, pentefluorophenyl) substituent.

For the silylation of the bonded silica gels in this invention we have used the following procedure: Introduction of the C$_1$, C$_8$, C$_{12}$, and C$_{18}$ groups by reaction of mono and trichlorosilanes with suspended bonded silica gel in an organic solvent (dry dichloromethane, dichloroethane, benzene, toluene, xylene, or pyridine and 2,6-lutidine was used directly as a solvent) either directly or in the presence of organic bases such as pyridine or 2,6-lutidine, in a temperature range of 25° C.–150° C. for the preparative HPLC phases, the corresponding triflates were used for silylation.[38]

A. Dimethylsilyl functionalized sapphyrin silica gel, structure 34 where Z=CH$_3$ The bonded sapphyrin-silica gel prepared as described above in Example 11, section A, (1 g) was suspended in 50 ml of dry dichloromethane, 1 ml of trimethylchlorosilane was then added, followed by 0.5 ml of dry pyridine. The suspension was then stirred for 2 hours at room temperature. The product was then filtered off, washed with dichloromethane (200 ml), methanol (100 ml), methanol-water 1:1 (200 ml), methanol (100 ml), dichloromethane (100 ml) and hexane (200 ml) and dried in vacuo. The yield was 1.1 g of product.

Elemental analysis: 8.55% C, 1.92% H, 1.82% N.

EXAMPLE 13

SYNTHESIS OF SAPPHYRIN SUBSTITUTED MERRIFIELD RESIN

A sapphyrin substituted Merrifield resin was prepared using the same basic strategy as described above. This is intended for use in low pressure applications.

A. 3,8,17,22-Tetraethyl-12-(aminocarbonyl)-2,7,13,18,23-pentamethylsapphyrin structure derivative, structure 31.

(0.63 g, 1 mmol) of 7a was converted to acid chloride as described hereinabove, oxalylchloride with DMF catalyst. A solution of this sapphyrin acid chloride in dry dichloromethane was then slowly added to a suspension of the benzhydrylamine hydrochloride polymer bound (BHA resin, α-aminodiphenylmethane hydrochloride polymer bound; polystyrene crosslinked with 2% divinylbenzene, α-aminobenzylated hydrochloride—0.7 mmol amine/g resin; 100–200 mesh), 1 g in 100 ml of dry dichloromethane, with 2 ml of dry pyridine. The reaction mixture was stirred at room temperature for 3 days. The polymeric material was filtered off, washed 5 times with dichloromethane (5×30 ml), 5 times with water (5×20 ml), 5 times with methanol (5×20 ml) and with dichloromethane (20 ml). The polymeric products were deep green in color as a result of the covalently attached sapphyrins, elemental analysis (a most important determination of bonded sapphyrin is an increase in nitrogen content as compared to the starting polymeric material) showed, that 85% of amino groups are attached to sapphyrin, structure 31.

B. Preparation of 3,8,17,22-Tetraethyl-12-1aminocarbonyl) -2,7,13,18,23-pentamethyl sapphyrin derivative, Structure 32

The sapphyrin acid 7a (63 mg, 0.1 mmol), described hereinabove, was converted to its corresponding acid chloride. A solution of this acid chloride in dry dichloromethane was then added, under argon, to a suspension of aminomethyl-polystyrene (benzylamine polymer bound; copolymer of styrene and divinylbenzene, aminomethylated; 1.1 mmol amine/g resin) 500 mg in 50 ml of dry dichloromethane, with 0.5 ml of dry pyridine. The reaction mixture was stirred at room temperature for 7 days, and the resin was filtered off and washed as previously described. Elemental analysis was used to determine the quantity (loading level) of the attached sapphyrin. It was found that ca. 15% of the amino groups of the polymeric support were attached to sapphyrin, 32.

The same reaction starting with 200 mg of the above-specified aminomethyl-polystyrene gave 42% saturation in terms of amino groups bound to sapphyrin.

C. Preparation of 3,12,13,22-tetraethyl-8,17-bis(aminocarbonyl)-2,7,18,23-tetramethyl sapphyrin derivative, Structure 33

The same type of procedure was used for sapphyrin bis acid. For the connection of the sapphyrin mono acid with covalently bonded nucleobase, the amino functionalized polymer used as the solid support and either 1,1'-carbonyldiimidazole or 1-(3-dimethylaminopropyl)-3-ethylcarbodiimide were used as the acid activating agents as appropriate.

Sapphyrin bis amino derivative 25 (0.1 mmol) was dissolved in dry dimethylformamide and added to chloromethylated styrene-divinylbenzene resin (0.8 mmol Cl/g resin), 250 mg, together with 500 mg potassium carbonate. The reaction mixture was stirred and heated at 110° C. for 24 hours. After cooling to room temperature a solid material was filtered off, washed with water (250 ml), methanol (100 ml), and dichloromethane (100 ml). After drying, elemental analysis showed (as determined by a decrease in Cl content and an increase in N content) that 21% of the chloromethyl groups were transformed to sapphyrin-aminomethyl groups.

EXAMPLE 14

COLUMN PACKING AND SEPARATION OF PHOSPHORYLATED SPECIES

Columns using the new bonded sapphyrin materials are stable in aqueous buffers from pH 2.5 to pH 9.0 and stable to normal organic solvents. Furthermore, the packings are mechanically rigid due to their silica gel backbone. Indeed, the chemical and mechanical stability of such new columns makes them suitable for use over long periods of time without loss of resolution. Moreover, columns made from the presently described supports do not compress at high pressure and flow rates. The use of surface modified spherical silica gels results in products for use in medium to high pressure applications. For low pressure applications, organic polymer based sapphyrins, for example, modified Merrifield resins, may be used.

The effectiveness of separation using these new stationary phases is far superior to those currently used. Also, the lifetimes of the columns are long because only very mild elution conditions are required: low concentration of buffer at neutral pH. Usually isocratic (i.e., non gradient) conditions are sufficient for the separation even for very complicated mixtures. This makes the analysis of a series very fast and there is no need for column equilibrium after each analysis. These advantageous features allow for the rapid and efficient separation of different phosphorylated species, such as nucleotides, mono-, di- and triphosphates, oligonucleotides, DNA and RNA fragments, phosphosugars, phosphoproteins and organophosphorus compounds, using the sapphyrin-based solid supports of this invention.

In one example, a column containing first generation C34 sapphyrin-substituted silica gel was prepared using a standard column packing procedure, as described in the literature (see, e.g., reference 23b, pp 207–210). In this context, the columns are slurry-packed in methanol or acetone, followed by a wash with water and an HPLC pump which generates a solvent flow if 10 ml/min at 300–400 bar is used.

A. Separation of mono-, di-, and tri-phosphorylated nucleotides

Using the first generation of the sapphyrin-substituted silica gel, structure 34, the inventors were able to successfully separate adenosine and its mono-, di-, and tri-phosphorylated nucleotide forms.

The results of the HPLC separation of adenosine, mono-, di-, and tri-phosphates using the first sapphyrin-modified silica gel are shown in FIGS. 7A-i and 7A-ii. Commercially obtained adenosine, AMP, ADP, and ATP were prepared by dissolving in 5 mM tris (hydroxymethyl) aminomethane buffer at pH 7.0. 20 μl of an adenosine, AMP, ADP, and ATP mixture was loaded onto and eluted off the sapphyrin-modified silica gel using an isochratic buffer of 100 mM dibasic ammonium phosphate buffer at a pH of 7.0 and a flow rate of 0.2 ml/min. The wavelength of 260 nm was monitored and results were confirmed with retention times and UV-visible spectrum obtained from samples of individual compounds.

The insert in FIG. 7A-i shows the same mixture run through a control column with no sapphyrin. It is clear that there is a striking difference between the sharp peaks using the new sapphyrin-based technology and the unresolved broad band obtained with a more conventional column.

The HPLC separation of adenosine, mono-, di-, and tri-phosphates using the first sapphyrin-modified silica gel, structure 34 is also shown in FIG. 7B. In this case, the applied mixture was eluted off the sapphyrin-modified silica gel using an isochratic buffer of 500 mM dibasic ammonium phosphate buffer at a pH of 7.0 and a flow rate of 1.0 ml/min. Clear separation is still achieved. The wavelength of 260 nm was monitored and results were confirmed with retention times and UV-visible spectrum obtained from samples of individual compounds.

B. Separation of 2-, 3-, 4-, 5-, 6-, 7-, 8-, and 9-mers oligonucleotides

Using the first generation sapphyrin of substituted silica gels, structure 34, the inventors were able to successfully separate 2-, 3-, 4-, 5-, 6-, 7-, 8- and 9-mer oligonucleotides.

Results of the HPLC separation of commercially obtained adenosine-derived oligonucleotides using the first sapphyrin-modified silica gel are shown in FIGS. 8A-i and 8A-ii. Samples of 2-, 3-, 4- and 5-mers of polydeoxyadenylic acid were prepared by dissolving in 5 mM of tris (hydroxymethyl) aminomethane at pH 7.0. 20 μl of this mixture was loaded onto and eluted off the column using an isochratic buffer of 100 mM dibasic ammonium phosphate at pH 7.0 and a flow of 0.35 ml/min. The wavelength of 260 nm was monitored and results were confirmed with retention times and UV-visible spectrum obtained from samples of individual compounds.

The results obtained with this new sapphyrin-based methodology are very impressive. Note the marked difference between the sharp, distinct peaks shown in this figure with the broad, unresolved peak of the insert which represents the same mixture run through a control column with no sapphyrin. Furthermore, in addition to separating out the oligonucleotides in this supposedly pure mixture, higher and lower order impurities were also observed.

Results of the HPLC separation of longer commercially obtained adenosine-derived oligonucleotides using the first sapphyrin-modified silica gel, structure 34 are shown in FIG. 8B. A sample of a mixture of 2-, 3-, 4-, 5-, 6-, 7-, 8- and 9-mers of polydeoxyadenylic acid was loaded onto and eluted off the column using 100 mM dibasic ammonium phosphate at pH 7.0 and a flow of 0.35 ml/min. The wavelength of 260 nm was monitored and results were confirmed with retention times and UV-visible spectrum obtained from samples of individual compounds.

These results are also striking, and effective separation of all species was achieved. Clearly, all of these results are remarkable, particularly as various impurities not known to be present in the commercially available mixture were identified, the presence of which was later confirmed at source (Sigma Chemical Co.).

EXAMPLE 15

SECOND GENERATION SAPPHYRIN SOLID SUPPORTS

The preparation of improved, second generation sapphyrin solid supports may be achieved in many ways. For example, in one stage of the synthetic development, long chain alkyls may be introduced onto the surface of the sapphyrin-substituted silica-gel. This will result in second-generation columns that will combine the properties of both reverse phase separation and sapphyrin-based phosphate chelation and ion exchange.

A. Octadecylsilyl functionalized supply in silica gel, structure 34 where Z=octyl group $C_8H_{17}$ The bonded silica gel prepared as described above in Example 11, sections A and B, (1 g) was suspended in dry toluene (50 ml). octadecyltrichlorosilane was then added (0.5 ml) followed by dry pyridine (0.3 ml). The resulting reaction mixture was then heated at 100° C. for 6 hours and cooled. The product was then filtered off and washed as described above in Example 11, sections A and B. The yield was 1.095 g of product.

B. Dimethyloctadecylsolyl functionalized sapphyrin silica gel, structure 34 where Z=octadecyl group $C_{18}H_{37}$ The bonded silica gel prepared as described above in Example 11, sections A and B, (1 g) was suspended in 50 ml of dry 1,2-dichloroethane. 0.5 gram of chlorodimethyloctadecylsilane was then added followed by 0.3 ml of 2,6-lutidine. The resulting reaction mixture was subsequently heated to reflux for 8 hours. It was then cooled and the product filtered off, washed and dried. The yield was 1.086 g of product.

C. Dimethyldodecylmethyl functionalized supply in silica gel, structure 34 where Z=$C_{12}H_{35}$ The same procedure as described above in Example 15, section A was also carried out using chlorodimethyldodecylsilane as silylation agent.

D. Dimethyloctylsilyl functionalized sapphyrin silica gel, structure 34 where Z=$C_8H_{17}$ The same procedure as described above in Example 15, section B, was also carried out using chlochlorodimethyloctysilane as silylation agent.

E. Octyl functionalized supply in silica gel, structure 36 where Z=$C_8H_{17}$ and R=ClOH The same procedure as described above in Example 15, section A, was also carried out using octyltrichlorosilane as a silylation agent. followed by hydrolysis in water (10 μl, 2 hours, 40° C.).

F. Dodicyl functionalized supply in silica gel, structure 36 where Z=$C_{12}H_{25}$ and R=Cl The same procedure as described above in Example 15, section B, was also carried out using dodecyltrichlorosilane as a silylation agent.

G. Dimethyloctadeyl functionalized supply in silica gel, structure 36 where Z=$C_{18}H_{37}$ and R=Cl The same procedure as described above in Example 15, section B, was also carried out using dimethyloctadecylsilytriflate as a silylation agent.

EXAMPLE 16

THIRD GENERATION SAPPHYRIN SOLID SUPPORTS

Even further improved, third generation, sapphyrin solid supports may also be prepared. For example, third-generation systems may be prepared in which various different substituents on both the expanded porphyrin molecules and on the stationary phase material itself (e.g., Z and $R^8$ groups) are chosen to impart the desired groups and properties to the resultant material.

In one case, nucleobase-bearing systems may be generated which are expected to be able to separate nucleotides and oligonucleotides not only on the basis of charge and length but also on the basis of nucleic acid type. Introduction of aryl substituents give the possibility for improved separation based on phosphate cheletion and $\pi$—$\pi$ stacking. Any substituent for multiple type separation introduced by acylation, akylmethylation on free amino groups and/or by silylation with pheyl (substituted phenyl), silyl reagents or arylmethylation of OH groups.

A. 3,12,13,22-Tetraethyl-8-(aminoethyl)-17-{2-[1-(4-amino-2-oxo pyrimidinyl)-ethyl]-aminocarbonylethyl}-2,7,13,18,23-pentamethyl-silica gel Nucleobase substituted sapphyrins were attached to silica gel in accordance with general procedure as described above in Example 11, section A. More particularly, 3,12,13,22-tetraethyl-8-(carboxyethyl)-17-{2-[1-(4-amino-2 oxopyrimidinyl)-ethyl]aminocarbonylethyl}-2,7,13,18,23-pentamethylsapphyrin (30 mg) was activated by 1,1'-carbonyldiimidazol (2 eq.) in 30 ml of dry THF, room temperature with stirring for 2 hours before being allowed to react with 1 g of 3-aminopropyl-functionalized silica gel for 3 days at room temperature. As usual, in this case the product was recovered by filtration.

B. Mixed Sapphyrin-Orotic acid silica gel (ratio 10:1 Sapphyrin-orotic acid)

Orotic acid (0.1 mmol, 0.174 g) were suspended in 5 ml of water. The pH of the resulting solution was then adjusted to pH 7.5 by adding PIPES buffer. The solution was then cooled to 0° C. and 1-(3-dimethylaminopropyl)-3-ethylcarbodiimide (1 mmol, 0.174 g) was added. After 1 hour 0.5 g of silica gel (prepared as described was added. The reaction mixture was then stirred for 48 hours at room temperature and the product filtered off, washed (as described above in Example 11, section A, and dried. The yield was 1.18 g.

C. Preparation of phenyl substituted sapphyrin silica gel, structure 37 where Ar=phenyl Solution of benzoylchloride (0.3 g) in 25 ml of dry dichloromethane was slowly added under nitrogen to the suspension of partially functionalized sapphyrin silica gel, see Example 11, section E, (1 g) with 0.5 ml of dry pyridine. The reaction mixture was stirred at room temperature for 2 days, then product was filtered off and washed as described in Example 11, section A. Yield 1.09 g.

D. Preparation of 4-nitrophenyl substituted sapphyrin silica gel, structure 37 where Ar=4-nitrophenyl The same procedure as described above in Example 16, section C, was also carried out using 4-nitrobenzoylchloride as a acylation agent.

E. Preparation of naphtyl substituted sapphyrin silica gel, structure 37 where Ar=naphthyl The same procedure as described above in Example 16, section C, was also carried out using naphtoic acid chloride as a acylation agent.

F. Preparation of 4-nitrobenzyl substituted sapphyrin silica gel, structure 37 where Ar=4-nitrobenzyl Solution of 4-nitrobenzylbromide (0.3 g) in 25 ml of dry dioxane was slowly added to suspension of 1 g of partially substituted sapphyrin silica gel, see Example 11, section D, (1 g) in dioxane (50 ml) with 1 g of potassium carbonated reflux. Reflux was continued for 3 hours, then allowed to cool to room temperature, solid material was filtered off, washed with water (250 ml), then methanol (100 ml) and dichloromethane (50 ml); dried, yield 1.09 g. The similar procedure was used for modification of sapphyrin silica gel as in Example 11, section A, using 4-nitrobenzylchloride for reaction with silanol groups on silica gel surface. The similar procedure (with pyridine as a base and 4-nitrobenzoyl chloride as a reagent) was used for the introduction of acyl on silanol groups.

EXAMPLE 17

SAPPHYRIN SUBSTITUTED GLASS CAPILLARIES FOR ELECTROPHORESIS

Polymer-supported expanded porphyrins may be prepared in which the polymer is a glass capillary, intended for use in capillary electrophoresis (CE).

As glass is chemically similar to silica gel (both are silicate-derived), the preparation of modified glass surfaces may be achieved generally as described herein. Different combinations of Z and $R^8$ groups may also be employed.

A. Preparation of sapphyrin modified 3-amidosubstituted glass 1 g of Aminopropyl glass (firma Sigma, 75° A average pore size, 200–400 mesh, 250 mol primary amine per g of glass) was suspended in dry dichloromethane and 0.5 ml was added. A solution of 3,8,17,22-tetraethyl-12-(chlorocarbonylethyl)-2,7,13,18,23-pentamethylsapphyrin (63 mg, 0.1 mmol) in 20 ml of dry dichloromethane was slowly added under argon and reaction mixture stirred at room temperature for 3 days. The product was filtered off, washed with dichloromethane (50 ml), methanol (50 ml), water (50 ml), methanol (20 ml) and dichloromethane (20 ml). Yield 1.05 g.

B. Preparation of sapphyrin modified arylamine glass

The same procedure as described above in Example 17, section A was also carried out using arylamine substituted glass (from Sigma).

C. Silylation of sapphyrin modified glass

The same procedures as described above in Example 12, sections A and B, were carried out.

EXAMPLE 18

SELECTIVE NUCLEOTIDE TRANSPORT BY SAPPHYRIN-NUCLEOBASE CONJUGATES

As discussed above, the sapphyrin molecule itself, which remains monoprotonated in the ca. $3.5 \leq pH \leq 10$ regime,[5,18] is ineffective as a GMP carrier at pH 7, even in the presence of a large excess of C-Tips.[18] Therefore, sapphyrin systems in which nucleotide recognition units were appended directly onto the phosphate-chelating core, were synthesized, as described in the preceding examples.

Transport studies were carried out, using a standard[20] Aq I-$CH_2Cl_2$-Aq II liquid membrane cell, using the sapphyrin cytosine conjugates represented by structures 10 and 20. Both 10 and 20 were found to be able to effect the selective through-membrane transport of GMP at, or near, neutral pH (Table 3).

TABLE 3

Initial Nucleotide Transport Rates ($k_T$) for Carriers 10 and 20.

| Carrier[a] $k_C/k_C$ | (pH)[b] | Aq. I | Aq. II | $k_T$ CMP ($10^{-9}$ mol/cm$^2$ · h)[c] | $k_T$ GMP | $k_T$ AMP | $k_G/k_A$ |
|---|---|---|---|---|---|---|---|
| 10 | 6.15 | $H_2O$ | 0.12 | 12.0 | 1.57 | 7.6 | 100 |
| 10 | 7.05 | $H_2O$ | 0.0005 | 0.011 | 0.001 | 11 | 22 |
| 10 | 6.70 | 10 mM NaOH | 0.30 | 12.3 | 2.82 | 4.4 | 41 |
| 10 | 7.05 | 10 mM NaOH | 0.16 | 7.08 | 0.74 | 9.6 | 44 |
| 20 | 6.15 | $H_2O$ | 0.16 | 1.01 | 0.73 | 1.4 | 6.3 |
| 20 | 7.05 | 10 mM NaOH | 0.049 | 1.15 | 0.36 | 3.2 | 24 |
| none | 6.15 | $H_2O$ | $<10^{-4}$ | $<10^{-4}$ | | $<10^{-4}$ | dd |
| sap[e] | 7.0 | 10 mM NaOH | $<10^{-4}$ | $<10^{-4}$ | | 0.004 | |

[a]0.1 mM in dichloromethane
[b]The source phase, Aq I, contained a 1:1:1 ratio of AMP, CMP, and GMP at a 10 mM conc. (in each). The initial pH was adjusted by the careful addition of NaOH$_{aq}$.
[c]Transport experiments were performed in a manner similar to those reported in refs. 14 and 5. Values reported are the average of three independent measurements; estimated error <5%.
[d]Not determined.
[e]Control experiment using 3, 8, 12, 13 17, 22-hexaethyl-2, 7, 18, 23-tetramethylsapphyrin (0.1 mM) as the putative carrier.

As can be seen from Table 3, both 10 and 20 are able to effect the selective through-membrane transport of GMP at, or near, neutral pH. Using the standard[14] detection system, a quantitative analysis of uridine 5'-monophosphate (UMP) in Aq II could not be made. In qualitative control experiments, it was confirmed, however, that carrier 20 caused no apparent increase in the rate of through-membrane UMP transport at pH 6.7.

Interestingly, in all cases, receptor 20 displays a higher selectivity for GMP (by a factor of 8–100 relative to either AMP or CMP), than its congener 10. Further, better through-transport efficiency is always observed when the receiving phase (Aq II) is kept highly basic. Finally, a significant drop off in efficiency, for both 10 and 20, is observed as the initial pH of Aq I is increased from 6.15 to 7.05.

The above results are considered consistent with a model wherein complexation between the monoprotonated, form of the receptor and the monobasic ([ROPO$_3$H]$^-$) form of GMP takes place at the Aq I-CH$_2$Cl$_2$ interface to produce a neutral, organic-soluble, supramolecular complex such as that depicted in FIG. 4C. This model is in accord with X-ray diffraction data in which the 2:1 complex formed between monobasic phenyl phosphate and diprotonated sapphyrin was analyzed in the solid state. One phenyl phosphate is bound on the "top" face of the macrocycle to each of three pyrroles, while the other phosphate is bound to two pyrroles on the "bottom" side.

This model, and the structure presented in FIG. 4C, provides a simple rationale for the experimental findings: First, decreased selectivity would be expected upon the introduction of "extra" cytosine chelating subunits, since this would result in an increase in number of possible hydrogen bonding interactions and an incumbent loss in required substrate specificity. Second, higher through-transport rates would be observed in those cases where the receiving phase is kept basic since sapphyrin deproteination and facilitated product release at the CH$_2$Cl$_2$-Aq II interface would necessarily be favored. Finally, a decrease in through-transport rate is predicted since a lower concentration of the putative substrate, monobasic GMP (the [ROPO$_3$H]$^-$ form) in Aq I, would be expected as the second phosphate-centered ionization constant of GMP (pKa=ca. 6.7[21]) is first approached and then surpassed (charge neutralization as a requirement for efficient carrier mediated transport is known as Fick's First Law).

That some transport occurs even at pH 7.05 is thus considered a reflection of the fact that, under the conditions of the experiment, binding of monobasic GMP is enhanced relative to that of the dibasic ([ROPO$_3$]$^{2-}$) form and that this binding enhancement, in turn, serves to augment the effective concentration of this monoanionic (and hence readily neutralizable) species in the organic membrane phase.

EXAMPLE 19

SAPPHYRIN-DNA INTERACTIONS

The present inventors have discovered that sapphyrin binds to double- and single-stranded DNA and RNA, and furthermore, that it does so in a novel and unexpected manner.

A. Sapphyrin Binds to DNA

The first evidence for sapphyrin DNA binding came from the observation that an excess of sapphyrin, which is green in solution, can rapidly and specifically precipitate green DNA fibers. The inventors propose that this binding and precipitation is due to the chelation of the polyanionic sugar-phosphate backbone of DNA. This leads to charge neutralization and through the resulting hydrophobic effects, the DNA falls out of solution. Such precipitation effects have not been reported for other DNA binding compounds which are known to either intercalate or groove bind with DNA.

Further evidence that sapphyrin binds to DNA was provided by CD spectroscopy, a technique that can detect chirality. Sapphyrin is an achiral macrocycle that shows no significant CD spectra by itself in solution. However, in the presence of DNA, a sapphyrin CD spectrum was induced. This is consistent with relatively rigid binding to DNA, a chiral macromolecule, which places sapphyrin in a chiral environment and yields the observed induced CD effect.

In addition, UV-Visible spectroscopy provides still further evidence that sapphyrin binds DNA. Upon addition of a large excess of DNA, changes in the visible absorption spectrum occur. The Soret-like transition that occurs at 410 nm is red-shifted by approximately 12 nm. This is taken as evidence that DNA is interacting directly with the sapphyrin macrocycle.

Finally, the inventors have determined that sapphyrin exhibits enhanced fluorescence in the presence of DNA. Sapphyrin alone shows only minimal fluorescence in aqueous buffered solution, but has been shown to either dimerize or aggregate in polar solvents resulting in a quenching of the sapphyrin fluorescence. The fluorescence enhancement effect discovered by the inventors is thus considered to be the result of binding to DNA which breaks up the dimers/ aggregates and creates "monomeric" sapphyrins bound to DNA. Using this fluorescence enhancement as measurement of binding, the lower limit of the apparent binding constant has been estimated to be approximately $10^6 M^{-1}$.

B. Sapphyrin-DNA Binding is not Intercalation or Groove Binding

Unwinding of double helical DNA has traditionally been accepted as a signature of DNA intercalators. Based on the apparent binding constant obtained using fluorescence spectroscopy, the inventors conducted topoisomerase-based unwinding studies using concentrations of sapphyrin where the sapphyrin macrocycle was significantly bound to the DNA. In such studies, no sapphyrin-mediated DNA unwinding was detected, leading to the conclusion that sapphyrin cannot be intercalating.

Preliminary results have indicated that nearly identical visible absorption changes can be observed when sapphyrin is titrated with either double-stranded DNA or single-stranded DNA. As single-stranded DNA contains no higher order structure, such as a major or minor groove, and the interaction appears to be spectroscopically identical between the two types of DNA, this data demonstrates that sapphyrin cannot be groove binding.

C. sapphyrin Binds to the Phosphate Backbone of DNA

Recent X-ray crystallographic evidence has shown that the sapphyrin macrocycle can bind both monobasic phosphoric acid and monobasic phenyl phosphate. The inventors conducted a study aimed to link this solid state evidence to the interaction between sapphyrin and DNA which occurs in solution. They found that, in solution, spectroscopic similarities exist between sapphyrin in the presence of DNA and sapphyrin in the presence of diethyl phosphate. The latter is a simple phosphate that compares with the phosphates used in the X-ray crystallographic studies.

UV-visible spectral shifts comparable to those obtained with DNA can be observed when sapphyrin is titrated with diethyl phosphate. With diethyl phosphate, the Soret-like transition is red-shifted by approximately 9 nm. In addition, fluorescence enhancement in the presence of diethyl phosphate can be observed as in the case with DNA. The only structural similarity between this simple phosphate and the DNA is the phosphate anion and, when taken in conjunction with the X-ray crystallographic data, these spectroscopic techniques provide evidence for the novel mode of DNA binding proposed by the present inventors.

D. Porphyrins and sapphyrins Interact Differently with DNA

To demonstrate that sapphyrins interact differently with DNA than their nearest relatives, porphyrins, the inventors synthesized a porphyrin 39 which was functionalized in a similar manner as the sapphyrin 1. Spectroscopically, these two molecules act very differently in the presence of DNA. Neither an induced CD effect nor any significant shifts in the visible absorption spectrum are observed with the functionalized porphyrin in the presence of DNA. In contrast to the fluorescence enhancement of sapphyrin, the porphyrin shows a decrease in fluorescence intensity in the presence of DNA.

The novel findings described in this example form the basis for even further uses of sapphyrin and sapphyrin derivatives as tools in the research or clinical laboratory. A particularly important application contemplated by the present inventors is to use sapphyrin, or derivatives or polymers thereof, in recovering DNA samples, for example, after electrophoresis. This may be applied as a general technique, or adapted for more specific DNA recognition and recovery by employing functionally derivatized sapphyrins, such as specific sapphyrin-nucleobase or -oligonucleobase conjugates. It is particularly contemplated that silica-supported sapphyrin may be employed in a "DNA catch" method to recover DNA samples from agarose gels.

EXAMPLE 20

SAPPHYRIN, DERIVATIVES AND CONJUGATES AS THERAPEUTIC AGENTS

The discoveries embodied by the present invention may be advantageously exploited in further scientific research, and importantly, in the development of new methods and compositions for treating various human diseases including cancer. Sapphyrins and their derivatives are envisioned to be of use in a wide variety of clinical embodiments, including the binding, delivery and cellular transport of nucleotide derivatives, such as antiviral agents. The sapphyrin-sugar derivatives have the added potential of more specific cellular targeting according to sugar recognition by specific receptors. Sapphyrins and modified sapphyrins also have potential for use directly as chemotherapeutics.

Sapphyrin may also be used as a delivery agent for the intracellular targeting of any drug that has a phosphate group. Of course, given the synthetic methodology disclosed herein, it is contemplated that the sapphyrin may be derivatized by the introduction of further groups to the periphery of the macrocycle, which groups would add the specificity and/or selectivity of the sapphyrin-drug interaction. Sapphyrin-drug interactions of this sort may be based upon either non-covalent interactions, or alternatively, may employ a covalent bond that is cleaved on exposure to the intracellular environment.

In particular embodiments, oligomers or polymers of sapphyrin or sapphyrin-nucleobase conjugates are envisioned to be of use in antisense technology. Such polymers will be of use both in the delivery and transport of oligonucleotides ("oligos"), and in enhancing their effectiveness once inside the target cell. The enhancing effect is based upon the newly discovered properties of sapphyrin in binding to the phosphate portions of nucleic acids. This property will increase the affinity of the antisense construct for its target, and reduce diffusion which generally limits the effectiveness of an antisense molecule. This dual transport and binding role of sapphyrin-oligonucleotide conjugates in anti-sense treatments is particularly advantageous in that no other method or combination of methods available have a DNA (or RNA) affinity component.

The newly-discovered interaction between sapphyrin and DNA, in which sapphyrin acts as a chelate for the phosphate backbone of DNA, is particularly important. The binding constant of unmodified sapphyrin for DNA has been determined to be on the order of $10^6 M^{-1}$, and evidence shows that the mode of DNA binding is not intercalation or groove binding. The inventors will extend these findings and create, using all the available experimental evidence, computer models of the sapphyrin-DNA interaction. These models will allow the design and engineering of covalently linked multimeric sapphyrin molecules with increased affinity and specificity.

These second generation multimeric sapphyrin-based constructs should have a DNA affinity high enough to interfere with biological processes such as transcription and translation. It is contemplated that this will ultimately lead to the development of sapphyrin-based therapeutic agents for use in treating a variety of human diseases, including cancer.

Sapphyrin molecules themselves are also contemplated for use directly as chemotherapeutic agents. Currently available chemotherapeutics generally have complex structures, or complicated modes of interaction with their targets, that preclude systematic improvement. The development of a novel class of DNA binding compounds, namely the sapphyrins of the present invention, therefore creates important new opportunities for the development and use of novel therapeutic agents.

Due to the unique mode of sapphyrin-DNA interaction, the sapphyrin molecule possesses an unrivaled ability to act as a general DNA binding platform. Binding can also be modified so as to adjust both target cell specificity and degree of interaction with the DNA. For sapphyrins, importantly, the basic site of interaction with the DNA involves the interior of the sapphyrin macrocycle, so that the exterior positions $R^1$-$R^{10}$ can be substantially modified without significantly disrupting the DNA binding interaction. These exterior positions can be used to systematically adjust features such as solubility, membrane permeability and cell selectivity. Furthermore, groups designed to modulate interaction with DNA can be attached to the exterior of the sapphyrins including alkylating functions (bromoacetamido groups, ethylene diamine, epoxides etc.) to provide covalent attachment to DNA or ene-diyne moieties to allow for double stranded DNA cleavage.

Another advantage of the sapphyrin system is that the DNA binding motif can be extended to multimeric structures, including the several described in the present application, in which multiple sapphyrins covalently linked together can bind to DNA simultaneously and thus strengthen the entire interaction. This feature will allow a modular approach in which the appropriate number (2–10) of sapphyrin molecules is attached in a single molecule, perhaps with different sapphyrin units containing sapphyrin derivatives with different groups attached that control such important properties such as solubility, target cell specificity and DNA modification ability.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. For example, other macrocyclic, positively-charged entities can be envisioned as binding to phosphate-containing species such as nucleotides, oligonucleotides and DNA by means of the same or similar oriented electrostatic interactions described herein. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

1. Sessler, J. L.; Burrel, A. K. *Topics in Current Chemistry*, 1991, 161, 177–273.
2. V. J. Bauer, D. L. J. Clive, D. Dolphin, J. B. Paine, III, F. L. Harris, M. M. King, J. Loder, S.-W. C. Wang, R. B. Woodward, *J. Am. Chem. Soc.* 105 1983 6429–6436.
3. M. J. Broadhurst, R. Grigg, A. W. Johnson, *J. Chem. Soc., Perkin Trans.* 1 1972, 2111–2116.
4. (a) J. L. Sessler, M. J. Cyr, V. Lynch, E. McGhee, J. A. Ibers, *J. Am. Chem. Soc.* 112 1990 2810–2813. (b) M. Shionoya, H. Furuta, V. Lynch, A. Harriman, J. L. Sessler, *J. Am. Chem. Soc.* 114 1992, 5714–5722.
5. H. Furuta, M. J. Cyr, J. L. Sessler, J. L. *J. Am. Chem. Soc.* 113 1991 6677–6678.
6. J. L. Sessler, M. J. Cyr, A. K. Burrell, *Synlett.* 1991 127–133.
7. Robins, R. K. *Chemical and Engineering News* Jan. 27, 1986, 28–40.
8. "Approaches to Antiviral Agents," Harden, M. R., Ed.; VCH Publishers: Deerfield Beach, Fla., 1985.
9. Holy, A. in *Approaches to Antiviral Agents*, Harden, M. R. (Ed.), VCH Publishers, Deerfield Beach, Fla., 1985, pp. 101–134.
10. (a) Tabushi, I.; Kobuke, Y.; Imuta, J. *J. Am. Chem. Soc.* 1981, 103, 6152–6157. (b) Kimura, E. *Top. Curr. Chem.* 1985, 128, 113–141. (c) Schmidtchen, F. P. *Top. Curr. Chem.* 1986, 132, 101–133. (d) Lehn, J.-M. *Angew. Chem., Int. Ed. Engl.* 1988, 27, 89–112. (e) Marecek, J. F.; Fischer, P. A.; Burrows, C. J. *Tetrahedron Lett.* 1988, 29, 6231–6234. (f) Schmidtchen, F. P. *Tetrahedron Lett.* 1989, 30, 4493–4496. (g) Mertes, M. P.; Mertes, K. B. *Acc. Chem. Res.* 1990, 23, 413–418. (h) Hosseini, W.; Blacker, A. J.; Lehn, J.-M. *J. Am. Chem. Soc.* 1990, 112, 3896–3904. (i) Kimura, E.; Kuramoto, Y.; Koike, T.; Fujioka, H.; Kodama, M. *J. Org. Chem.* 1990, 55, 42–46. (j) Aoyama, Y.; Nonaka, S.; Motomura, T.; Toi, H.; Ogoshi, H. *Chem. Lett.* 1991, 1241–1244. (k) Claude, S.; Lehn, J.-M.; Schmidt, F.; Vigneron, J.-P. *J. Chem. Soc., Chem. Commun.* 1991, 1182–1185. (l) Deslongchamps, G.; Galán, A.; de Mendoza, J.; Rebek, J., Jr. *Angew. Chem., Int. Ed. Engl.* 1992, 31, 61–63. (m) Dixon, R. P.; Geib, S. J.; Hamilton, A. D. *J. Am. Chem. Soc.* 1992, 114, 365–366. (n) Ariga, K.; Anslyn, E. V. *J. Org. Chem.* 1992, 57, 417–419. (o) Muehldorf, A. V.; Van Engen, D.; Warner, J. C.; Hamilton, A. D. *J. Am Chem. Soc.* 1988, 110, 6561–6562. (p) Adrian, J. C.; Wilcox, C. S. *J. Am. Chem. Soc.* 1989, 111, 8055–8057. (q) Benzing, T.; Tjivikua, T.; Wolfe, J.; Rebek, J., Jr. *Science*, 1988, 242, 266–268. (r) Seel, C.; Vögtle, F. *Angew. Chem. Int. Ed. Engl.* 1991, 30, 442–444. (s) Goodman, M. S.; Rose, S. D. *J. Am. Chem. Soc.* 1991, 113, 9380–9382. (t) Lindsey, J. S.; Kearney, P. C.; Duff, R. J.; Tjivikua, T.; Rebek, J., Jr. *J. Am. Chem. Soc.* 1988, 110, 6575–6577. (u) Ogoshi, H.; Hatekeyama, H.; Kotani, J.; Kawashima, A.; Kuroda, Y. *J. Am. Chem. Soc.* 1991, 113, 8181–8183.
11. A. K. Burrell, J. L. Sessler, M. J. Cyr, E. McGhee, J. A. Ibers, *Angew. Chem.* 103 1991 83–85; *Angew. Chem. Int. Ed. Engl.* 30 (1991) 91–93.
12. J. L. Sessler, D. Ford, M. J. Cyr, H. Furuta, *J. Chem. Soc., Chem. Commun.* 1991, 1733–1735.
13. *The Biochemistry of the Nucleic Acids*, 10th ed., Adams, R. L. P.; Knowler, J. T.; Leader, D. P. (Eds.), Chapman and Hall, New York, 1986.
14. Furuta, H.; Furuta, K.; Sessler, J. L. *J. Am. Chem. Soc.* 1991, 113, 4706–4707.
15. *Cell Surface Carbohydrate Chemistry*, Ed. R. E. Harmon, Academic Press, New York, 1978, p. 225, G. A. Jarnieson: Surface Glycoproteins of Normal and Abnormal Platelets p. 311: B. Paul, W. Korytnyk: Cell Surface as a target for chemotherapy. Potential inhibitors of Biosynthesis of Protein-Carbohydrate Linkage in Glycoproteins.
16. R. J. Bernacki, M. Sharma, N. K., Poter, Y. Rustum, B. Paul, W., Korytnyk: J. Supramol. Structure 7, 235–250 1977.
17. Sessler, J. L.; Morishima, T.; Lynch, V. *Angew. Chem., Int. Ed. Eng.* 1991, 30, 977–980.
18. Furuta, H.; Morishima, T.; Kral, V.; Sessler, J. L., *Supramolec. Chem.*, in press.
19. Sessler, J. L.; Magda, D.; Furuta, H. *J. Org. Chem.* 1992, 57, 818–826.
20. Tsukube, H. in *Liquid Membranes: Chemical Applications*, Araki, T.; Tsukube, H. (Eds.), CRC Press, Boca Raton, 1990, pp. 27–50.
21. Phillips, R.; Eisenberg, P.; George, P.; Rutman, R. J. *J. Biol. Chem.* 1965, 240, 4393–4397.
22. Sessler, J. L.; Cyr, M.; Furuta, H.; Kral, V.; Moody, T.; Morishima, T.; Shionoya, M.; Weghorn, S. *Pure & Appl. Chem.* 1993, 65, 393.
23. (a) "Chemical and Enzymatic Synthesis of Gene Fragments: A Laboratory Manual"; H. G. Gassen and A. Lang, eds.; Verlag Chemie, Weinham, 1982. (b) "Oligonucleotide Synthesis: A Practical Approach"; M. J. Gait, ed.; IRL Press; Washington, D.C.; 1984.
24. Uhlman, E.; Peyman,.; *Chem. Rev.* 1990, 90, 544.
25. Brown, P. R.; Roman, M.; *J. Chrom.* 1992, 592, 3.
26. "HPLC in Biotechnology"; W. S. Hancock, ed.; J. Wiley & Sons: New York; 1990.
27. Frenz, J.; Quan, C. P.; Cacia, J.; Vasser, M.; Slikowski, M. B.; *J. Chrom.* 1993, 634, 229.
28. Chaiken, I. M.; Fassina, G.; Caliceti, P. in "High Performance Liquid Chromatography"; J. Wiley; New York; 1989; pp 317–336.
29. "Rainin HPLC Instrumentation and Supplies Catalog", 1992–1992, 3.01–3.04.
30. Takemoto, K.; Inaki, I.; Miyamoto, T.; Nagae, S.; *Poly. J.* 1989, 21, 19–33.
31. Tehrani, J.; Macromber, R.; Day, L.; *J. High Res. Chrom.* 1991, 14, 10–14.
32. Zare, R. N.; Arias, A. A.; Blaschke, T. F.; Ng, M.; *Anal. Chem.* 1992, 64, 15.
33. Rawn, J. D. "Biochemistry"; Neil Patterson Publishers, Burlington, N.C.; 1989; pp 237–286.
34. Colin, H. C.; in "HPLC"; Brown, P. R.; Hartwick, R. A., eds.; J. Wiley; New York; 1989; pp 415–478.
35. Sessler, J. L.; Kral, V.; Furuta, H.; *J. Am. Chem. Soc.* 1992, 114, 8704.
36. (a) Fodora-Csorba, K. *J. Chrom.* 1992, 624, 353–367. (b) Grob, R. L.; Oostdyk, T. S.; Snyder, J. L.; McNally, M. E., *J. Chrom. Sci.* 1993, 31, 183–191. (c) Grob, R. L. *J. Liq. Chrom.* 1993, 16, 1783–1802. (d) Gaind, A. K.; Loconto, P. R. *J. Chrom. Sci.* 1989, 27 569–573.
37. (a) Kostiainen, R.; Bruins, A. P.; Hakkinen, V. M. A. *J. Chrom.* 1993, 113–118. (b) Ember, L. C. & E. N. 1993 03 May, pp 8–9. (c) Ember, L. C. & E. N. 1992, 29 Jun., pp 19–20. (d) Ember, L. C. & E. N. 1992, 23 Nov., pp 14–15.

38. Corey, E. J., Cho, H., Rucker, Ch., Hua, D. H.: Tetrahedron Lett. 1981, 22, 3455–3458).

39. Wagner, R. W., Matteucci, M. D., Lewis, J. G., Gutierrez, A. J., Moulds, C., Froehler, B. C. 1993, *Science*, 260, 1510–1513.

We claim:

1. A method for separating a first molecule from a mixture of at least two molecules, the method comprising contacting said mixture with a matrix-supported expanded porphyrin to separate said first molecule from said mixture, wherein the matrix-supported expanded porphyrin further comprises a nucleobase-containing group.

2. The method of claim 1 wherein the nucleobase-containing group is attached to the matrix support of the matrix-supported expanded porphyrin.

3. The method of claim 1 wherein the nucleobase-containing group is attached to the expanded porphyrin of the matrix-supported expanded porphyrin.

4. The method of claim 1 wherein the nucleobase-containing group comprises a nucleoside or a nucleotide or a derivative thereof.

5. The method of claim 1 wherein the nucleobase-containing group comprises from 1 to 10 nucleobase units.

6. A method for separating a first molecule from a mixture of at least two molecules, the method comprising contacting said mixture with a matrix-supported sapphyrin to separate said first molecule from said mixture, wherein the matrix-supported sapphyrin has the structure:

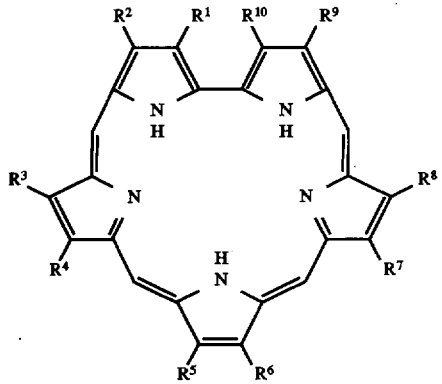

III wherein, each of $R^1$–$R^{10}$ is independently H, alkyl, alkene, alkyne, halide, alkyl halide, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, aldehyde, ether, ketone, carboxylic acid, phosphate, phosphonate, sulfate, phosphate substituted alkyl, phosphonate substituted alkyl, or sulfate substituted alkyl, such that the total number of carbon atoms in each substituent R is less than or equal to 10; and wherein at least one of $R^1$–$R^{10}$ is of the formula $(CH_2)_n$—A—$(CH_2)_m$—B, wherein A is $CH_2$, O, S, NH or $NR^{11}$, wherein $R^{11}$ is alkyl, alkene, alkyne, halide, alkyl halide, hydroxyalkyl, glycol, polyglycol, thiol, alkyl thiol, substituted alkyl, phosphate, phosphonate, sulfate, phosphate substituted alkyl, phosphonate substituted alkyl, sulfate substituted alkyl, COO, CONH, CSNH, $CONR^{11}$; B is a polymeric or solid support matrix; and n and m are integers of less than or equal to 10 or zero.

7. The method of claim 6 wherein B further comprises an aryl, silyl, siloxy, aminoaryl, amino, amidoaryl or silyloxy group as a linking agent to the support matrix.

8. The method of claim 6 wherein the support matrix is selected from the group consisting of silica gel, silica, Merrifield resin, glass, controlled pore glass, polystyrene, sepharose, agarose, clay, zeolite and polyacrylamide.

9. The method of claim 6 wherein the matrix-supported sapphyrin further comprises a long chain alkyl group of one to twenty carbon atoms attached to the support matrix.

10. The method of claim 6 wherein the matrix-supported sapphyrin further comprises a long chain alkyl group of one to twenty carbon atoms attached to the sapphyrin.

11. The method of claim 6 wherein said first molecule is a molecule having a negatively charged chloride, bromide, fluoride, phosphate, phosphonate, phosphate ester, arsenate, arsenate ester, sulfate, or sulfonate moiety.

12. The method of claim 6 wherein said first molecule is a molecule having a negatively-charged phosphate moiety.

13. The method of claim 6 wherein said first molecule comprises a nucleobase-containing group.

14. The method of claim 13 wherein said first molecule comprises a nucleoside or a nucleotide or a derivative thereof.

15. The method of claim 13 wherein said first molecule comprises an oligonucleotide.

16. The method of claim 6 wherein said first molecule comprises DNA or RNA.

17. The method of claim 6 wherein said first molecule is an organophosphorus compound.

18. The method of claim 17 wherein said first molecule is a pesticide, a herbicide, or a fungicide.

19. The method of claim 6 wherein the matrix-supported sapphyrin has a structure as shown in any one of structures 31–38 of FIG. 5D.

20. The method of claim 1 wherein the matrix support of the matrix-supported expanded porphyrin is silica gel, silica, Merrifield resin, glass, controlled pore glass, polystyrene, sepharose, agarose, clay, zeolite or polyacrylamide.

* * * * *